US012108970B2

(12) United States Patent
Jazini et al.

(10) Patent No.: US 12,108,970 B2
(45) Date of Patent: *Oct. 8, 2024

(54) SYSTEM AND METHOD FOR FACILITATING OSTEOTOMY OF THE PELVIC

(71) Applicants: Ehsan Jazini, Bethesda, MD (US); Oliver Tannous, Washington, DC (US)

(72) Inventors: Ehsan Jazini, Bethesda, MD (US); Oliver Tannous, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/128,321

(22) Filed: Mar. 30, 2023

(65) Prior Publication Data
US 2023/0233239 A1    Jul. 27, 2023

Related U.S. Application Data

(63) Continuation of application No. 17/365,459, filed on Jul. 1, 2021, now abandoned, which is a continuation of application No. 16/426,843, filed on May 30, 2019, now Pat. No. 11,090,094.

(60) Provisional application No. 62/679,434, filed on Jun. 1, 2018.

(51) Int. Cl.
A61B 17/80        (2006.01)
(52) U.S. Cl.
CPC ...... A61B 17/8066 (2013.01); A61B 17/8052 (2013.01); A61B 17/8095 (2013.01)

(58) Field of Classification Search
CPC ............ A61B 17/1742; A61B 17/8061; A61B 17/8066; A61B 17/808; A61B 17/8095; A61F 2/28; A61F 2/4425; A61F 2002/448; A61F 2002/4485
See application file for complete search history.

(56) References Cited

U.S. PATENT DOCUMENTS

| | | |
|---|---|---|
| 5,408,409 A | 4/1995 | Glassman et al. |
| 6,123,731 A | 9/2000 | Boyce et al. |
| 6,159,211 A | 12/2000 | Boriani et al. |
| 6,478,825 B1 | 11/2002 | Winterbottom et al. |
| 7,594,932 B2 | 9/2009 | Aferzon et al. |
| 8,187,308 B2 | 5/2012 | Mullaney et al. |
| 8,801,791 B2 | 8/2014 | Soo et al. |
| 9,283,048 B2 | 3/2016 | Kostrzewski et al. |
| 9,345,589 B2 | 5/2016 | Stark |
| 9,592,096 B2 | 3/2017 | Maillet et al. |

(Continued)

Primary Examiner — Larry E Waggle, Jr.
(74) Attorney, Agent, or Firm — Reza Ghafoorian

(57) ABSTRACT

A surgical implant system includes a surgical implant and at least one fixation device. The surgical implant includes a first side member, a second side member, a distal member and a proximal member. The first side member is disposed in opposed relation relative to the second side member, the first and second side members including distal and proximal ends. The distal member is disposed in opposed, spaced relation relative to the proximal member. The distal member extends across one end of the surgical implant between the first and second side member connecting distal ends of the first and second side members. The proximal member extends across a second end of the surgical implant connecting the proximal ends of the first and second side members. The fixation device is inserted in and advanced through osseous tissue and traverses the openings of the first and second side members.

2 Claims, 41 Drawing Sheets

(56) References Cited

U.S. PATENT DOCUMENTS

| | | | |
|---|---|---|---|
| 9,687,356 | B1 | 6/2017 | Spangler et al. |
| 9,861,404 | B2 | 1/2018 | Reiley |
| 9,987,051 | B2 | 6/2018 | Nunley et al. |
| 11,090,094 | B2 * | 8/2021 | Jazini ................. A61B 17/8052 |
| 2004/0034430 | A1 | 2/2004 | Falahee |
| 2004/0073314 | A1 | 4/2004 | White et al. |
| 2006/0015184 | A1 | 1/2006 | Winterbottom et al. |
| 2013/0211531 | A1 | 8/2013 | Steines et al. |
| 2014/0067106 | A1 | 3/2014 | Makeig |
| 2015/0100066 | A1 | 4/2015 | Kostrzewski et al. |
| 2016/0213487 | A1 | 7/2016 | Wilson et al. |
| 2016/0213488 | A1 | 7/2016 | Moor et al. |
| 2017/0056116 | A1 | 3/2017 | Kostrzewski et al. |
| 2019/0038329 | A1 * | 2/2019 | Poelstra ............. A61B 17/8066 |

* cited by examiner

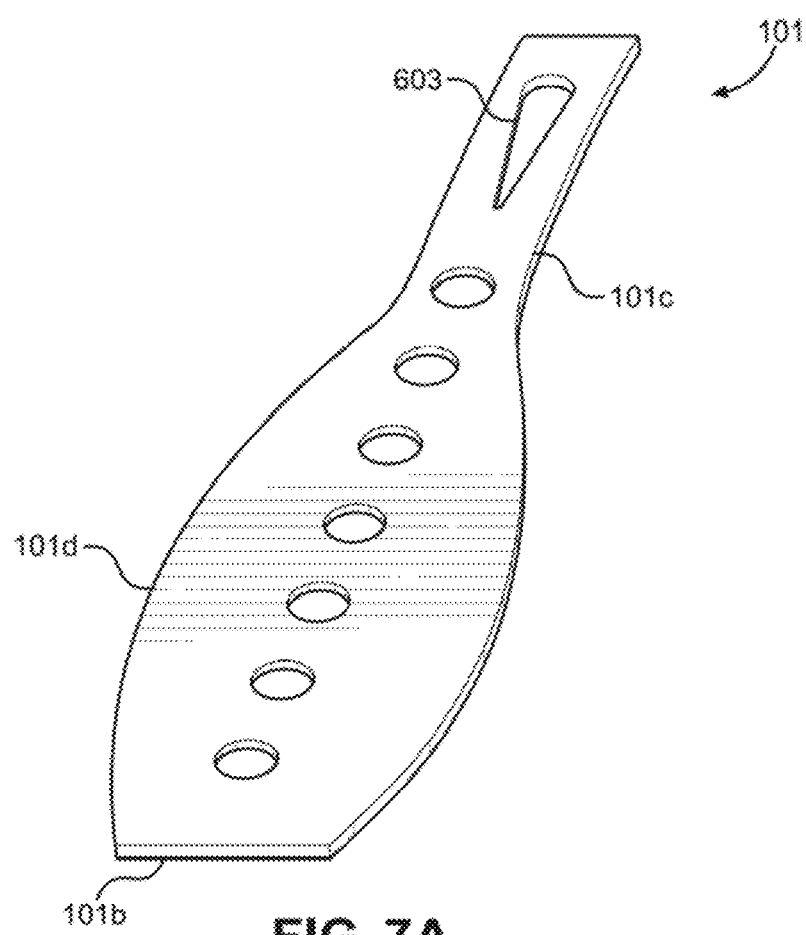
FIG. 7A
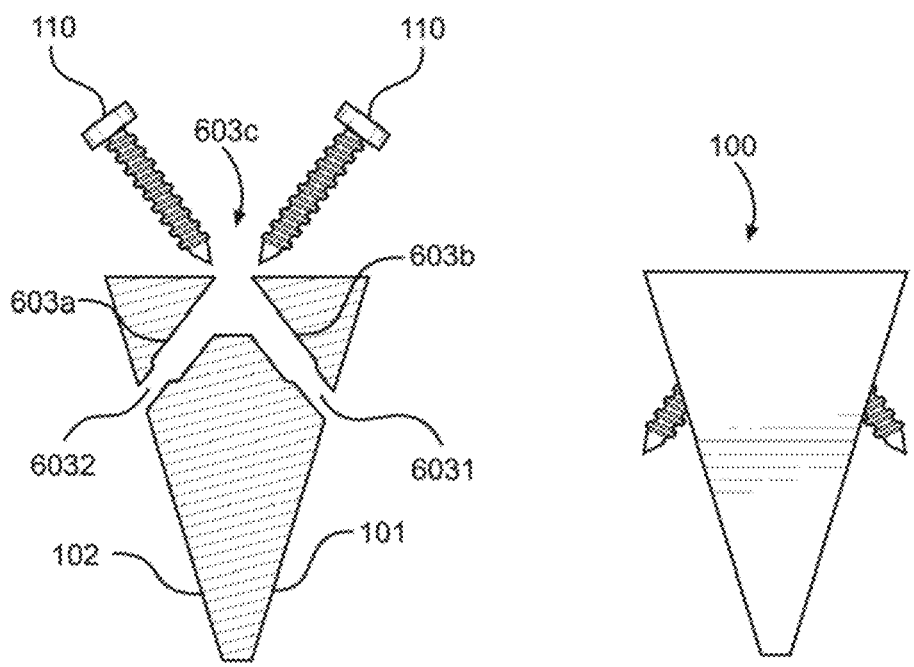
FIG. 7B
FIG. 7C

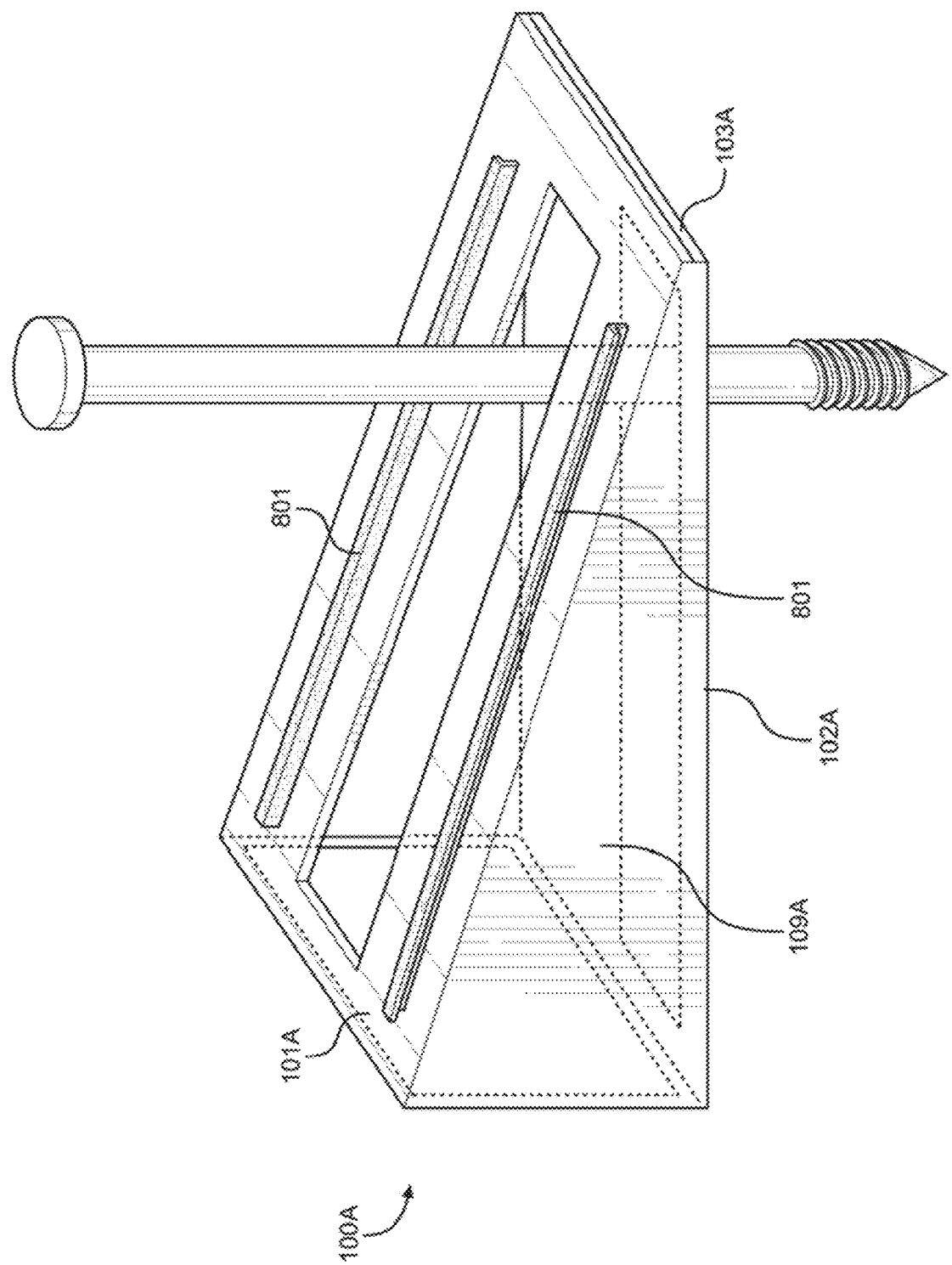

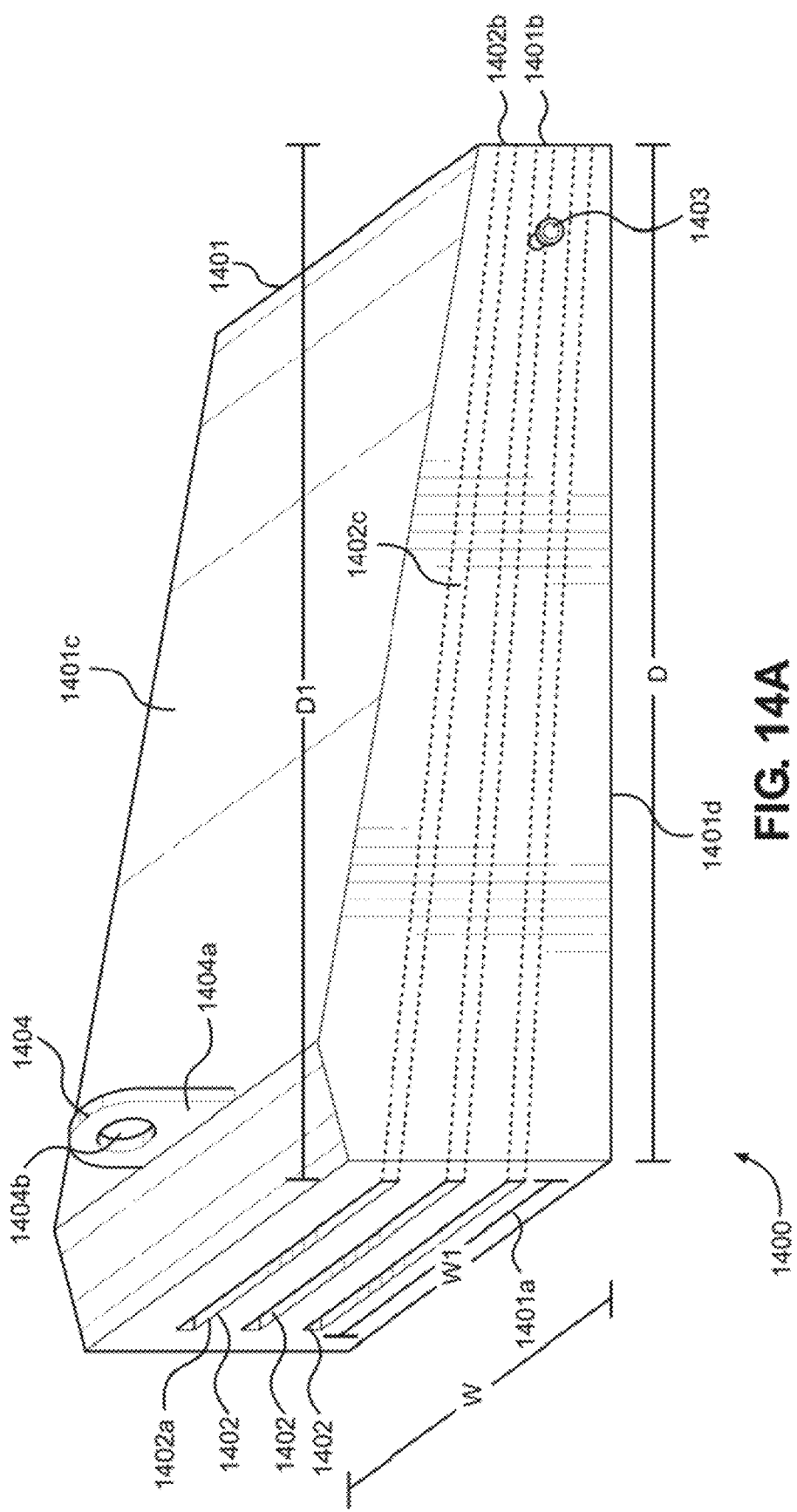

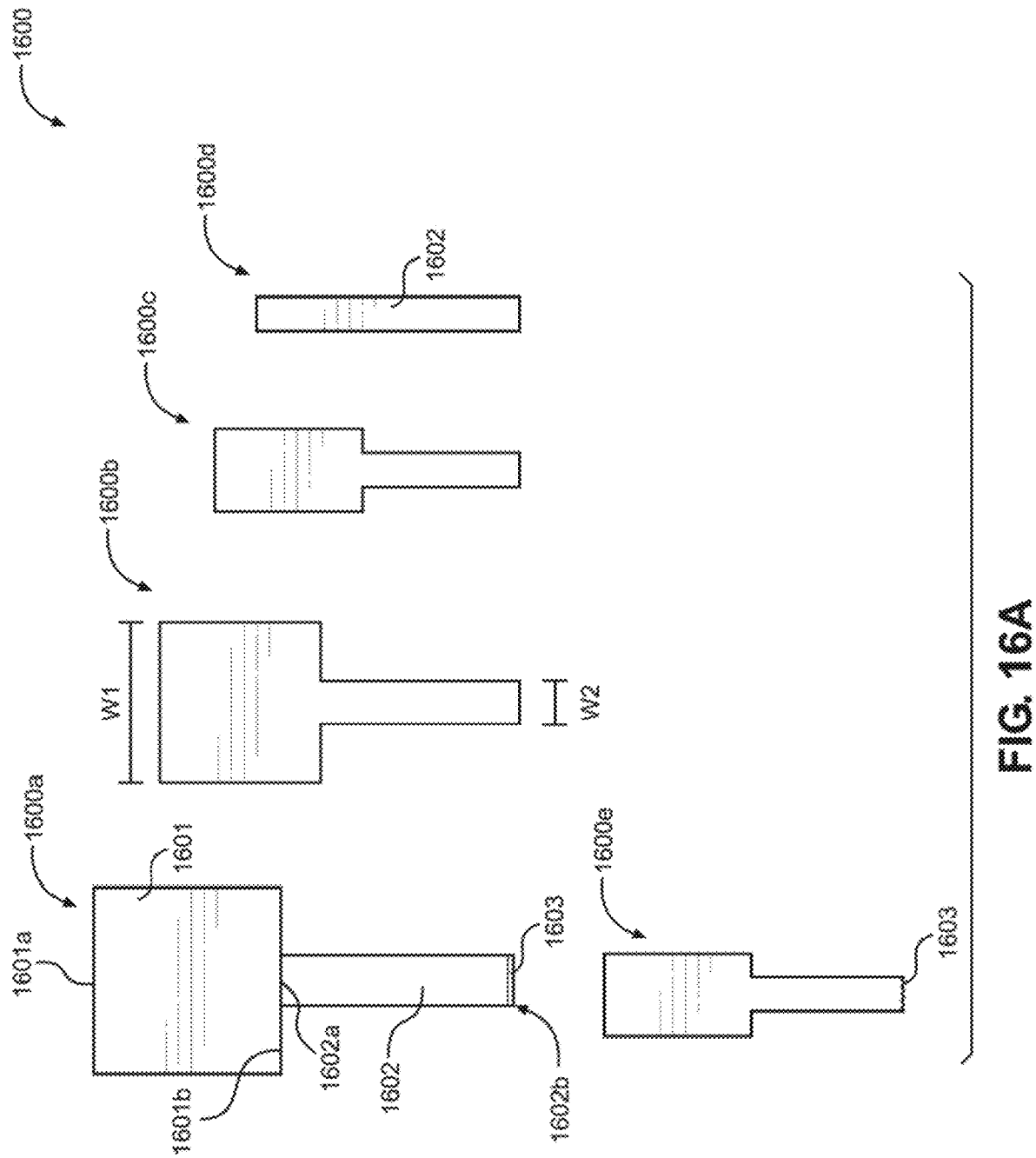

SYSTEM AND METHOD FOR FACILITATING OSTEOTOMY OF THE PELVIC

CROSS-REFERENCE TO RELATED APPLICATIONS

This application claims the benefit of, and priority to, U.S. Provisional Patent Application Ser. No. 62/679434, filed on Jun. 1, 2018, the entire content of which is hereby incorporated herein by reference.

TECHNICAL FIELD

The present disclosure relates generally to orthopedic surgical devices and systems, and more particularly, to surgical implants, surgical implant systems, and methods of cutting of, and securing implants to osseous tissue.

BACKGROUND

Skeletal disorders or deformities can cause depressed ability to walk, balance or perform routine daily functions. Spinal disorders with exaggerated curvature of the spine, such as kyphosis or lordosis, are examples of a skeletal disorder which affect alignment and balance of a patient. Congenital short femur is another skeletal disorder in which one femur is slightly or significantly shorter/smaller than the other femur, causing a limp.

Correction surgeries and other methods directly addressing the spine and the femur have been used to correct balance and improve general skeletal alignment. In patients with spinal deformities, treatments have focused on correcting spine parameters. For congenital short femur, lib lengthening has been the standard treatment. However, the current treatments are complex, inefficient and, expensive and have lengthy recovery time for the patient. Other devices, systems and methods are needed to achieve efficient, less complex and more economical correction of skeletal deformities and disorders.

SUMMARY

In an embodiment, a surgical system A surgical implant assembly comprises at least one surgical implant comprising, a first side member, including at least one first opening, a first side member distal end and a first side member proximal end; a second side member, including at least one second opening, a second side member distal end and a second side member proximal end and disposed in opposed relation relative to the first side member; and, a distal member including a right end and a left end, interconnecting the first and second side members, the right end connecting to the first side member distal end and the left end connecting to the second side member distal end; and, a fixation device, the fixation device insertable through the at least one first opening and the at least one second opening. The surgical implant assembly further comprises a top member and; a bottom member disposed in opposed, spaced relation relative to the top member, the top and bottom members are interconnected through their parameter by the first side member, the second side member, the distal member and the proximal member. The top member and/or the bottom member may be planar or non-planar. The at least first opening may be disposed in opposed relation relative to and aligned with the at least second opening. The surgical implant assembly further comprises a bone plate including an elongate body extending between a first end portion and a second end portion, the elongate body positioned adjacent the proximal member of the surgical implant. The surgical implant further comprises a first curved proximal portion at the proximal end of the first side member; and, a second curved proximal portion at the proximal end of the second side member, wherein the first end portion and the second end portion of the bone plate when positioned adjacent to the surgical implant conform to the shape of the first curved proximal portion and the second curved proximal portion. The surgical implant may have generally a trapezoidal shape including a first angle defined between the distal end of the first side member and the right end of the distal member, and, a second angle defined between the distal end of the second side member and the left end of the distal member. The surgical implant assembly may further comprise a second fixation device for stabilizing and compressing osseous tissue, the second fixation device traverses a space created upon installing the surgical implant, wherein the second fixation device does not contact the surgical implant. The surgical implant may have equal first and second angles. The surgical implant may include different first and second angles the first and second angles may range from about 90° to about 135°. The first side member and/or the second side member may be planar or non-planar. The first side member and/or the second side member may have variable widths along their lengths. The at least a portion of the first and second side member may have a textured finish. The surgical implant assembly may comprise multiple surgical implants, wherein the surgical implants are stackable, each of the multiple surgical implants comprising, at least one connection means for connecting the surgical implant to an adjacent surgical implant in a stack of surgical implants.

A method of implanting a surgical implant into an osseous tissue comprising, forming an opening in the osseous tissue; inserting a surgical implant into the opening of the osseous tissue, the surgical implant comprises a first side member, including at least one first opening, a first side member distal end and a first side member proximal end; a second side member, including at least one second opening, a second side member distal end and a second side member proximal end, the second side member disposed in opposed relation relative to the first side member; and, a distal member including a right end and a left end, interconnecting the first side member and the second side member, the right end connecting to the first side member distal end and the left end connecting to the second side member distal end; and, inserting at least one fixation device through the at least one first opening and the at least one second opening to anchor the surgical implant to the osseous tissue. The method may further comprise attaching at least one bone plate to the proximal member of the surgical implant, the bone plate comprising an elongate body extending between a first end portion and a second end portion. The method may further comprise inserting fixation devices through the first and second end portions of the bone plate to anchor the bone plate to the osseous tissue. The method wherein the surgical implant further comprises at least one cavity defined in the surgical implant and filling the at least one cavity of the surgical implant with bone growth material.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

FIG. 7A is side view of an embodiment surgical implant.

FIGS. 7B-7C are top views of embodiment surgical implants.

FIGS. 9A-9C are 3-dimensional views of components of an embodiment stackable surgical implant system.

FIGS. 14A-14C is 3-dimentsional views of embodiment osteotome guides.

FIG. 16A is side views of embodiment cutting devices or osteotomes.

DETAILED DESCRIPTION

While the principles of the present disclosure are described below with respect to osteotomy of and implant into the pelvic bone, it should be understood that the surgical system and implant of the present disclosure are suitable for insertion into any osseous tissue and/or use in a variety of surgical procedures. Accordingly, a person of ordinary skill in the art will readily appreciate that the size and/or shape of the surgical devices and implants, or components thereof, can be modified for proper alignment and fit within a desired osseous tissue.

Figure 1A:
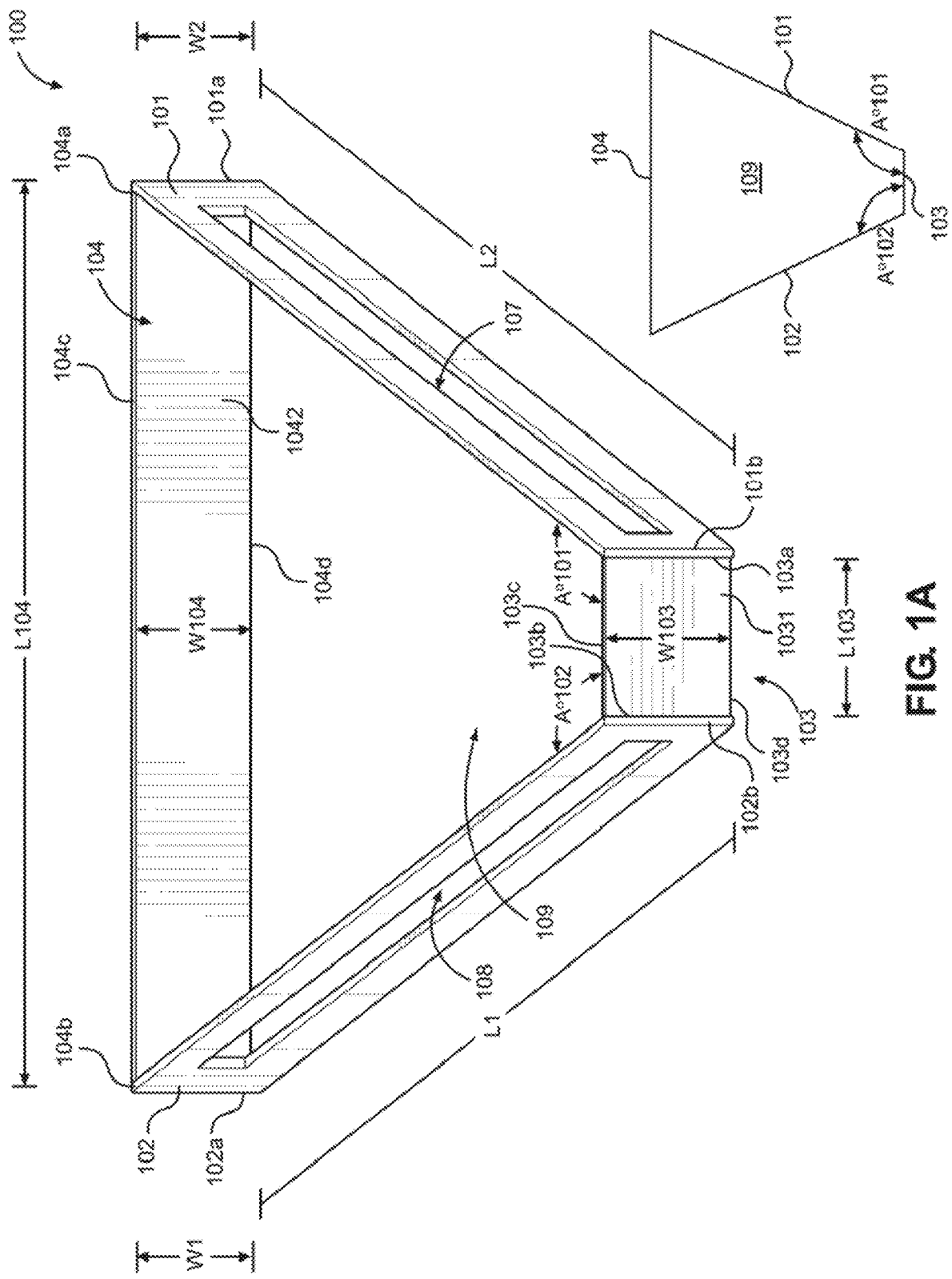
FIG. 1A is a 3-dimensional view of an embodiment surgical implant.

In an embodiment, FIG. 1A illustrates a 3-dimensional view of a surgical implant 100 comprising a first side member 101, a second side member 102, a distal member 103, a proximal member 104. The first side member 101 and the second side member 102 are disposed in opposed relation relative to each other. The distal member 103 and proximal member 104 are disposed in opposed, spaced relation relative to each other and interconnect the first and second side members 101, 102. Each of the first and second side members 101, 102 includes a proximal end 101a, 102a and a distal end 101b, 102b, respectively. The distal member 103 and proximal member 104, each include a right end 103a, 104a and a left end 103b, 104b, respectively. The distal member 103 interconnects the first and second side members 101, 102 by connecting each of the first and second side member distal ends 101b, 102b at the right and left ends 103a, 103b of the distal member 103, respectively. The proximal member 104 interconnects the first and second side members 101, 102 by connecting each of the first and second side member proximal ends 101a, 102a at the proximal member right and left ends 104a, 104b, respectively. At least a cavity 109 exists within the boundaries created by the interconnection of first side member 101, second side members 102, and the distal member 103 and proximal member 104.

In an embodiment, the distal member 103 may have different shapes, including rectangular, triangular, oblong, circular, square or trapezoidal. In an embodiment as shown in FIG. IA, the distal member 103 may be rectangular in shape with a length "$L_{103}$" that is longer than its width "$W_{103}$," the distal member extends across the surgical implant 100 connecting the distal ends of the first and second side members 101, 102. The distal member 103 further includes a right end 103a, a left end 103b, a top end 103c and a bottom end 103d. In yet another embodiment defined therein, the distal member 103 comprises external and internal surfaces 1031, 1032, respectively.

In an embodiment, the proximal member 104 may have different shapes, including rectangular, triangular, oblong, circular, square or trapezoidal. In an embodiment as shown in FIG. 1A, the proximal member 104 may be rectangular in shape with a length "$L_{103}$" that is longer than its width "$W_{103}$," the proximal member extends across the surgical implant 100 connecting the proximal ends of the first and second side members 101, 102. The proximal member 104 may further include a right end 104a, a left end 104b, a top end 104c and a bottom end 104d. In yet another embodiment defined therein, the proximal member 104 comprises external and internal surfaces 1041, 1042, respectively.

In an embodiment, the distal and proximal members 103, 104 may be disposed in parallel or non-parallel relations relative to each other. For example, as illustrated in FIG. 1A, the distal member 103 is disposed in opposed, parallel, spaced relation relative to the proximal member 104, such as in a surgical implant 100 having isosceles trapezoidal shape. In yet another embodiment, the distal member 103, may be disposed in a non-parallel relation relative to the proximal member 104 to accommodate anatomical variability in patients.

In an embodiment as illustrated in FIG. 1A, the surgical implant 100 may have different shapes and dimensions. Example of different shapes include trapezoidal (including irregular quadrilateral/trapezium, trapezoid and isosceles trapezoid), triangular, square, or rectangular. FIG. 1A illustrates a trapezoidal surgical implant 100 wherein the distal member 103 and proximal member 104 are disposed in opposed, spaced relation relative to each another and the length "$L_{103}$" of the distal member 103 is shorter than the length "$L_{104}$" of the proximal member 104. The width "$W_{103}$" of the distal member 103 may be the same or different relative to the width "$W_{104}$" of the proximal member 104. In an embodiment, the widths "$W_{103}$" and "$W_{104}$" may be determined in relation to the widths "W1" and "W2" of the first and second side members, respectively. As illustrated in FIG. 1A, the width "$W_{103}$" of the distal member 103 is equal to the width "$W_{104}$" of the proximal member 104, because the first and second side members 101, 102 are substantially rectangular in shape with equal width "W1" and "W2." In other embodiments described therein, the first and second side member 101, 102 may take the anatomical shape and dimensions of the bone cross-section adjacent to which the first and second side members 101, 102 are positioned, in which case each of the first and second members 101, 102 may demonstrate variable widths along its length.

In an embodiment, each of the first and second side member 101, 102 may comprise a distal end 101b, 102b and a proximal end 101a, 102a. The first and second side member distal ends 101b, 102b may connect to the right and left ends 103a, 103b of the distal member 103 forming internal angles $A°_{101}$ and $A°_{102}$, respectively. The angles $A°_{101}$ and $A°_{102}$ may be equal to or different from one another, depending on the anatomical change or correction desired for a patient.

In an embodiment, the angles $A°_{101}$ and $A°_{102}$ may be equal to or greater than about 90°. As illustrated in FIG. 1A, $A°_{101}$ and $A°_{102}$ are equal to one another and greater than about 90° to form a trapezoid surgical implant 100. In an embodiment, the $A°_{101}$ and $A°_{102}$ may range from about 90° to about 140°. Any angular degree may be selected for the $A°_{101}$ and $A°_{102}$ to adjust or correct anatomical or skeletal alignments, such as by adjusting pelvic incidence, or correct or improve any balance issues. For example, the $A°_{101}$ and $A°_{102}$ may each independently be about 90°, 92°, 94°, 96°, 98°, 100°, 102°, 104°, 106°, 108°, 110°, 112°, 114°, 116°, 118°, 120°, 122°, 124°, 126°, 128°, 130°, 132°, 134°, 136°, 138°, 140°. In embodiments, the $A°_{101}$ and $A°_{102}$ are from about 90° to about 135°. In other embodiments, the $A°_{101}$ and $A°_{102}$ are from about 100° to about 125°.

In an embodiment, each first and second side member 101, 102 may include at least one opening, 107, 108, respectively. The at least one opening 107, 108 may have different shapes. For example, as illustrated in FIG. 1A, the at least one opening 107, 108 may be rectangular and extend substantially the entire length of the first and second side members 101, 102, respectively. In another embodiment, the at least one opening 107, 108 may partially extend the length of the first and second side member 101, 102, respectively. In yet another embodiment, the at least one opening 107, 108 may include different shapes, such as, round, oblong, trapezoidal, rectangular or square.

Figure 1B:
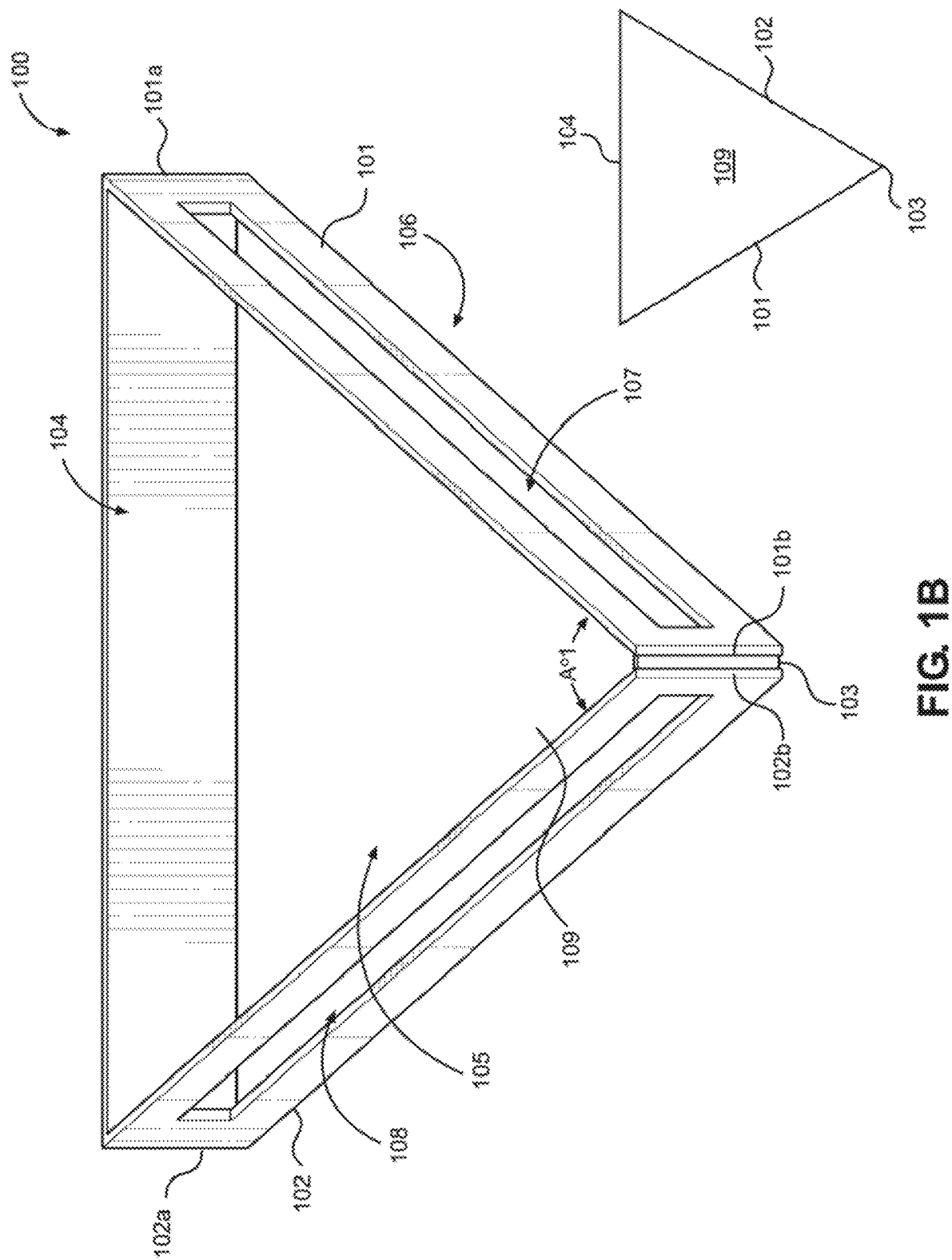
FIG. 1B is a 3-dimensional view of an embodiment surgical implant.

In an embodiment, FIG. 1B illustrates a 3-dimensional view of a surgical implant 100 comprising a first side member 101, a second side member 102, a distal member 103, a proximal member 104, a top member 105, and a bottom member 106. The distal ends 101b and 102b of the first and second side members 101, 102 may come together to define the distal member 103. The top member 105 and the bottom member 106 are disposed in opposed, spaced relation relative to each other, and are interconnected around their perimeter by the first side member 101, the second side member 102, the distal member 103, and the proximal member 104. Together first side member 101, the second side member 102, the distal member 103, the proximal member 104 the top member 105, and the bottom member 106 define a cavity 109 within the surgical implant 100.

The at least one cavity 109 of the surgical implant 100 can reduce the density and/or the stiffness of the surgical implant 100. The at least one cavity 109 may be any shape including, for example, round, oblong, or square, and/or may be defined by concave surfaces. The at least one cavity 109 can extend through one or more surfaces (e.g., the first and second side members 101, 102) of the surgical implant 100. It should be understood that a surgical implant 100 may include at least one cavity 109 of any suitable size and geometry.

The at least one cavity 109 can be configured and dimensioned to receive a bone growth material therein. As used herein, a "bone growth material" can be any material that facilitates osteogenesis. Suitable bone growth materials can be resorbable or non-resorbable, osteoconductive or osteoinductive, and combinations thereof. Non-limiting examples of suitable bone growth materials include synthetic materials, bone morphogenic proteins, and heterologous, homologous, or autologous bone and derivatives thereof.

In an embodiment, as illustrated in FIG. 1B, the surgical implant may be substantially triangular in shape with a first angle "$A°_1$" formed between the distal end of the first side member 101b and the distal end of the second side member 102b. The first angle "$A°_1$" may range from about 3° to about 50°. In other embodiments, the first angle "$A°_1$" may be about 5° to about 45°. The surgical implant 100 may have any first angle "$A°_1$" to adjust or correct anatomical or skeletal alignments, such as by adjusting pelvic incidence, or correct or improve any balance issues.

Figure 1C:
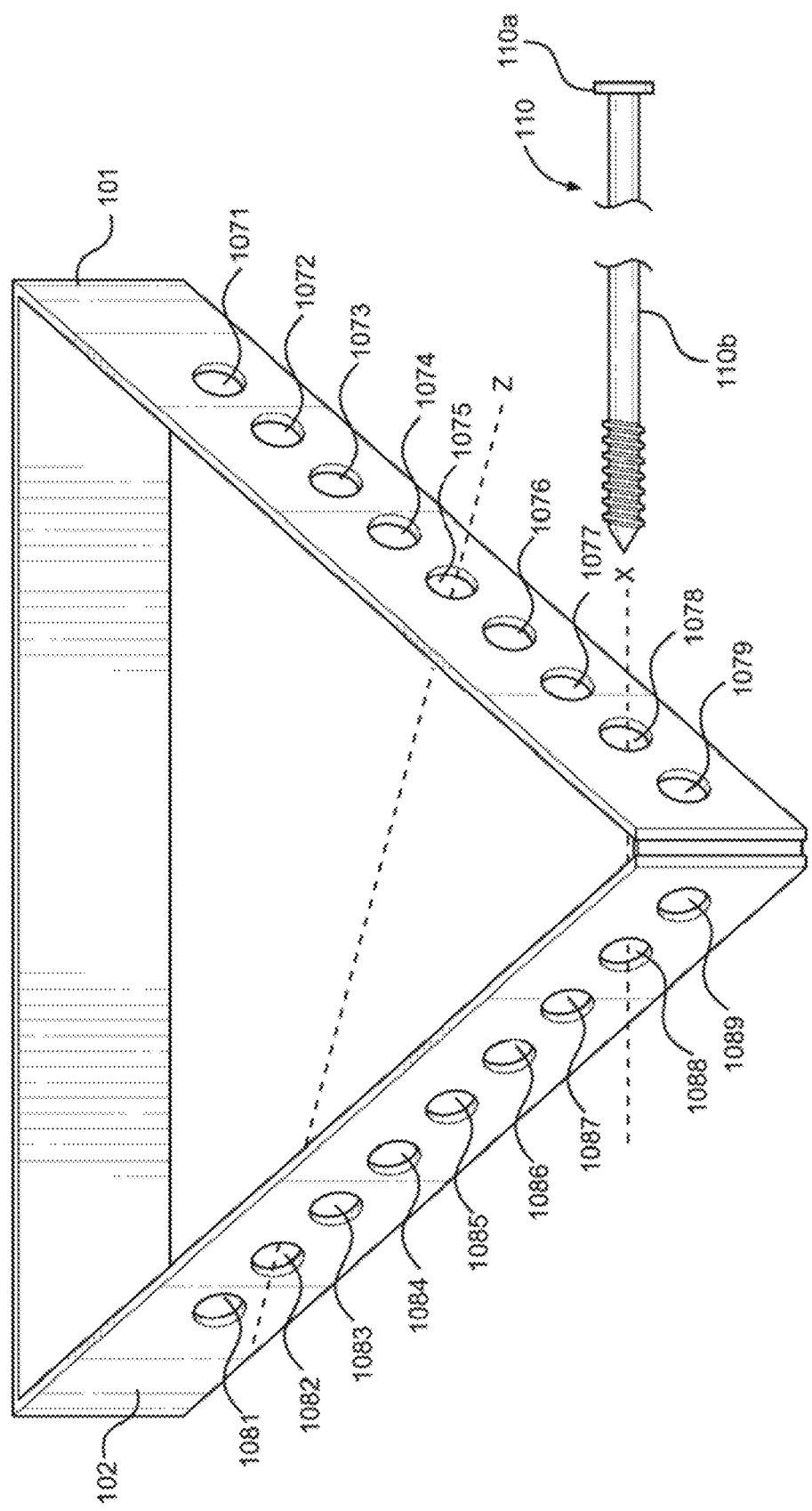
FIG. 1C is a 3-dimensional view of an embodiment surgical implant.

FIG. 1C illustrates a 3-dimensional view of the surgical implant 100 including more than one circular opening 1071, 1072, 1073, 1074, 1075, 1076, 1078, 1079 on the first side member 101 and more than on circular openings 1081, 1082, 1083, 1084, 1085, 1086, 1087, 1088, 1089 on the second side member 102. Each circular opening may be configured to receive a fixation device 110, which may traverse on an "X" axis through osseous tissue adjacent to the first side member, through a circular opening 1078 on the first side member 101, continue to go through the cavity 109, traverse a circular opening 1088 on the second side member 102 and through osseous tissue adjacent to the second side member 102.

A fixation device 110 may be a pin, tap, drill, wire, bone screw and may be used to secure the surgical implant 100 to osseous tissue. Each of the fixation devices 110 may include a head 110a and a threaded shank 110b extending from the head 110a. The fixation devices 110 may be self-tapping or self-starting screws.

In an embodiment, the circular openings on the first and second side members 101, 102 may be disposed in opposed, spaced relation relative to each other and aligned along an "X" axis that runs parallel to the distal or/and proximal members 103, 104. For example, the fixation device 110 may be inserted through the circular openings 1078 and 1088, along the "X" axis. In yet another embodiment, the circular openings on the first and second side members 101, 102 may be disposed in opposed, spaced relation relative to each other along a "Z" axis which is non-parallel to the distal or proximal members 103, 104. For example, the fixation device 110 may be inserted through the circular opening 1076 and 1082, along the "Z" axis. Because the fixation device 110 may traverse osseous tissue before it contacts the openings on the first and second side members 101, 102, the different axes "X," "Z" and related openings may ensure that different angles traveled by the fixation device 110 are captured as the fixation device 110 contacts an opening on the first and second side members 101, 102.

Figure 1D:
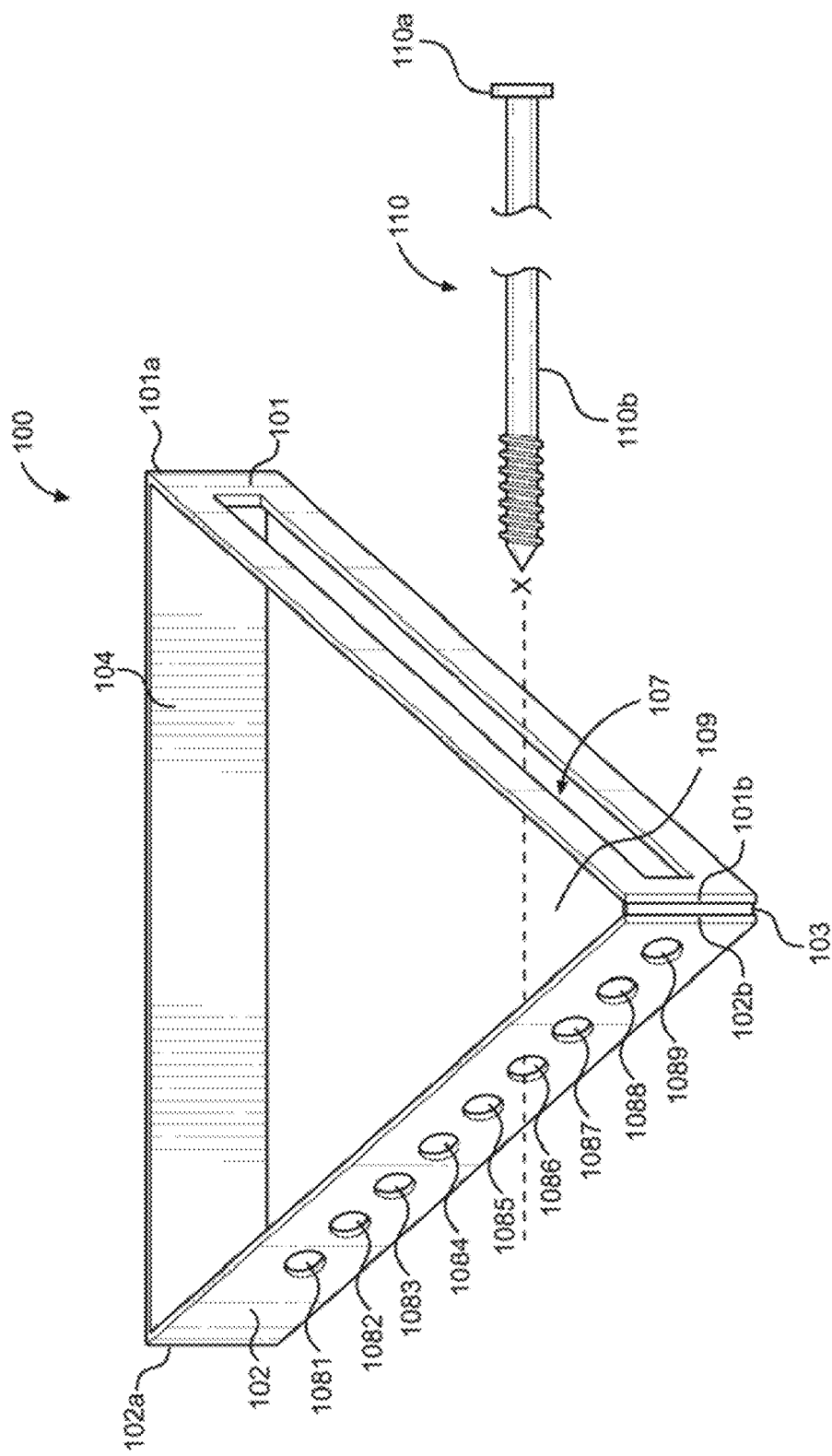
FIG. 1D is a 3-dimensional view of an embodiment surgical implant.

FIG. 1D illustrates a 3-dimensional view of the surgical implant 100 including different types of openings on each first and second side members 101, 102. For example, the first side member opening 107 may be rectangular in shape and substantially extend the entire length/width of the first side member 101. The second side member 102 may include more than one second side member openings 1081, 1082, 1083, 1084, 1085, 1086, 1087, 1088, 1089. The first side member opening 107 on the first side member 101 may be aligned with the more than one second side member openings 1081, 1082, 1083, 1084, 1085, 1086, 1087, 1088, 1089 on the second side member 102 in a manner to allow traverse of the fixation device(s) 110 through the first side member openings 107 and one of the more than one second side member openings 1081, 1082, 1083, 1084, 1085, 1086, 1087, 1088, 1089. For instance, the fixation device 110 may traverse through osseous tissue and when it reaches the surgical implant 100, it traverses through the first side member opening 107, through the cavity 109, and through one of the more than one second side member openings 1086.

Figure 1E:
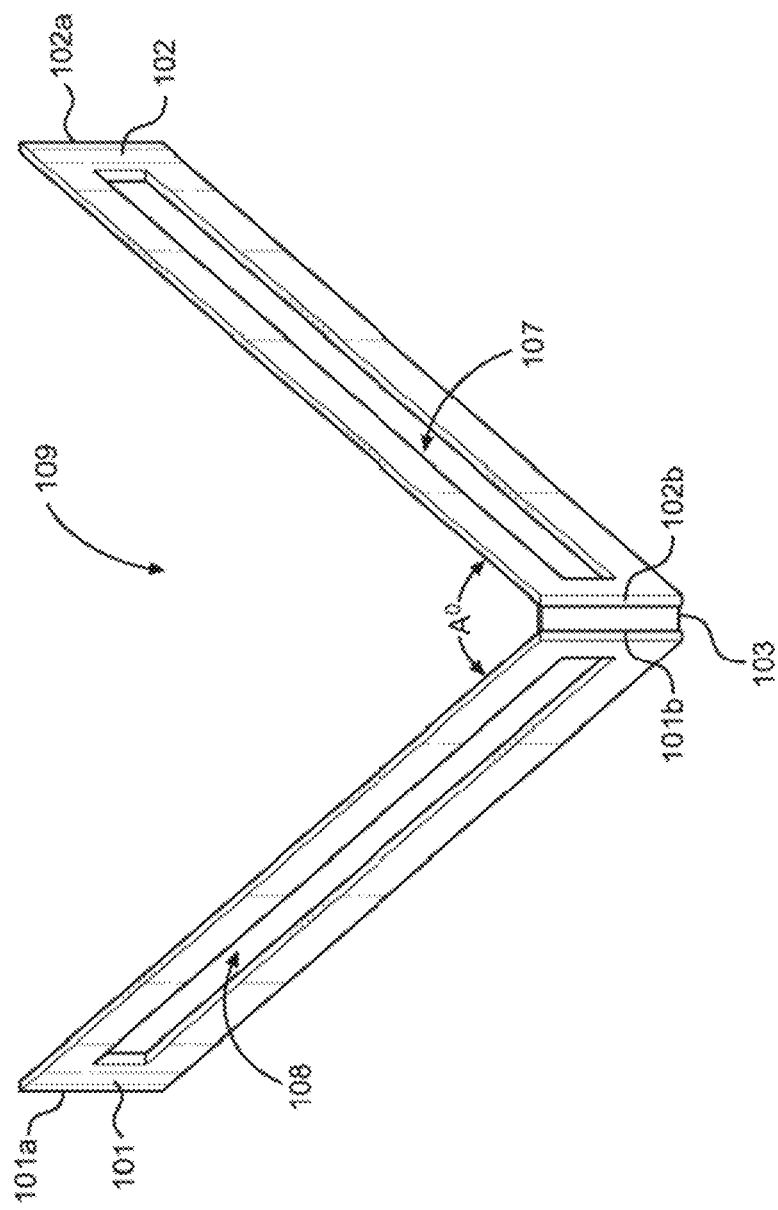
FIG. 1E is a 3-dimensional view of an embodiment surgical implant.

FIG. 1E illustrates a 3-dimensional view of the surgical implant 100 including a first side member 101, a second side member 102 and a distal member 103. The first and second side members 101, 102 come together to form distal member 103. The surgical implant 100 may be substantially "V" shaped with an angle $A°_2$. The angle $A°_2$ may range from about 2° to about 50°. The $A°_2$ may be any angle which would allow correction or adjustment in patient's anatomical or skeletal structure or to rectify a patient's balance, among other things.

It is envisioned that the surgical implant 100 may be solid, open-faced, and/or expandable. The surgical implant 100 may be expanded by an active or passive mechanism and/or include a height expansion/reduction mechanism to allow for dynamic changes to the height and/or length of the surgical implant 100. It is contemplated that the changes in the height and/or length can alter the foregoing angles, such as "$A°_{102}$" or "$A_1$", of the surgical implant 100 to accommodate or correct patient anatomy. The surgical implant 100 can be built in-situ by a user inside of osseous tissue to tailor the surgical implant 100 to conform to the anatomy of an individual patient.

Figure 2A:
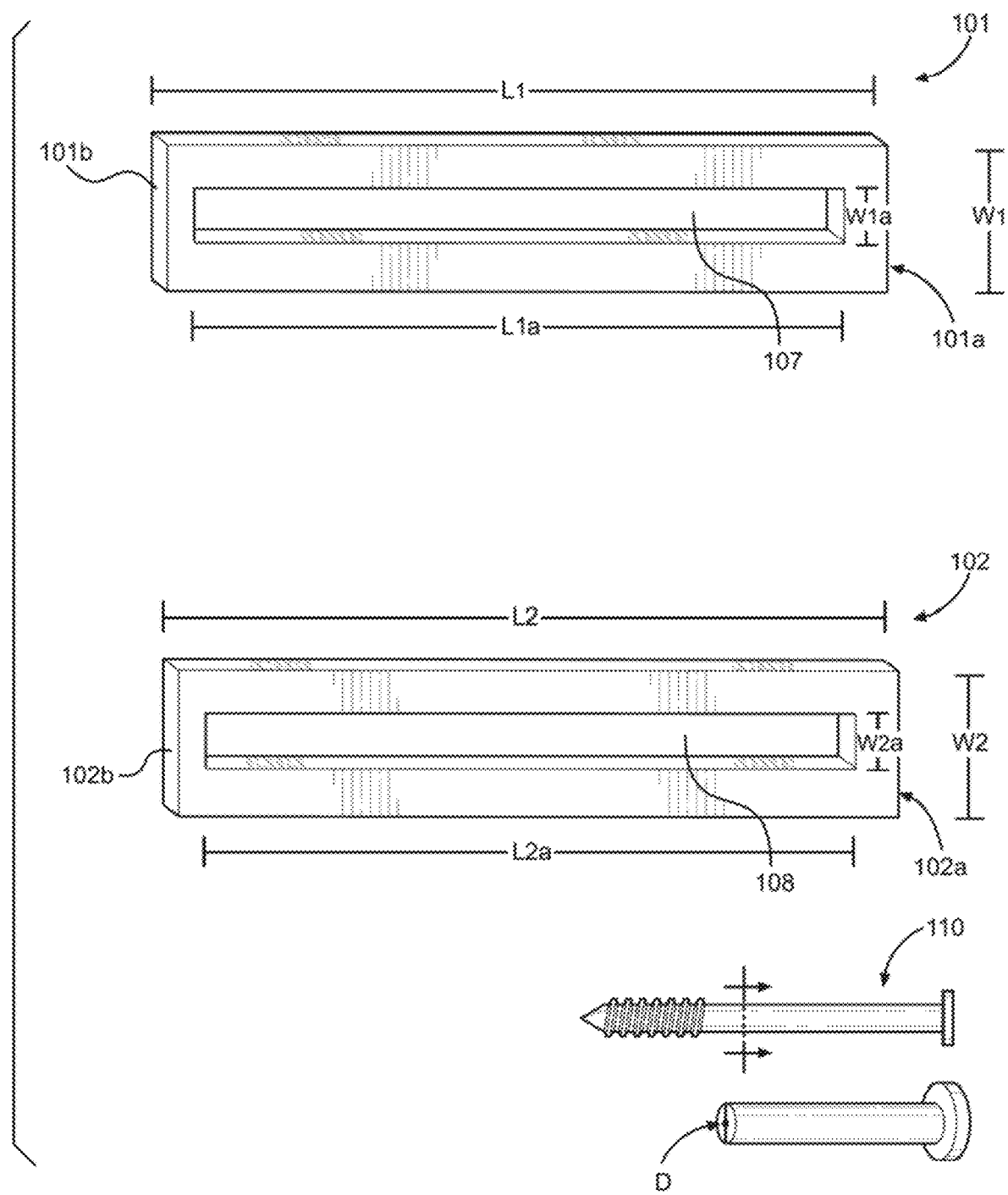
FIG. 2A is a side view of first and second side members of an embodiment surgical implant.

In another embodiment, FIG. 2A illustrates a side surface view of each of the first and second side members 101, 102, each including a length "L1," "L2" and width "W1," "W2," respectively. The first and second side members 101, 102 may have identical or different lengths "L1," "L2" and/or widths "W1," "W2," respectively. Different lengths "L1," "L2" and/or widths "W1," "W2" allows for customization of the surgical implant to fit a patient's anatomical structure.

In another embodiment, the first side member 101 may include at least a first side member opening 107 with a length "L1a" and width "W1a" and the second side member 102 may include at least one second side member opening 108 with a length "L1b" and width "W1b." The shapes and sizes of the at least one opening 107, 108 may be different. For example, the lengths "L1a" and "L2a" of the first and second side members 101, 102 may substantially extend the entire or a portion of the first and second side member length "L1," "L2," respectively. For example, the first and second side member opening 107, 108 may comprise lengths "L1a" and "L2a" that extend a range of about 4% to about 95% of the lengths "L1" and "L2," respectively. The lengths "L1a" and "L2a" may be identical or different. In embodiments where the opening lengths "L1a," "L2a" represent the short diameter of an elliptical opening, the lengths of "L1a," "L2a" may be determined based on the diameter length of a fixation device 110 traversing the opening 107, 108. For instance, the lengths "L1a," "L2a" (e.g., short diameter of an ellipse) may range from about 0.5% to about 20% larger than the diameter of the fixation device 110. The lengths "L1a," "L2a" may be about 1%, 3%, 5%, 7%, 9%, 11%, 13%, 15%, 17%, 19% larger than the diameter "D" of the fixation device 110.

In an embodiment, the widths "W1a," "W2a" of the first and second side member openings 107, 108 may substantially extend the entire widths "W1," "W2" or a faction of widths "W1," "W2." For example, the lengths "W1a" and "W2a" may extend a range of about 2% to about 95% of the lengths W1 and W2, respectively. In another embodiment, the widths "W1a," "W2a" may be determined in relation to the portion of the fixation device 110 which will traverse the openings 107, 108. For example, the widths "W1a," "W2a" may be designed to snugly or loosely hug the traversing fixation device 110 on its two sides. The widths "W1a," "W2a" may be substantially the same as or larger than the diameter of the fixation device 110 traversing them. For instance, the widths "W1a," "W2a" may range from about 0.5% to about 20% larger than the diameter of the portion of the fixation device 110 which traverses the opening 107, 108. The widths "W1a," "W2a" may be about 1%, 3%, 5%, 7%, 9%, 11%, 13%, 15%, 17%, 19% larger than the diameter of the traversing fixation device 110. In the instances where the openings 107, 108 include circular openings, "W1a," "W2a" of the circular openings are the diameter of the circular opening 107, 108. In the instances where openings 107, 108 are elliptical, "W1a," "W2a" of the elliptical opening may be the short diameter of the ellipse.

Figure 2B:
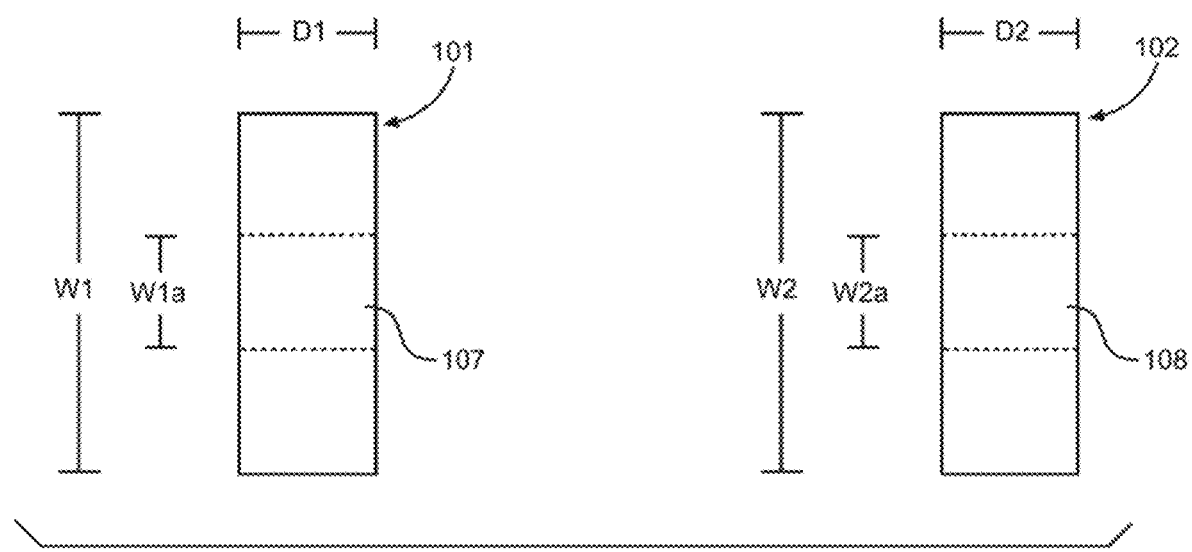
FIG. 2B is an end view of the first and second side members of an embodiment surgical implant.

In an embodiment, FIG. 2B illustrates an end view of the first and second side members 101, 102. The first and second side members each may have a depth "D1," "D2" and width "W1," "W2," respectively. The first and second side member at least one opening 107, 108 may extend the thickness of or depth "D1," "D2" of the first and second side members 101, 102.

Figure 2C:
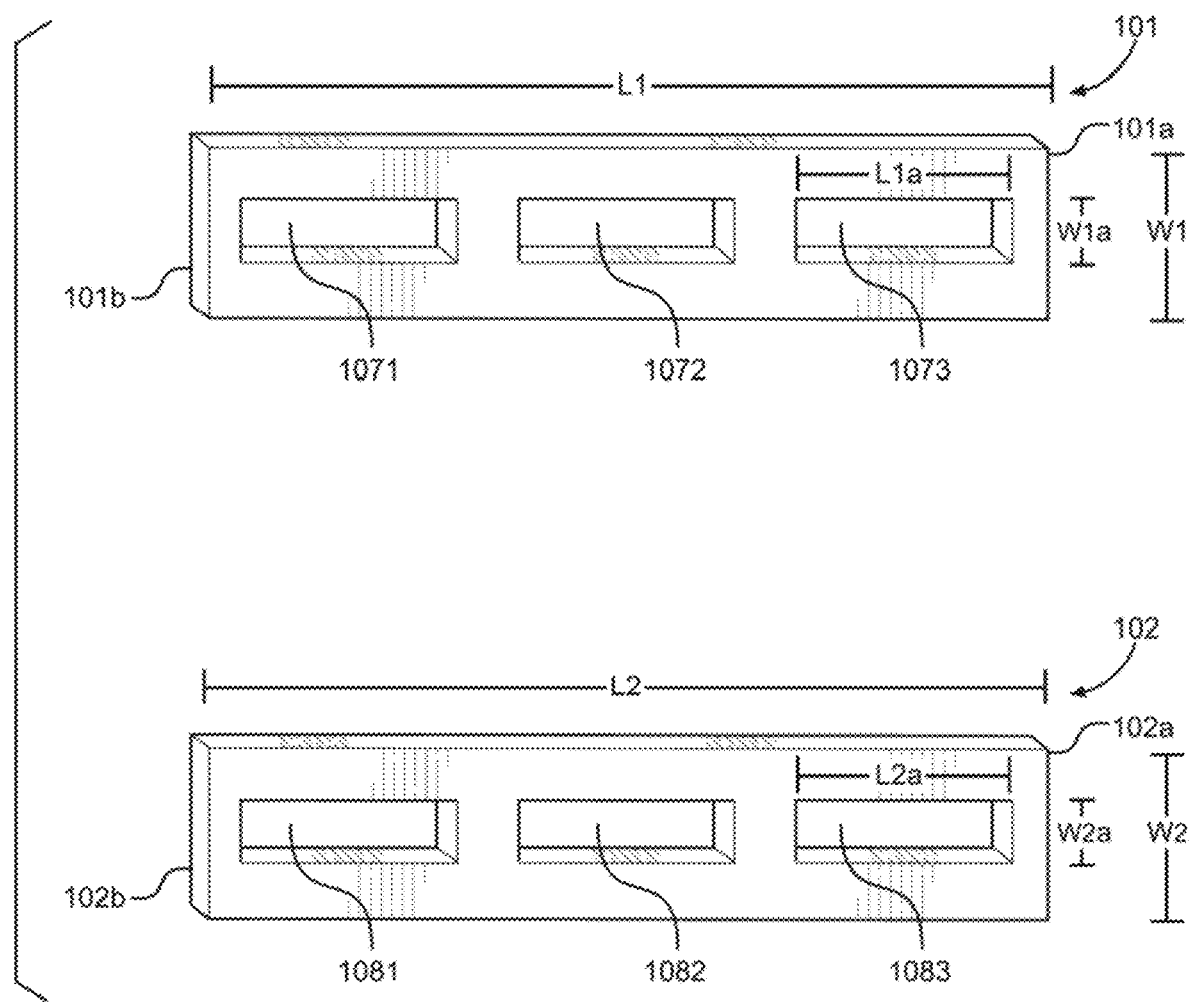
FIG. 2C is a side view of the first and second side members of an embodiment surgical implant.

In an embodiment, FIG. 2C illustrates a side surface view of the first and second side members 107, 108 of a surgical implant 100. For example, the first side member 101 may include multiple openings 1071, 1072, 1073, each including a length "L1a" and width "W1a." Each first side member opening 1071, 1072, 1073 may have similar or different dimensions relative to each other, such as similar or different lengths "L1a" and/or widths "W1a."

Similarly, as illustrated in FIG. 2C, the second side member 102 may include multiple openings 1081, 1082, 1083, each including a length "L2a" and width "W2a." Each second side member opening 1081, 1082, 1083 may have similar or different dimensions relative to each other, such as lengths "L1b" and widths "W1b." In an embodiment, each first side member opening 1071, 1072, 1073 may have similar or different length "L1a" and/or width "W1a" as compared to each second side member opening 1081, 1082, 1083 length L2a and/or width "W2a."

Figure 2D:
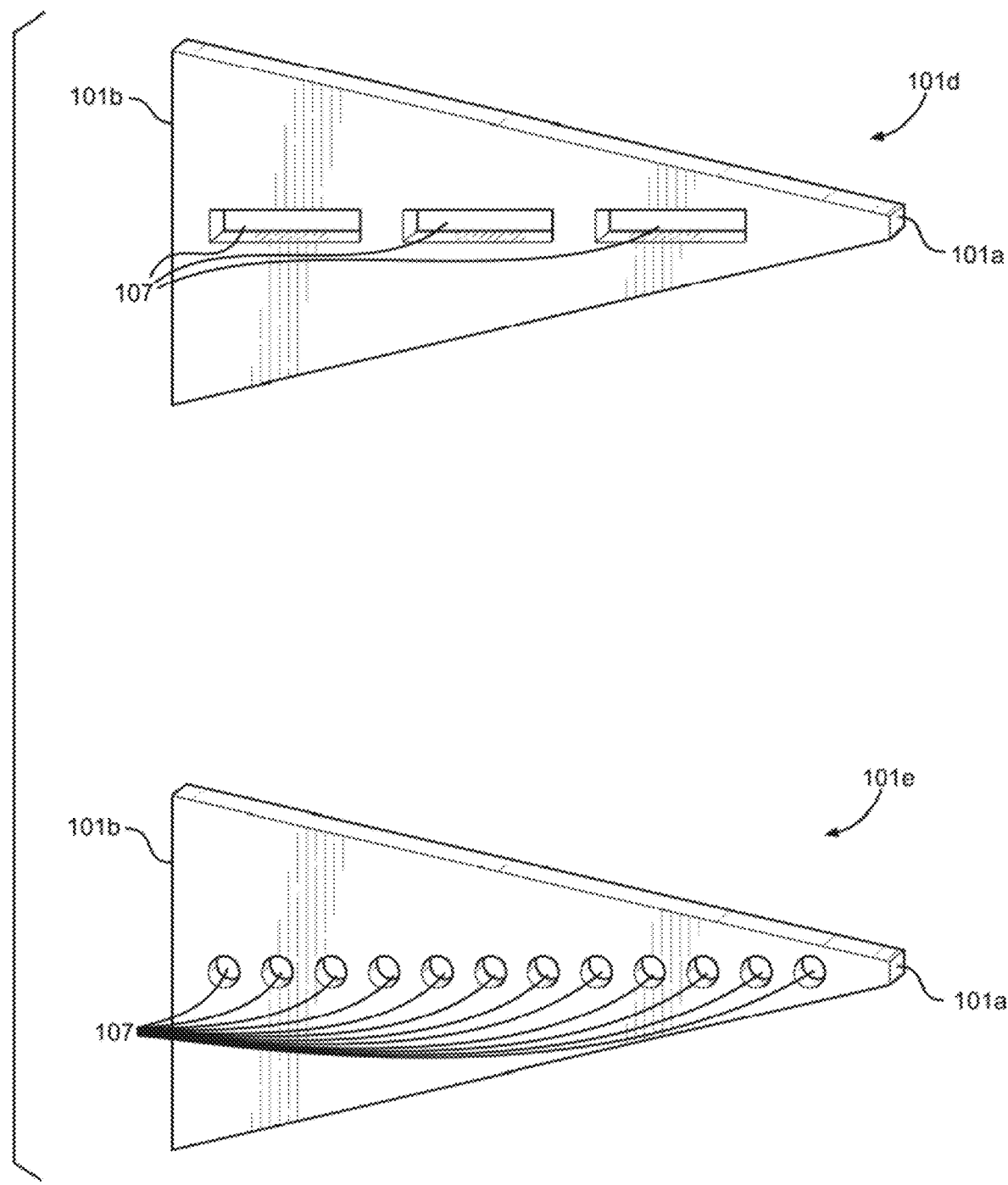
FIG. 2D is a side view of exemplary first or second side member of an embodiment surgical implant.

In an embodiment, FIG. 2D illustrates side views of exemplary first (or second) side members 101d, 101e. For instance, the first side member 101d may be substantially triangular including multiple rectangular openings 107. The first side member 101d may be substantially trapezoidal including multiple circular openings 107. Second side member 102 (not shown) may be identical to or different from the first side members 101d, 101e.

Figure 2E:
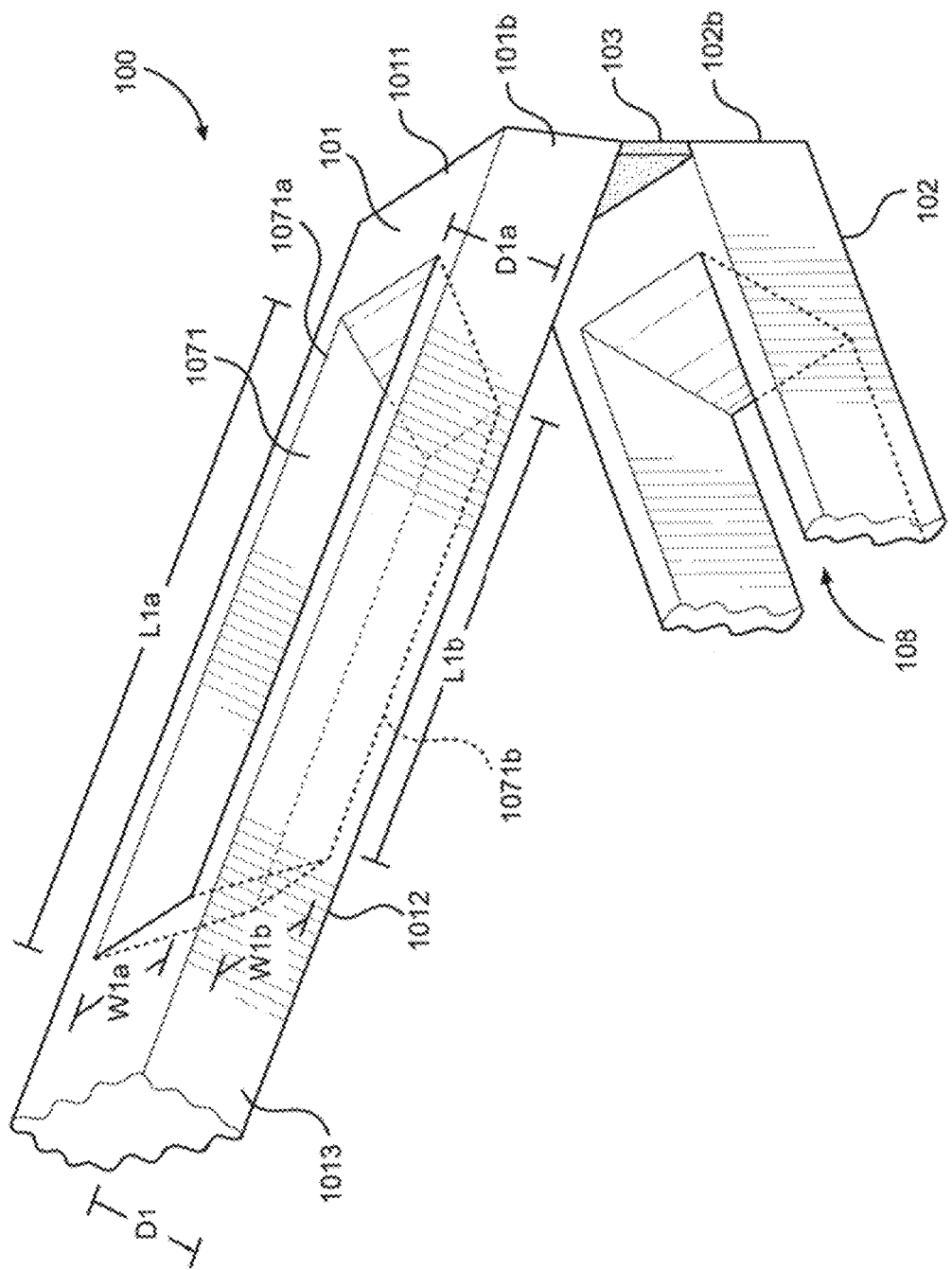
FIG. 2E is a 3-dimensional view of a portion of an embodiment surgical implant.

In an embodiment, the first and/or second side member openings 107, 108 may be configured to allow the fixation device 110 to be inserted in the openings 107, 108 in a multidirectional manner. For example, FIG. 2E illustrates a 3-dimensional view of a portion of a surgical implant 100 comprising multidirectional first and second side member openings 107, 108 (partially illustrated). The first side member 101 comprises at least an exterior surface 1011, an interior surface 1012 and two side surfaces 1013, 1014. The first side member may further include a multidirectional opening 1071. The opening 1071 can traverse the thickness D 1 of the first side member 101 and may include a first opening 1071a on the first side member exterior surface 1011 connected to a second opening 1071b on the first side member interior surface 1012. The first opening 1071a may be rectangular with a length "L1a" and "W1a." The second opening 1071b may also be rectangular with "L1b" and "W1b." In a multidirectional opening, the length "L1a" and width "W1a" of the first opening 1071a may be longer than the length "L1b" and width "W1b" of the second opening 1071b, or vice versa. Alternatively, only the length "L1a" is longer than the length "L1b," or vice versa, and the widths "W1a" and "W1b" are similar. The reduction in size of the first opening 1071a as compared to the second opening 1071b allows angular and multidirectional insertion of fixation devices 110 into the openings, as the fixation device 110 approaches the first opening 1071a as when existing osseous tissue. Similar or reverse configurations are contemplated and are apparent for at least one opening 108 on the second side member 102.

Figure 2F:
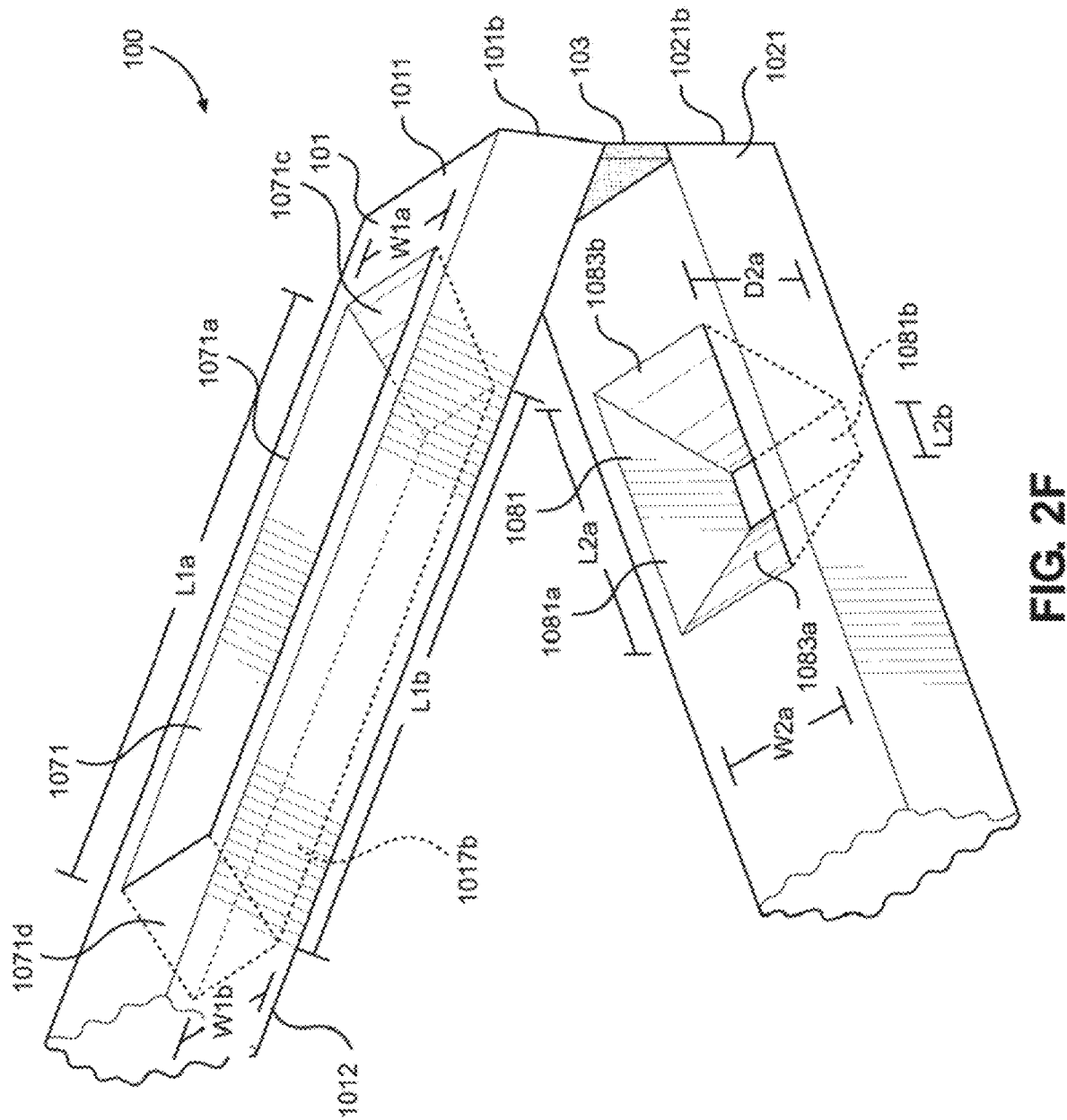
FIG. 2F is a 3-dimensional view of a portion of an embodiment surgical implant.

In an embodiment, FIG. 2F illustrates an embodiment surgical implant 100 comprising a rectangular opening 1071 in the first side member 101 and an opening 1081 on the second side member 1021. The rectangular opening 1071 extends through the thickness of the first side member 1011 and comprises a first opening 1071a located on the exterior surface of the first side member 1011, a second opening 1071b located on the interior surface of the first side member 1012, a distal side wall 1071c, and a proximal side wall 1071d. The distant and proximal side walls 1071c, 1071d extend across the depth of the first side member and interconnecting the top and bottom openings 1071a, 1071b, respectively. The first opening 1071a is connected to the second opening 1071b through the thickness of the first side member 101. Each of the first and second openings 1071a, 1071b include identical length "L1a" as compared to "L1b" and width "W1a" as compared to "W1b," respectively. The first opening 1071a is disposed in opposed, spaced relation relative to the second opening 1071b, wherein the second opening 1071b is positioned off alignment relative to the first opening 1071a in a manner that the distal and proximal side walls 1071c, 1071d of the opening 1071 are not perpendicular to the exterior or interior surfaces 1011, 1012 of the first side member 1011.

Figure 3A:
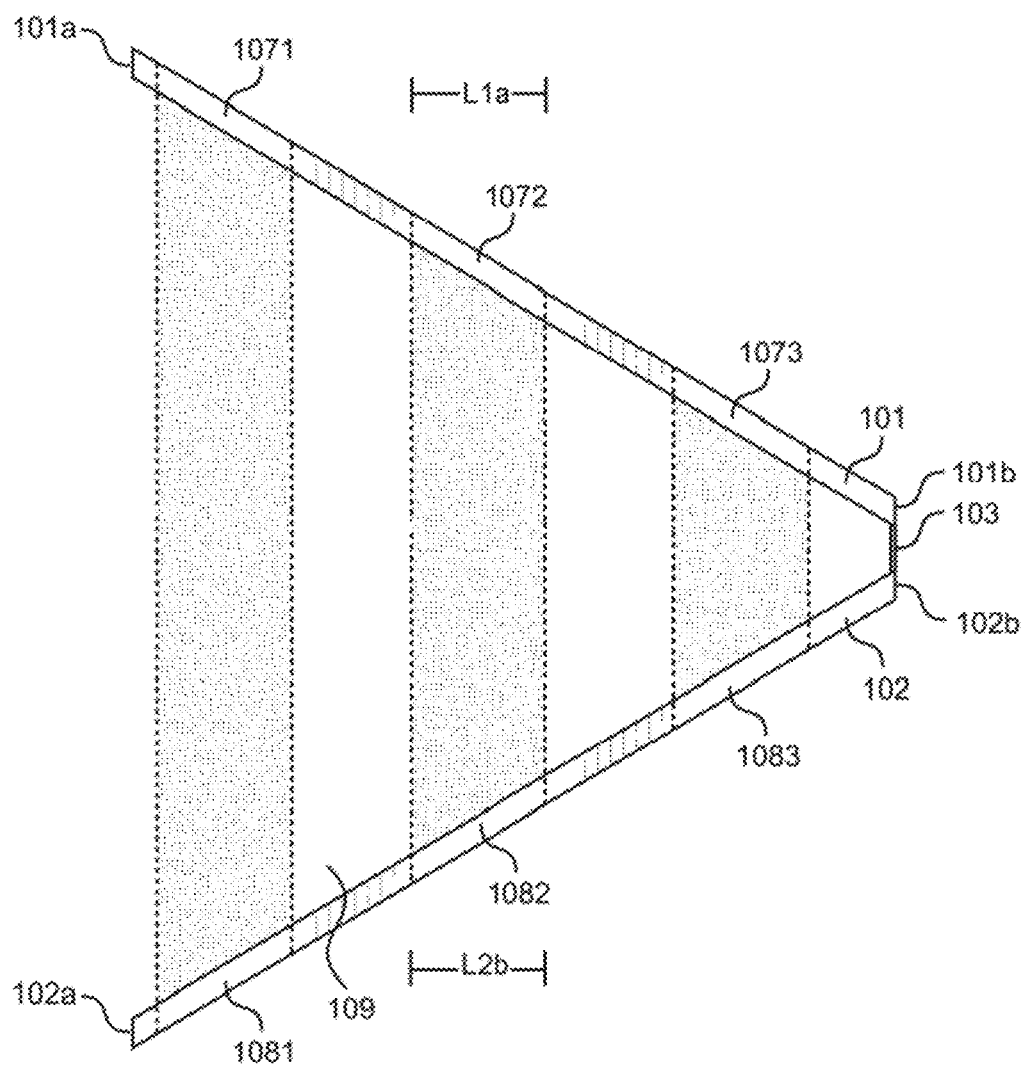
FIG. 3A is a top view of an embodiment surgical implant.

In an embodiment, FIG. 3A illustrates a top view of an embodiment surgical implant 100 and exemplary alignments between openings of the first and second side members 101, 102. The surgical implant 100 may be configured to align each of the openings 1071, 1072, 1073 on the first side member 101 with a corresponding opening 1081, 1082, 1083 on the second side member 102. The purpose of the alignment is to guide the fixation device 110 (not shown) traversing through the surgical implant and to ensure the fixation device traverse through the intended openings of the surgical implant 100. For example, the openings 1071 and 1082 may be aligned to allow the fixation device 110 to traverse through the opening 1071 on the first side member 101, the opening 109, and the opening 1081. To achieve the alignment, the length "L1a" of the openings 1071, 1072, 1073 on the first side member 101 may be equal to the length "L2a" of the openings 1081, 1082, 1082 on the second side member 102, for example. In another embodiment, the lengths "L1a" may be different from, for example larger than, the length "L2a." In an embodiment, the surgical implant 100 may include at least one channel (shown in gray highlight) traversing through and dividing the cavity 109 and connecting the openings 107, 108, configured to guide a fixation device 100 from one opening 107 the other opening 108. The channels connecting the openings 107, 108 may be cylindrical or cube in shape.

Figure 3B:
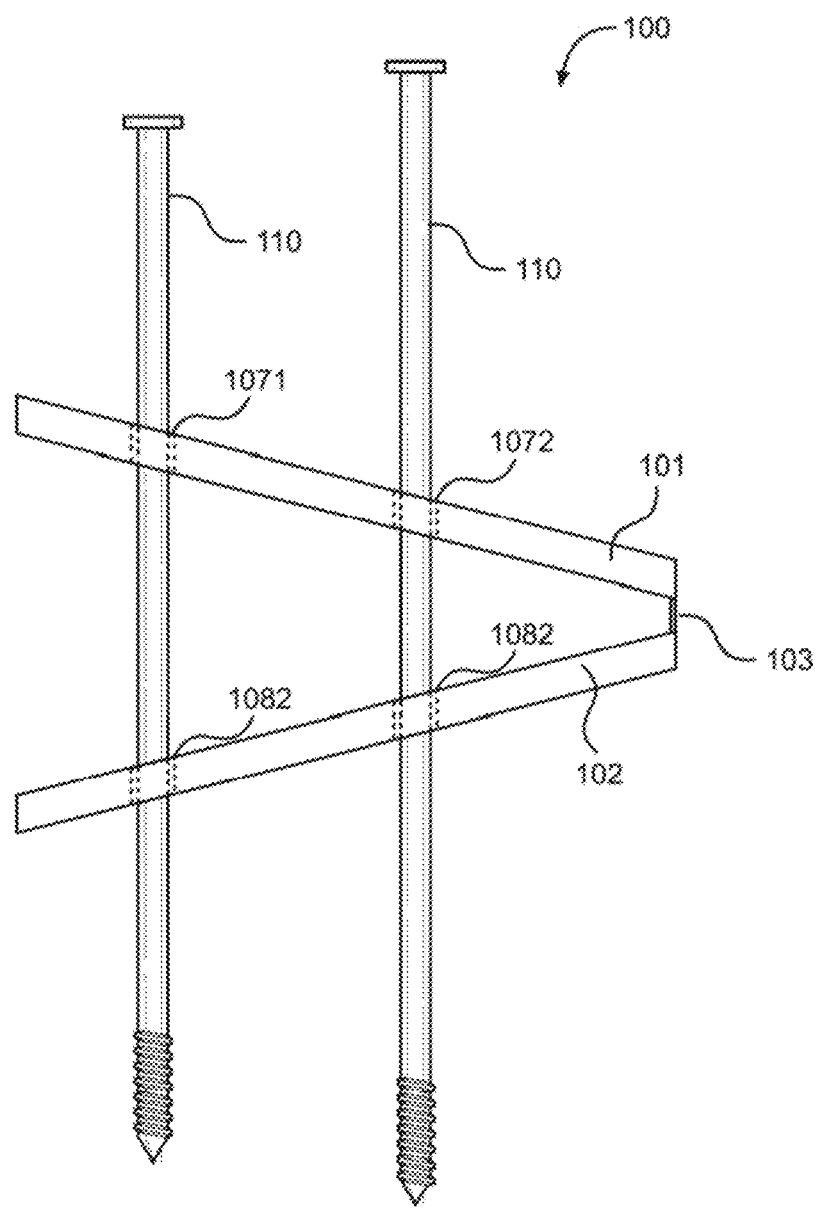
FIG. 3B is a top view of an embodiment surgical implant.

In an embodiment, FIG. 3B illustrates a top view of an embodiment surgical implant 100 and exemplary alignment between openings 1071, 1072, 1081, 1082 of the first and second side members 101, 102, respectively, and orientation of fixation devices 110. The first and second side members 101, 102 each include at least two aligned openings 1071, 1072, 1081, 1082, respectively. The opening 1071 is aligned with opening 1081 and the opening 1072 is aligned with opening 1082. Upon insertion of a first fixation device 110, it traverses the first opening 1071 and the second opening 1081. Upon insertion of the second fixation device 110, it traverses the first opening 1072 and the second opening 1082.

In embodiments, the first and second side members 101, 102 may be planar or non-planar. The first and second side members may have a convex shape, and/or each may include an inflexion point defining a first portion having a convex shape and a second portion having a concave shape. The first side members 101 may have different planar configurations from the second side member 102.

In embodiments, the top and bottom members 105, 106 may be planar or non-planar. The top and/or bottom members 105, 106 may have a convex shape. The top and/or bottom members 105, 106 may include an inflection point defining a first portion having a convex shape and a second portion having a concave shape.

Figure 4:
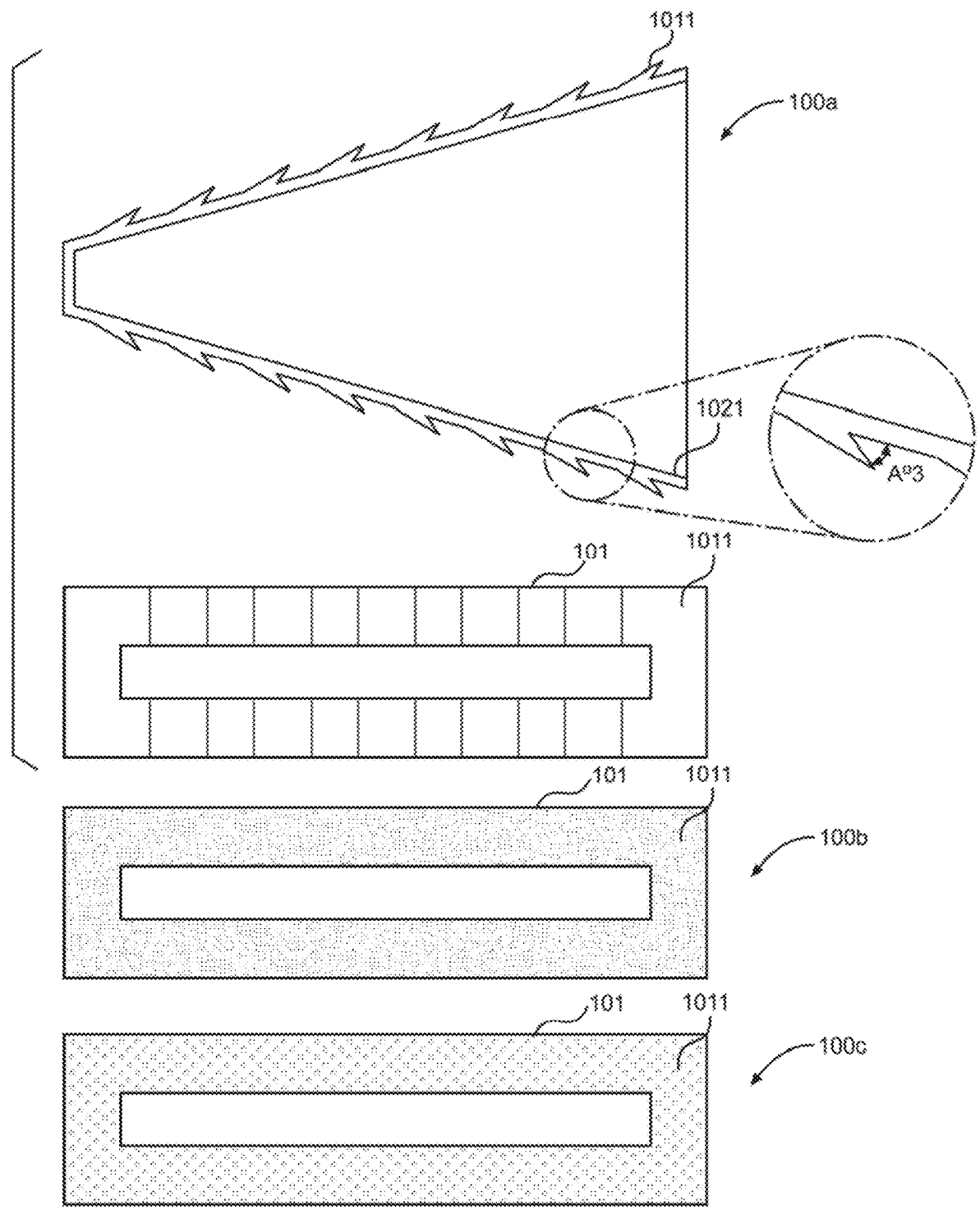
FIG. 4 is top and side views of an embodiment surgical implant.

In an embodiment, FIG. 4 illustrates a top and side views of a surgical implant 100 with textured finish. A textured finish can promote bone growth, fusion and adhesion with the surgical implant 100. As shown in the surgical implant 100a (top and side views), the first and second side member exterior surfaces 1011, 1021, which come in contact with the osseous tissue, may include ridges angled perpendicular to each of the first and second side members 101, 102 or angled $A°_3$ in a manner to point the ridges towards the proximal end of each of the first and second members 101, 102 to increase stability of the surgical implant 100a and prevent its slippage out of its position in the osseous tissue. Angle $A°_3$ may range from about 5° to about 89°.

In another embodiment as shown by the surgical implants 100b and 100c, each of the first and second side members 101, 102 may include a surface roughness or porous exterior surface 1011, 1021. The pores may extend partially into the surface of the member in which the pores are formed or may extend entirely through the thickness of first and second side members 101, 102 and be open to the at least one cavity 109 of the surgical implant 100.

In other embodiments, the top member 105 and bottom member 106 may also include textured surfaces. The textured surfaces may include a surface roughness or porous exterior surfaces. The pores may extend partially into the surface of the member in which the pores are formed or may extend entirely through the entire thickness of top and bottom members 105, 106 and be open to the at least one cavity 109 of the surgical implant 100.

The textured finish may extend across at least about 10% of the respective surface on which it is disposed. In embodiments, the textured finish extends across at least 75% of the respective surface and, in some embodiments, the textured finish extends across at least about 90% of the respective surface. The textured surface can improve adhesion between the surgical implant 100 and osseous tissue and/or facilitate bony integration with a biomaterial (e.g., bone growth material) to achieve bone fixation at the interface between the surgical implant 100 and the osseous tissue. The textured finish may be formed by subjecting a smooth surface to a surface roughening treatment, such as etching, sand blasting, etc. The textured finished may be structured and define, for example, a surface including substantially pyramidal protrusions where each pyramidal protrusion includes a plurality of protrusions or ridges disposed thereon to aid in securing the surgical implant 100 to osseous tissue. In particular, each pyramidal protrusion can include opposed first and second faces that face, respectively, distally and proximally, and opposed third and fourth faces that face, respectively, medially and laterally. For a detailed description of a surgical device having exemplary surface characteristics suitable for use with the surgical implant 100, reference can be made to U.S. Pat. No. 8,801,791 to Soo et al., the entire content of which is hereby incorporated by reference herein.

Variable dimensions, sizes, shapes and angles described above and which can be contemplated with respect to the surgical implant 100, such as the size and dimensions of openings on the first and second side members, allow for prefabrication and/or custom design of surgical implants 100 which can fit variable anatomical structures and variations. The variations can further facilitate insertion of a fixation device 110 through a first osseous tissue segment, the opening 107 on the first side member 101, the opening 108 on the second side member 102, and a second osseous tissue segment to secure the implant in place and impart compression pressure on the fracture to enhance bone formation and improve healing time. For a detailed description of a suitable computer implement method or system for designing 3D models reference can be made to U.S. Pat. Appl. No. 2014/0067106 to Prem Makeig, and U.S. Pat. Appl. No. 2013/0211531 to Steines et al., the entire content of each of which is hereby incorporated by reference herein.

The surgical implant 100 is formed from biocompatible material(s) including, but not limited to, metals and metal alloys, such as stainless steel, cobalt chrome, titanium, and titanium alloys, Dried Frozen Allograft, titanium cage combination with Dried Frozen Allograft, titanium cage with mesh overlying it, as well as polymers, such as polyether ether ketone ("PEEK"), or combinations of the aforementioned materials. The surgical implant 100 may be made using an additive manufacturing process, for example, by printing or foaming material(s) having sufficient strength, resiliency, and biocompatibility as needed or desired for a surgical procedure. For a detailed description of additive manufacturing processes suitable for forming the surgical implant 100, reference can be made to U.S. Pat. Appl. Pub. No. 2016/0213485 to Schaufler et al., U.S. Pat. Appl. Pub. No. 2016/0213487 to Wilson et al., U.S. Pat. Appl. Pub. No. 2016/0213488 to Moore et al., and U.S. Pat. No. 9,987,051 to Nunley et al., the entire content of each of which is hereby incorporated by reference herein.

Figure 5A:
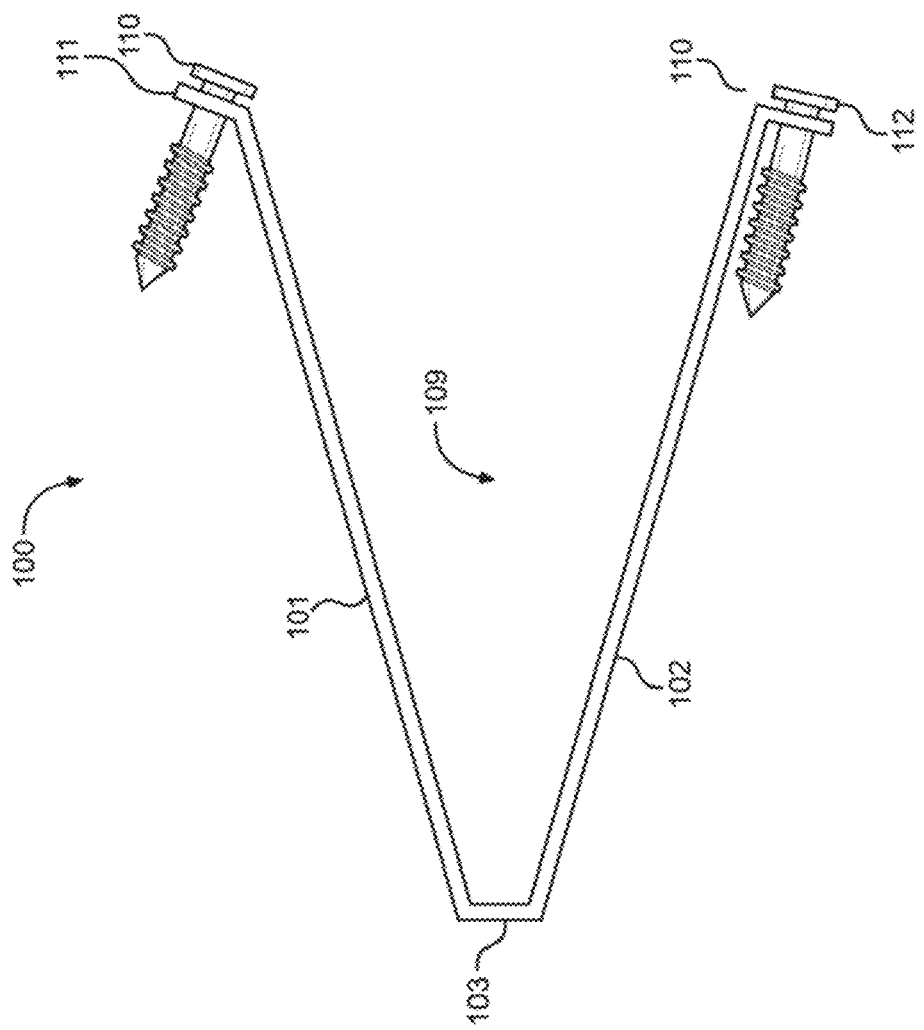
FIG. 5A is a top view of an embodiment surgical implant.
Figure 5B:
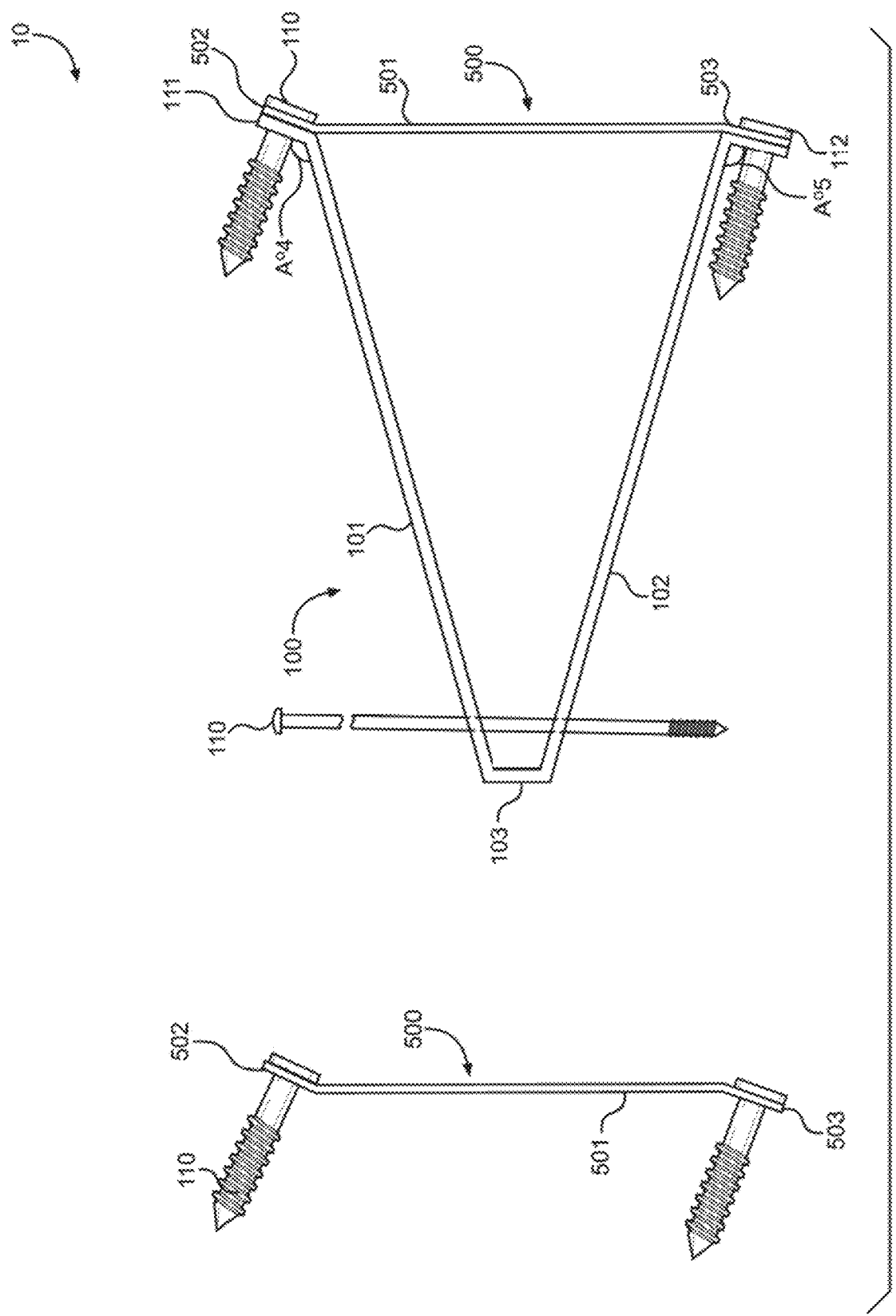
FIG. 5B is a top view of a surgical implant system or assembly and a side view of an embodiment bone plate.

In an embodiment, FIG. 5A illustrates the surgical implant 100 configured to attach to adjacent osseous tissue using fixation devices 110. The surgical implant may include at least a first side member 101, a second side member 102 and a distal member 103. The first side members 101, at its proximal end 101a, includes a first curved proximal portion 111, and, the second side member 102, at its proximal end 102a, includes a second curved proximal portion 112. The first curved proximal portion 111 forms an angle $A°_4$ with the first side member 101 (FIG. 5B). The second curved proximal portion 112 forms an angle $A°_5$ with the second side member 102 (FIG. 5B). The curve of the first curved proximal portion 111 may be the reverse of the curve of the second curved proximal portion 112 such that the radius of curvature of the first curved proximal portion 111 is opposite the radius of curvature of the second curved proximal portion 112. The curvature of each of the first and second curved proximal portion 111, 112 can mimic the curvature of osseous tissue against which the surgical implant 100 is to be placed such that the first and second curved proximal portions 111, 112 conform to the shape of the osseous tissue. In embodiments, one of the first and second curved proximal portions 111, 112 may be curved and the other flat. Using the first and second curved proximal portion 111, 112, the surgical implant can be secured to the osseous tissue.

In an embodiment system, FIG. 5B illustrate a surgical implant system or assembly 10 including the surgical implant 100 configured to attach to a bone plate 500 and a side view of an embodiment bone plate and fixation devices 110. The surgical implant 100 and the bone plate 500 may be used to secure the surgical implant 100 to the osseous tissue and to create a cavity 109 inside the implant 100.

In embodiments, a bone plate 500 may include an elongate body 501 extending between a first end portion 502 and a second end portion 503. The elongate body 501 may be flat (i.e., planar), and the first and second end portions 502, 503 may be curved. The curve of the first end portion 502 may be the reverse of the curve of the second end portion 503, such that the radius of curvature of the first end portion 502 is opposite the radius of curvature of the second end portion 503. The curvature of each of the first and second end portions 502, 503 can mimic the curvature of the surgical implant first and second curved proximal potions 111, 112 or the osseous tissue against which the bone plate 500 is to be positioned. In embodiments, the bone plate may be positioned adjacent to the proximal member 104 such that the first and second end portions 502, 503 conform to the shape of first and second curved proximal potions 111, 112. In embodiments, one of the first or second end portions 502, 503 may be curved and the other flat.

In embodiments, the bone plate 500 may be placed adjacent to the proximal member 104 of the surgical implant 100 and the attachment screw may be inserted through a central opening of the bone plate 500 and into the surgical implant 100 to secure the bone plate 500 thereto. The orientation of the bone plate 500 relative to the surgical implant 100 may be adjusted prior to tightening the attachment screw to, for example, ensure that the first and second end portions 502, 503 of the bone plate 500 are contoured to the outer surface of the pelvic bone. For a detailed description of securing a bone plate 500 to a surgical bone plate using an attachment screw inserted through the center opening of the bone plate 500 and into the surgical implant 100, reference can be made to U.S. Pat. Appl. Pub. No. 2019/0038329A1 to Poelstra et al., the entire content of each of which is hereby incorporated by reference herein.

Figure 6A:
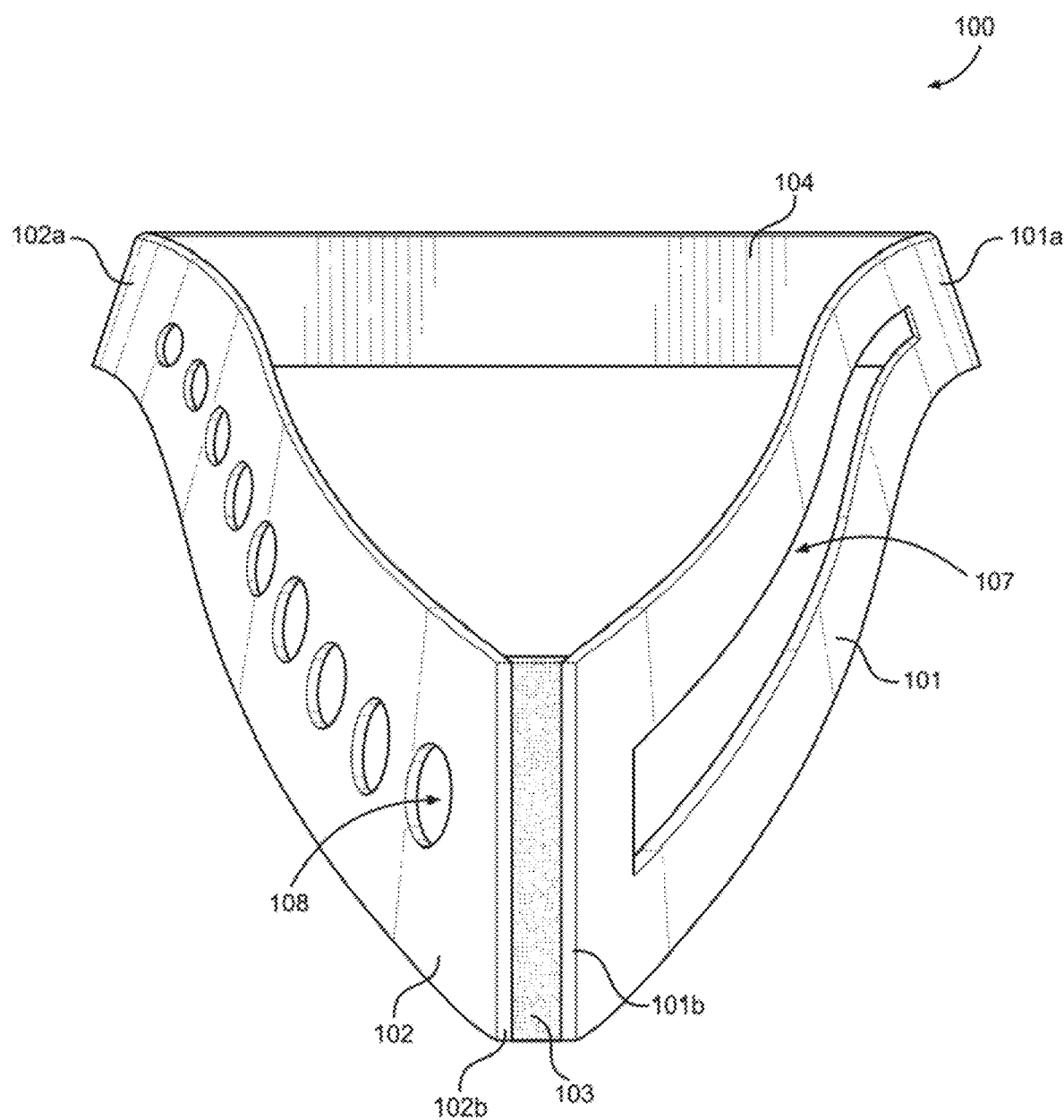
FIG. 6A is a 3-dimensional view of an embodiment surgical implant.
Figure 6B:
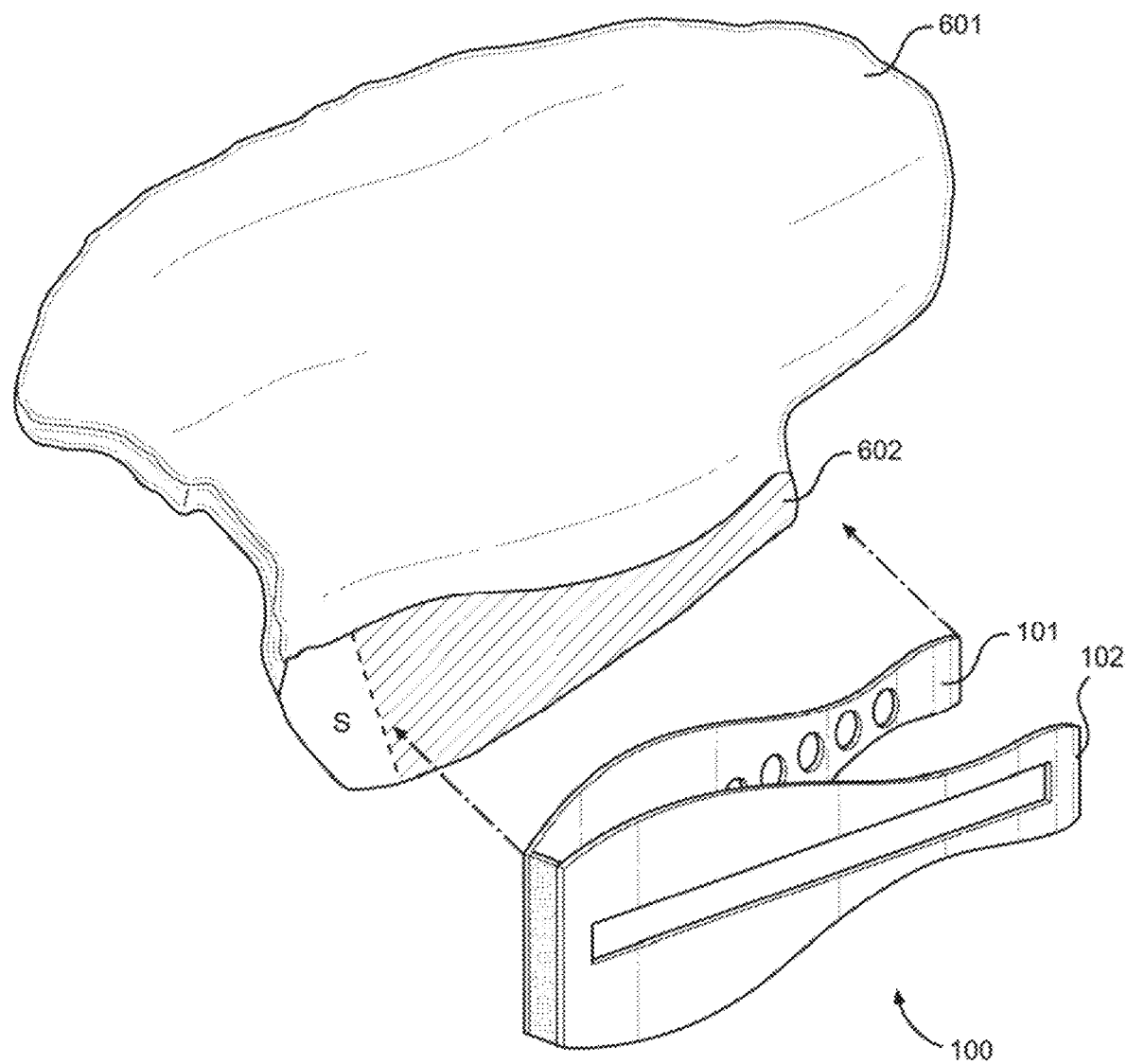
FIG. 6B is a 3-dimensional view of an embodiment surgical implant and pelvic bone.
Figure 6C:
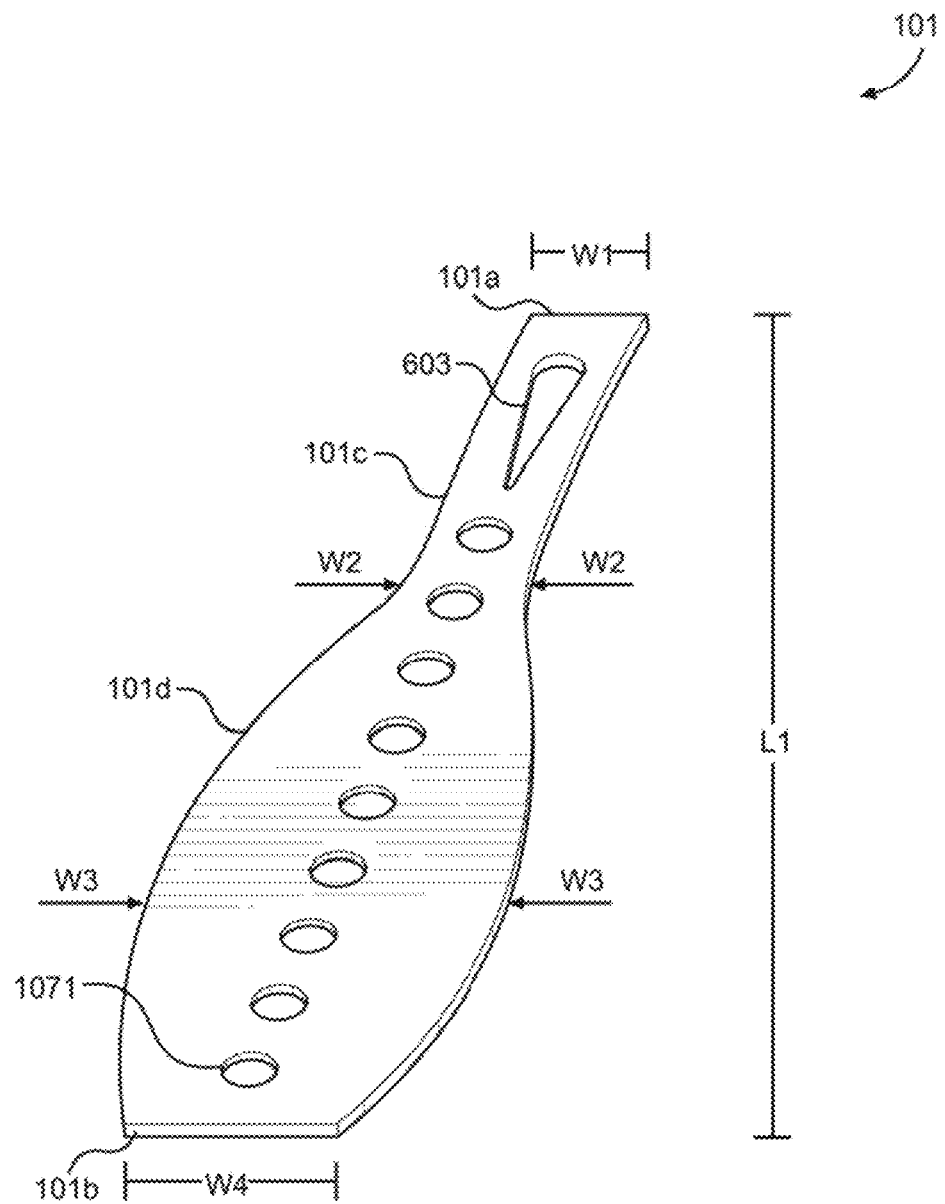
FIG. 6C is a side view of an embodiment surgical implant.
Figure 12:
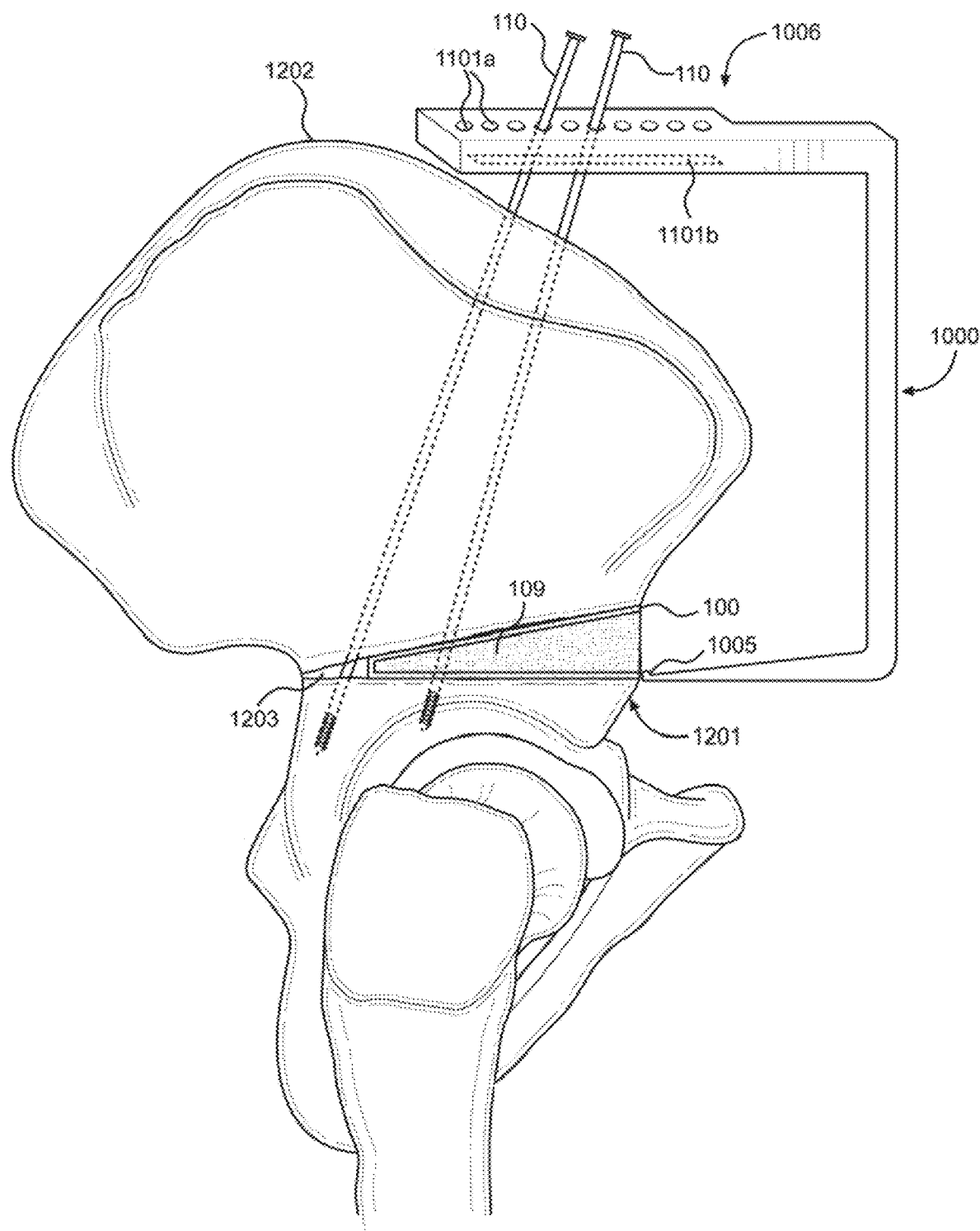
FIG. 12 is a side view of a pelvic bone, illustrating the surgical implant of FIG. 1A positioned in the pelvic bone and further illustrating the surgical implant guiding system of FIG. 10.

The first and side members 101, 102 of the surgical implant 100 may be include the shape of the bone adjacent to which they will be placed. FIGS. 6A-6C illustrate the shape of the first and second side members 101, 102, in embodiments where the surgical implant 100 is used to correct or adjust anatomical structure or balance by insertion of the surgical implant 100 in the pelvis bone 601. As illustrated in FIGS. 6A-6B, the first and second side members 101, 102 may have contoured shapes which exactly matches the cross-section of the pelvic bone contours 602, when the bone is cut at or about the anterior inferior iliac spine (AIIS). Matching of the shape of the first and second side members 101, 102 of the surgical implant 100 allows for improved stability and congruity between the surgical implant 100 and the pelvic bone. FIG. 6B further illustrates an empty space "S" at the distal end of a trapezoid shaped surgical implant 100. As shown in FIG. 12, a second fixation device 110 may be inserted through the ilium, traversing through a space "S" and continue through the ischium to prevent the surgical implant 100 to move distally, stabilize the fracture and promote efficient healing by applying compression forces.

In an embodiment, FIG. 6C illustrates a side view of the surgical implant 100 showing variable widths along the length "L1" of the first side member 101. Although FIG. 6C illustrates the contours and components of the first side member 101, it is contemplated that the second side member 102 can mirror the same contour and may include the same components as discussed with respect to the first side member 101. For example, the first side member 101 includes a first width "W1" extending across the proximal member 104 at the proximal end 101a of the first side member 101, a second width "W2" extending across a first section 101c of the first side member 101 disposed adjacent to the proximal end 101a and that includes at least a first channel opening 603 configured to guide a fixation device 110 (not shown), a third width "W3" extending across a second section 101d of the first side member 101 disposed adjacent to the distal end 101b of the first side member 101, and a fourth width "W4" extending across the distal member 103 of the surgical implant 100 at the distal end 101b of the first side member 101.

The first width "W1" at the proximal end 101a of the first side member 101 may be wider than the fourth width "W4" at the distal end 101b of the first side member 101, and/or the first side member 101 may be widest at the second width "W2." For example, as shown in FIG. 6C, the width of the first side member 101 may increase from the first width "W1" to the second width "W2," taper to the third width "W3," and taper further to the fourth width "W4." It should be understood that the first and second side members 101, 102 of the surgical implant 100 may have any suitable width or variable width profile. The first width "W1" of the first or second side members 101, 102 of the surgical implant 100 may range from about 5 mm to about 50 mm. In embodiments, the first width "W1" ranges from about 20 mm to about 30 mm and, in some embodiments, the first width "W1" is about 25 mm. The second width "W2" of first or second side members 101, 102 of the surgical implant 100 may range from about 15 mm to about 45 mm. In embodiments, the second width " W2 " ranges from about 20 mm to about 40 mm and, in some embodiments, the second width " W2" is about 35 mm. The third width "W3" of the surgical implant 100 may range from about 10 mm to about 40 mm. In embodiments, the third width "W3" ranges from about 12 mm to about 35 mm and, in some embodiments, the third width "W3" is about 25 mm. The fourth width "W4" of the first or second side members 101, 102 of the surgical implant 100 may range from about 2 mm to about 22 mm. In embodiments, the fourth width "W4" ranges from about 7 mm to about 17 mm and, in some embodiments, the fourth width "W4" is about 12 mm.

As illustrated in FIGS. 7A-7C, the surgical implant 100 may include at least two channels 603a, 603b connecting at least one opening 603c positioned on the proximal member 104 to at least a second opening 6031, 6032 positioned on each of the first and second side members 101, 102, respectively. The channels 603a, 603b are configured to guide fixation devices 110 diagonally through the surgical implant 100 from the proximal member 104 towards openings 6031, 6032 positioned on each of the first and second members 101, 102, to reach and impale adjacent osseous tissue. The use of the channels 603a, 603b provide additional manners for securing the surgical implant 100 to the osseous tissue using fixation devices 110.

Figure 8A:
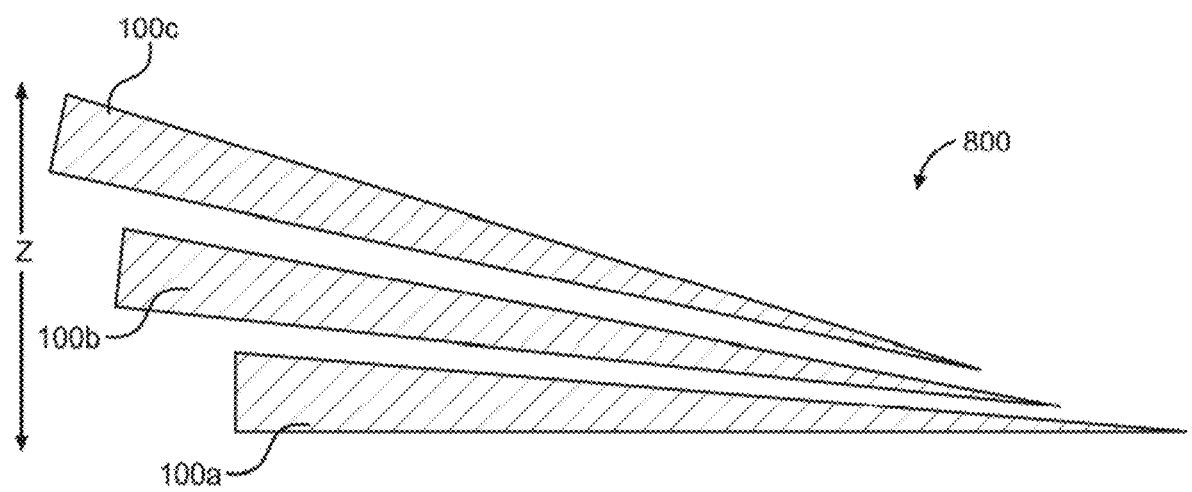
FIG. 8A is a side view of an embodiment stackable surgical implant system.
Figure 8B:
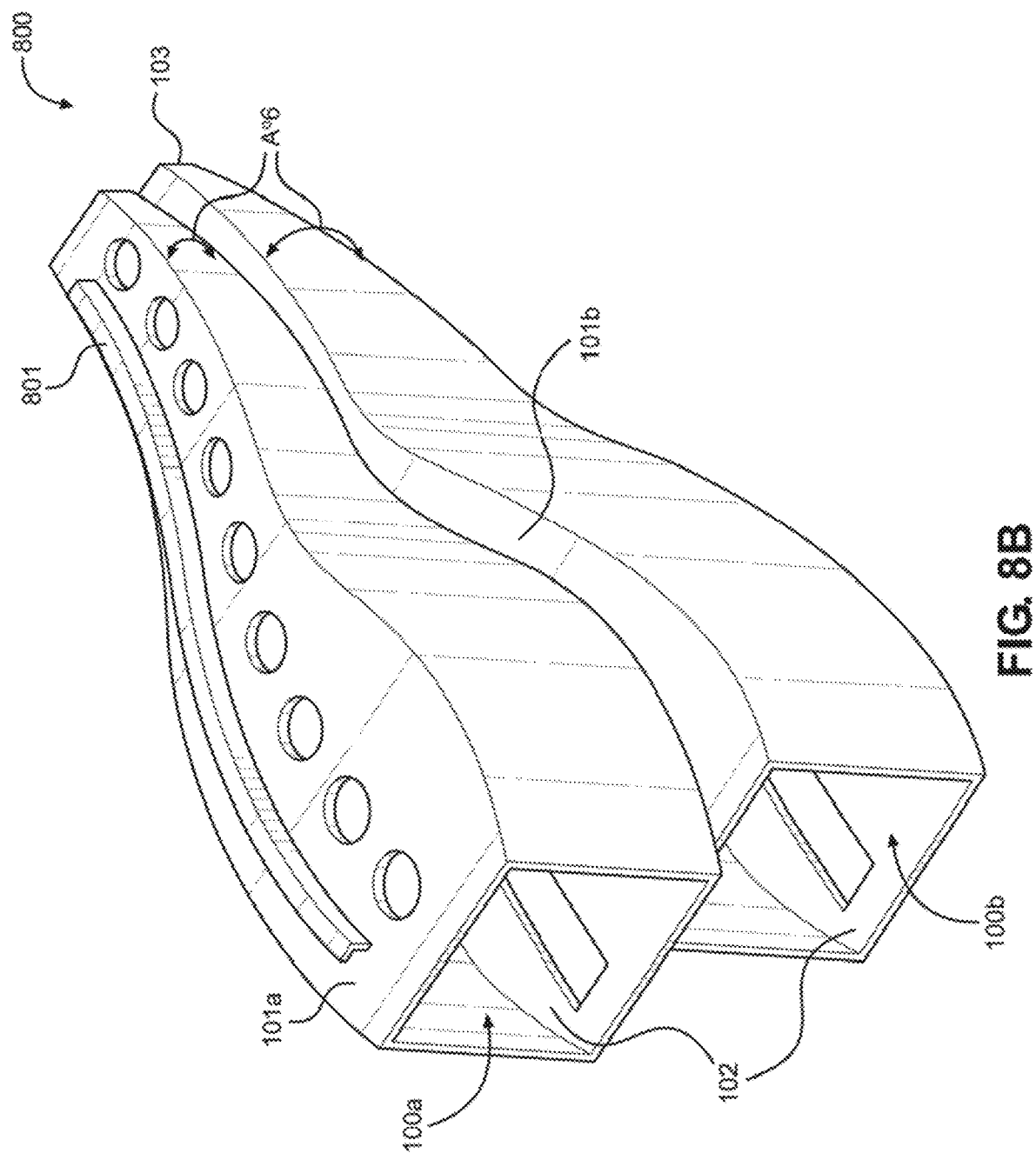
FIG. 8B is a 3-dimensional view of an embodiment stackable surgical implant system.

In an embodiment, FIGS. 8A-8B illustrate stackable surgical implant systems 800. A stackable surgical implant system 800 may include at least two surgical implants 100 configured to attach to each other vertically and may be used to gradually increase the angle of anatomical correction on a subject by stacking variable angled surgical implants 100 to the stack. FIG. 8A illustrates a stackable surgical implant system 800 comprising three surgical implants 100a, 100b, 100c each having equal dimensions and adding identical vertical correction along a "Z" axis.

In an embodiment, FIG. 8B illustrates a stackable surgical implant system 800 comprising two surgical implants 100a, 100b with variable contoured first and second side members 101, 102. Each of the surgical implants 100a, 100b may be connected to each other using connection means 801. Connection means 801 may include magnetic connections, railings, pins or pegs from one implant inserted into bores on another implant, connecting protruding surface of one implant to the recessed surface of the other, or snap and click mechanisms. The connection means 801 may further include connecting surgical implants 100 chemically, or by use of adhesive material. The stacked implants 100 may remain loosely associated through their complementary protrusions and recesses or be separated and reconnected with each other, repeatedly. The connection means 801 may further include connecting surgical implants 100 to one another using a fixation device 110 traversing through the first and second side openings 107, 108 of each of the surgical implants 100. In an embodiment, the textured external surfaces of adjacent first and second members 101, 102 may also inhibit shifting of stacked implants and may define a connection means 801. For a detailed description of connecting stackable surgical implants 100 and various connecting means 801, reference can be made to U.S. Pat. Appl. Pub. No. 2006/0015184 to Winterbottom et al., U.S. Pat. No. 6,123,731 to Boyce et al., U.S. Pat. No. 6,478,825 to Winterbottom et al. and U.S. Pat. No. 9,345,589 to John Stark, the entire content of each of which is hereby incorporated by reference herein.

In an embodiment, FIG. 8B illustrates a stackable surgical implant system 800 comprising at least two surgical implants 100a, 100b. Each surgical implant 100a, 100b includes a railing to connect with the other implant in a manner to align the openings 107, 108 of each of the surgical implants 100, allowing fixation devices 110 to traverse through the multiple surgical implants 100a, 100b. Each surgical implant 100a, 100b may define an angle $A°_6$ between the first and second side members 101, 102. The angle $A°_6$ for each surgical implant 100a, 100b may be the same or different and its value may depend on the total degree of correction required at the anatomical structure.

Figure 9B:
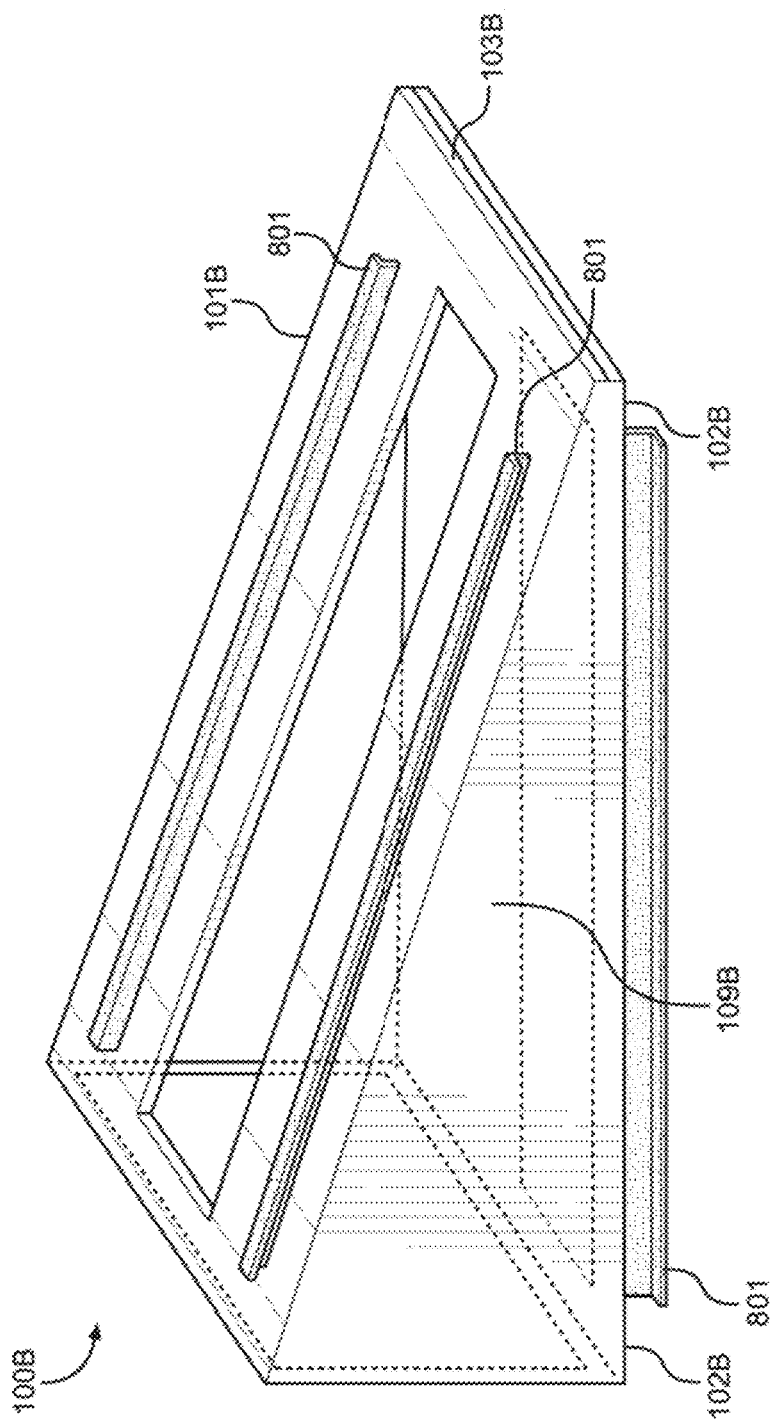
Figure 9C:
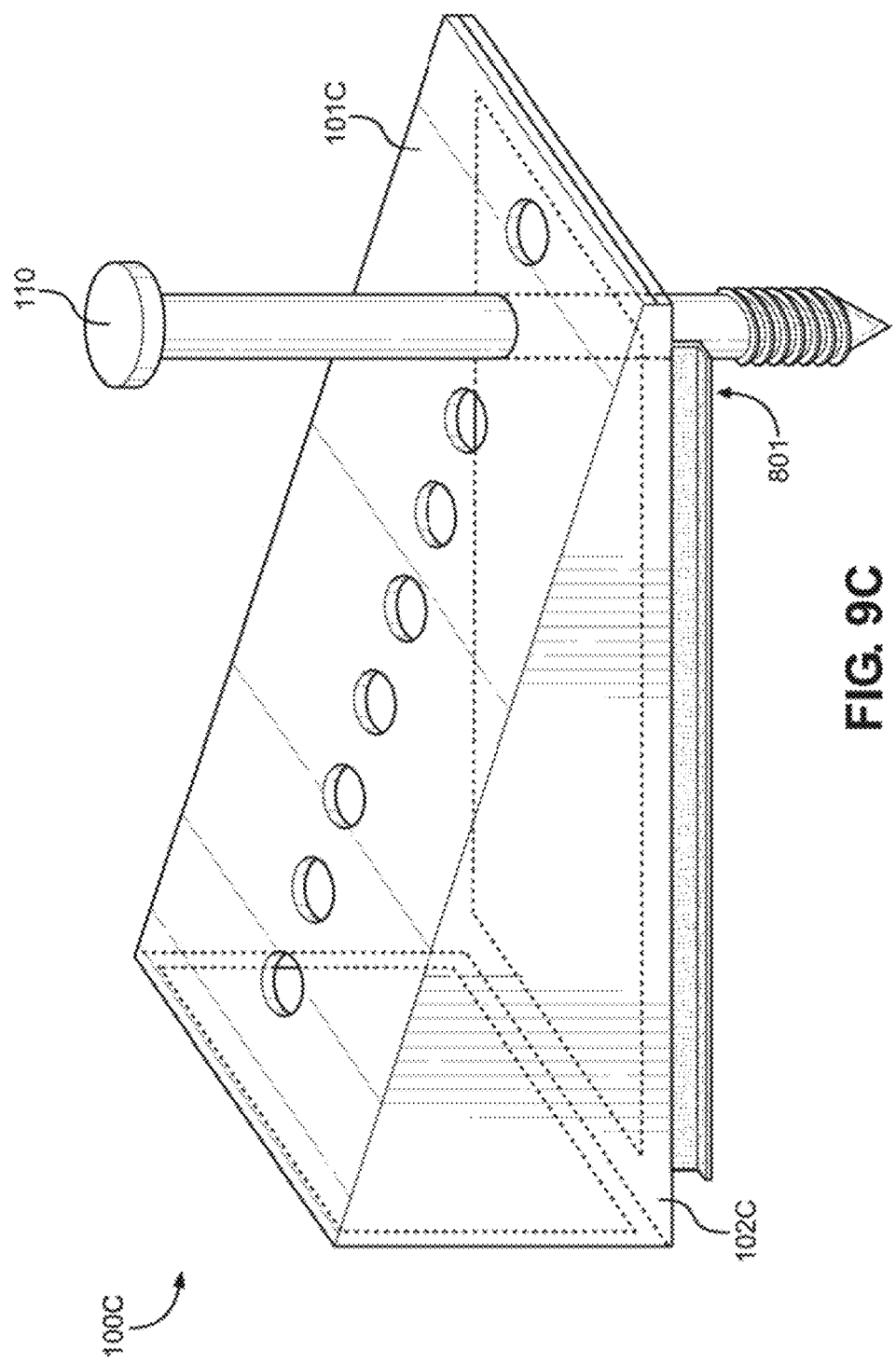

In an embodiment, FIGS. 9A-9C illustrate components of a stackable surgical implant 800 comprising three surgical implants 100A, 100B, 100C. Each of the surgical implants 100A, 100B, 100C are shown separately. FIG. 9A illustrates a base surgical implant 100A representing the lowest stackable implant in a series of three implants which includes connection means 801 on the first side member 101A, only. Because the base surgical implant 100A is positioned at the bottom of the stack, connection means 801 may not be present on the second side member 102A which comes into contact with osseous tissue. Accordingly, the base surgical implant 100A only includes connection means 801, such as railings, on the first side member 101A for connecting or interlocking to the surgical implant 100B. As the surgical implant 100 stacks the first side member 101A is positioned adjacent to the second side member 102B of the surgical implant 100B, for example. FIG. 9B illustrates the middle positioned stackable surgical implant 100B which includes connection means 801 on the first and second side member 101B, 102B to attach to top and bottom positioned surgical implants 100A, 100C. FIG. 9C illustrates the top positioned stackable surgical implant 100C which includes connection means 801 on the second side member 102C, only. Because the surgical implant 100C is positioned at the bottom of the stack, connection means 801 may not be present on the first side member 101C which comes into contact with osseous tissue. Accordingly, the top surgical implant 100C includes connection means 801, such as railings, on the second side member 102C for connecting or interlocking to the surgical implant 100B, the second side member 102C is positioned adjacent to the first side member 101B of the surgical implant 100B, for example.

Figure 10:
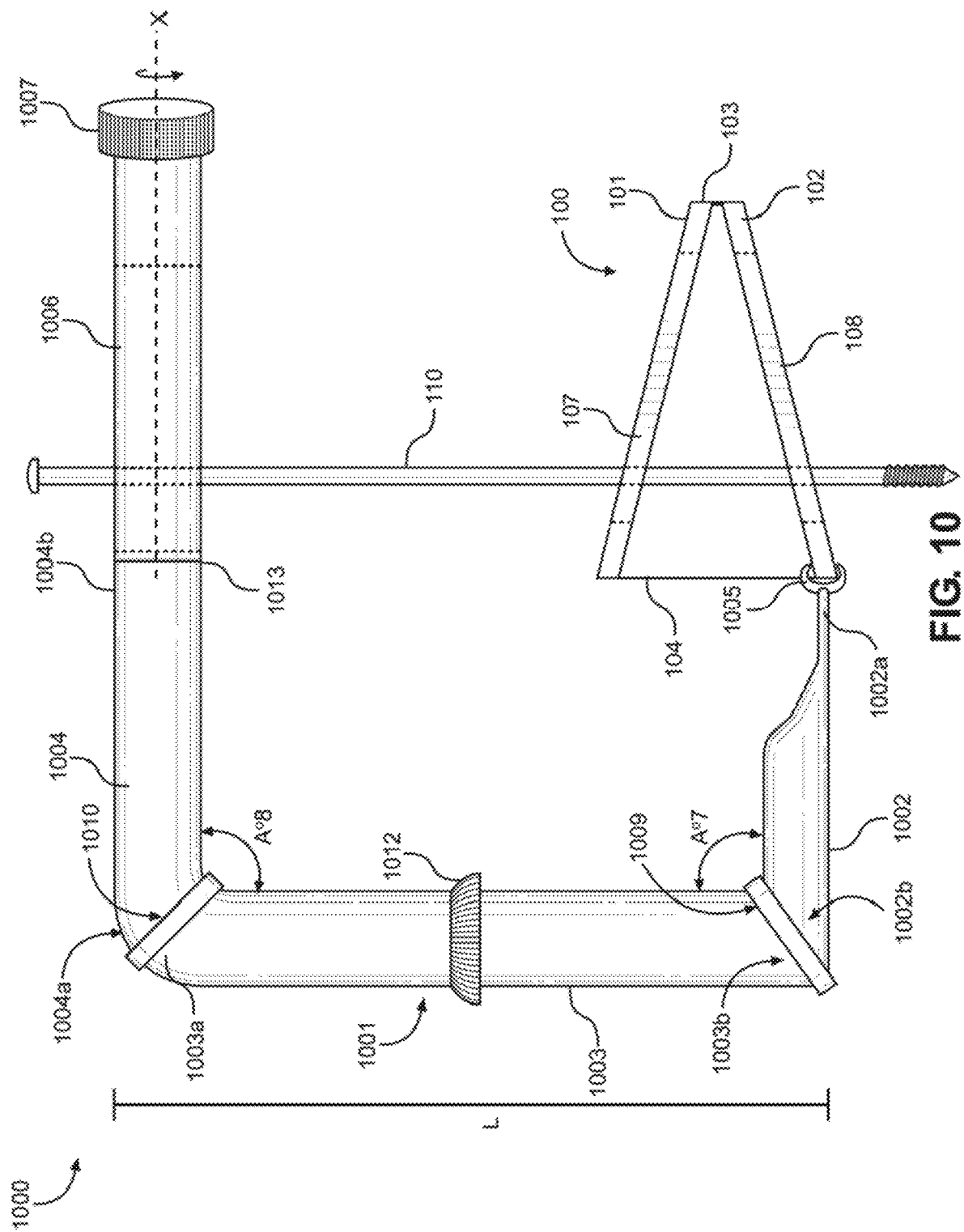
FIG. 10 is a side view of an embodiment surgical implant guiding system.

In an embodiment, FIG. 10 illustrates a side view of a surgical implant guiding system 1000 comprising a surgical implant 100, a surgical implant guide 1001, an attachment mechanism 1005, a fixation device guide 1006, and at least one fixation device 110. The attachment mechanism 1005 and fixation device guide 1006 are each attached to opposite ends of the surgical implant guide 1001. The attachment mechanism 1005 is configured to removably attached to the surgical implant 100. The surgical implant guiding system 1000 allows for accurate insertion, installation and fixation of the surgical implant 100 in an anatomical location, such as in the pelvic bone.

The surgical implant guide 1001 may be formed from metals and metal alloys, such as stainless steel, cobalt chrome, titanium, and titanium alloys, as well as polymers, such as polyether ether ketone ("PEEK"), or combinations of the aforementioned materials. The surgical implant guide 1001 may be made using an additive manufacturing process, for example, by printing or foaming material(s) having sufficient strength, and resiliency as needed or desired for a surgical procedure. For a detailed description of additive manufacturing processes suitable for forming the surgical implant 100, reference can be made to U.S. Pat. Appl. Pub. No. 2016/0213485 to Schaufler et al., U.S. Pat. Appl. Pub. No. 2016/0213487 to Wilson et al., U.S. Pat. Appl. Pub. No. 2016/0213488 to Moore et al., and U.S. Pat. No. 9,987,051 to Nunley et al., the entire content of each of which is hereby incorporated by reference herein.

In embodiments, the surgical implant guide 1001 includes at least a first end portion 1002, a middle portion 1003 and a second end portion 1004, the first end, middle and second end portions 1002, 1003, 1004 may interconnect to dispose the first end portion 1002 in opposed, spaced relation relative to the second end portion 1004. The first end portion 1002 includes a proximal end 1002a and distal end 1002b. At the distal end 1002a, the first end portion 1002 interconnects with the attachment mechanism 1005. At the proximal end 1002b, the first end portion 1002 interconnects with the middle portion 1003 at an angle $A°_7$. The second end portion 1004 includes a proximal end 1004a and a distal end 1004b. At the proximal end 1004a, the second end portion 1004 interconnects with the middle portion 1003 at an angle $A°_8$. At the distal end 1004b, the second end portion 1004 interconnects with the fixation device guide 1006. The middle portion 1003 includes a top end 1003a and a bottom end 1003b. At the top end 1003a, the middle portion 1003 interconnects with the proximal end 1004a of the second end portion 1004 at the angle $A°_8$. At the bottom end 1003b, the middle portion 1003 interconnects with the proximal end 1002b of the first end portion 1002 at the angle $A°7$. In embodiments, adjustable joints 1009, 1010 are contemplated at locations where the first and second end portions 1002, 1004 interconnect to the middle potion 1003 to allow the user to achieve different angles $A°_7$, $A°_8$ during surgical procedures. The middle portion 1003 may further include an adjustable knob 1012 configured to adjust the length "L" of the middle portion 1003. The adjustable knob 1012 may allow the user to adjust the height of the surgical implant guide 1001 based upon the anatomical variations of a patient, such as length of the pelvic bone.

In embodiments, the first end portion 1002 interconnects with an attachment mechanism 1005. The attachment mechanism 1005 may removably connect to the surgical implant 100 and may facilitate insertion of the surgical implant 100 into an anatomical position, such as in the pelvic bone, and adjusting the positioning of the surgical implant 100 when in the anatomical position, aligning the openings 107, 108 of the surgical implant 100 with the openings of the fixation device guide 1006. For example, the attachment mechanism 1005 may include clamps, screws, railings, pins and bores, removable adhesive, or breakable plastic tongue. The attachment mechanism 1005 may removably connect to the surgical implant 100 only at the second side member 102 (as illustrated) or at the first and second side members 101, 102. In other embodiments, the attachment mechanism 1005 may removably connect to the surgical implant 100 at other components of the surgical implant 100, such as to the distal or proximal members 103, 104. In embodiments, the attachment mechanism 1005 further comprises a swivel at the point of connection of the implant that allows it to rotate in the medial and lateral plane 30° in either direction to facilitate alignment for fixation device insertion.

At its distal end 1004b, the second end portion 1004 interconnects to the fixation device guide 1006. In an embodiment, the fixation device guide 1006 may interconnect to the second end portion 1004 through rotatable joint 1013 configured to allow the fixation device guide 1006 to rotate around its axis "X" to assist in orienting the fixation device guide 1006 openings with the openings 107, 108 of the surgical implant 100. The rotatable fixation device guide 1006 may include a knob 1007 at its free end to allow the user in rotating the fixation device guide 1006 around axis "X". In an embodiment, the rotating joint 1013 may include hard clicks to stop the rotation motion at narrow rotation angles and intervals. In another embodiment, the rotation joint 1013 may provide rotational resistance requiring high rotational torque to be applied by the user to rotate the fixation guide device 1006. In another embodiment, the rotatable joint 1013 may include lock and release modes to allow rotation of the fixation device guide 1006 in the release mode and disallow rotation when in the lock position. Rotational resistance, hard clicks, lock and release modes and other adjustable mechanism are contemplated to allow the fixation device guide 1006 to provide stable angles of insertion of fixation devices 110. In other embodiments, the fixation device guide 1006 may fixedly interconnect to the second end portion 1004. For example, the fixation device guide 1006 may be pre-fabricated with fixation guide openings oriented at variable angles as described therein and/or personalized to a subject's anatomical structure.

The first end portion 1002, middle portion 1003 and second end portion 1004 interconnect to dispose the surgical implant 100 in opposite, spaced relation relative to the fixation device guide 1006. In this oppose, spaced relation, the fixation device guide 1006 facilitates insertion of fixation devices 110 into the pelvic bone and through the openings 107, 108 of the surgical implant 100. Angles A°$_7$, A°$_8$ are configured to guide the fixation devices 110 from the fixation device guide 1006 to the surgical implant 100 and may each range from about 5° to about 179°, more particularly from about 45° to about 135°.

Figure 11B:
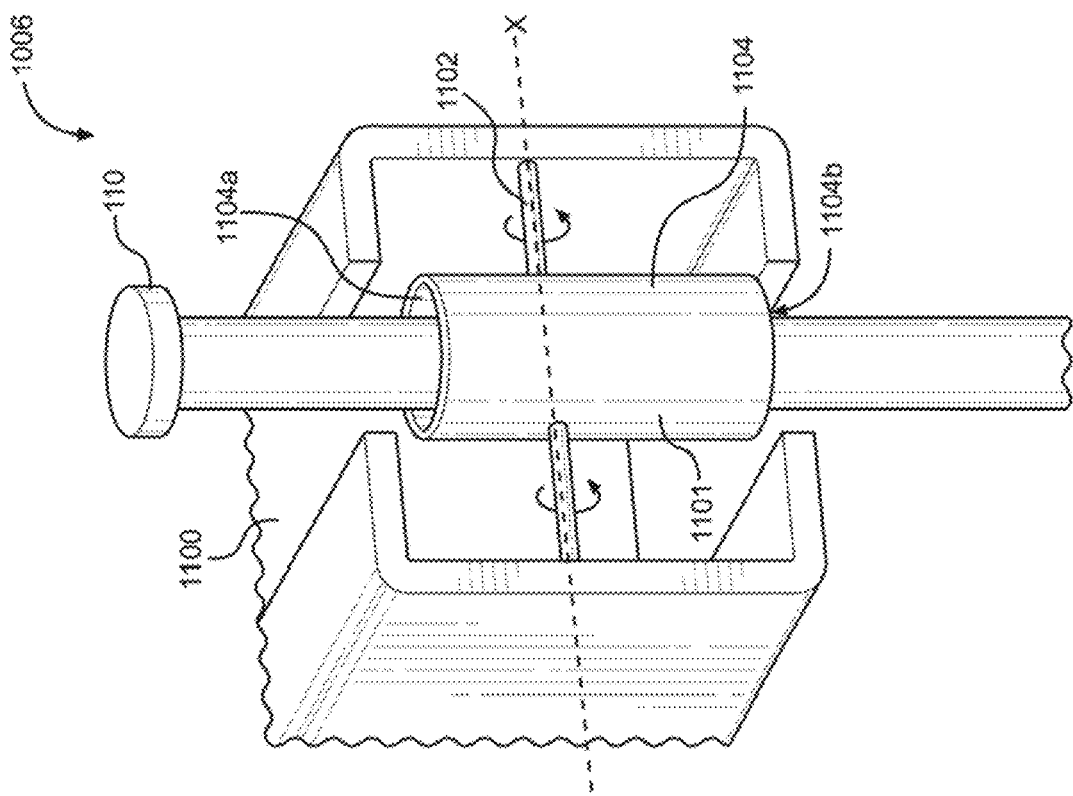
FIG. 11B is a 3-dimensional view of a portion of an embodiment fixation device guide.
Figure 11A:
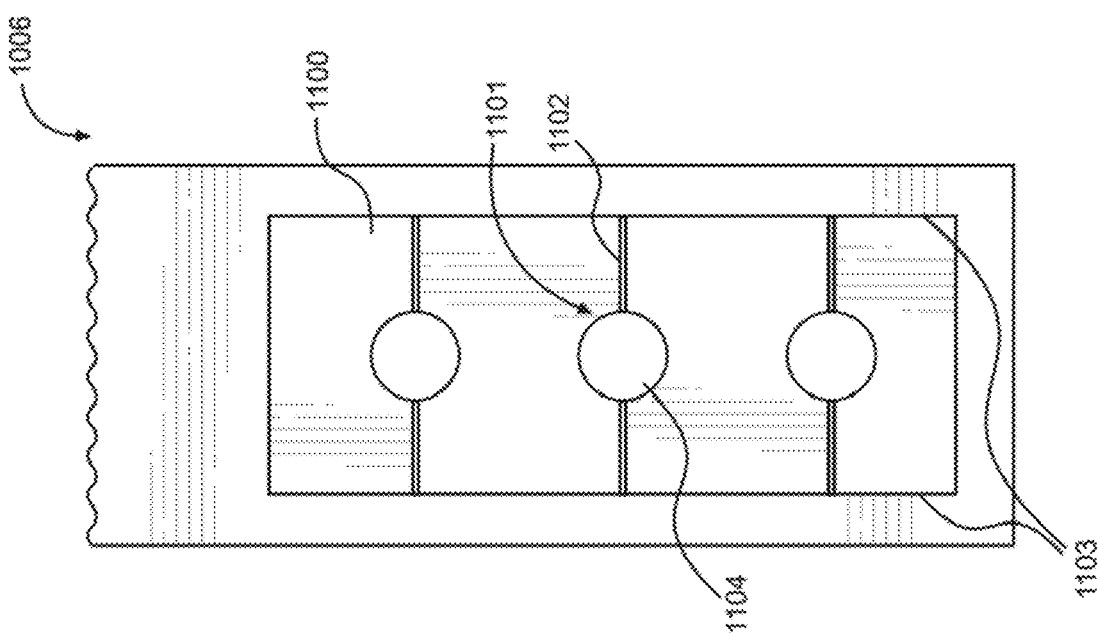
FIG. 11A is a top view of an embodiment fixation device guide.

FIGS. 11A-11F illustrate alternative embodiments of fixation device guide 1006. Fixation device guide 1006 may be used to pass and guide fixation devices 110 such as wires, drills, bone taps and bone screws through portions of the skeletal anatomy, such as the pelvis, that are outside the margins of an osteotomy and further through the surgical implant 100. FIGS. 11A-11B illustrate the fixation device guide 1006 including at least one adjustable fixation device holder 1101. FIG. 11A illustrates a top view of an embodiment fixation device guide 1006 including an opening 1100, the opening 1100 extending the entire thickness of the fixation device 1006 and comprising side walls 1103, and at least one fixation device holder 1101. The at least one fixation device holder 1101 comprising a housing 1104 with at least two openings 1104a, 1104b at each end, the housing 1104 rotatably connected to the side walls 1103 of the fixation device opening 1100 by at least two pins 1102. In an embodiment, the housing may be tubular.

FIG. 11B illustrates a 3-dimensional view of an embodiment fixation device guide 1006 with the at least one rotatable fixation device holders 1101. The at least one fixation device holder may comprise two openings 1104a and 1104b at each end configured to allow traversal of the fixation device 110 through the fixation device holder 1101 and therefore through the fixation device guide 1006. The pins 1102 are configured to allow rotation of the at least one fixation device holder 1104 around an axis "X". The rotation of the at least one fixation device holder 1104 along axis "X" allows adjustment of the angle of a fixation device 110 prior to insertion into osseous tissue, the angle adjustment is important to ensure the fixation device 110 would traverse the openings 107, 108 of the surgical implant 100 when it reaches the surgical implant 100 disposed in opposed, spaced relation relative to the fixation device guide 1006. In an embodiment, the pins 1102 may be fixedly attached to the fixation device holder 1104, but rotatably connected to the side walls 1103. The connection between the pin and the side walls 1103 of the fixation device opening 1100 may include hard clicks or lock and release mechanisms to allow the fixation device holder 1104 to reach and remain at a rotational position.

Figure 11C:
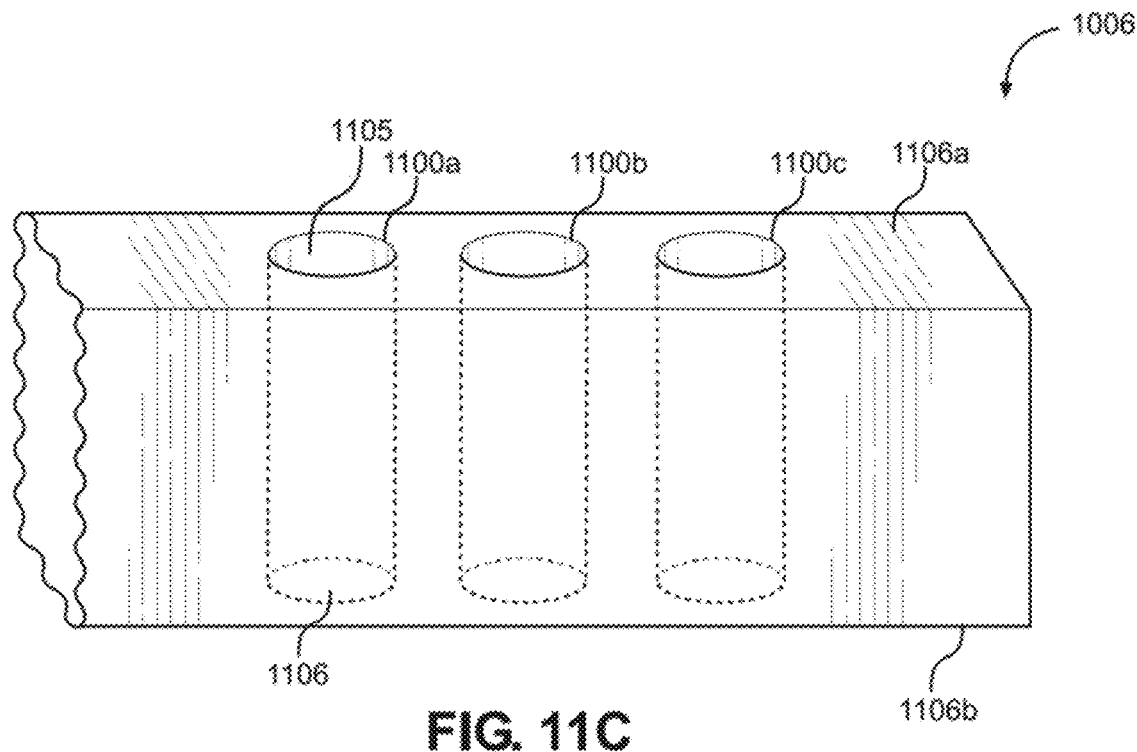
FIG. 11C is a 3-dimensional view of a portion of an embodiment fixation device guide.
Figure 11D:
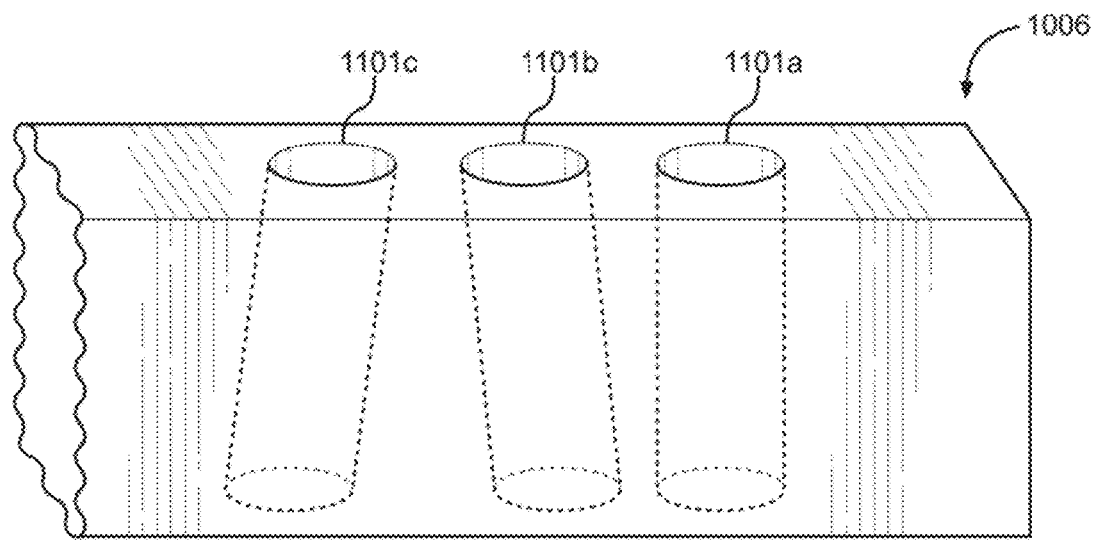
FIGS. 11D-11E are 3-dimensional views of portions of an embodiment fixation device guide.
Figure 11E:
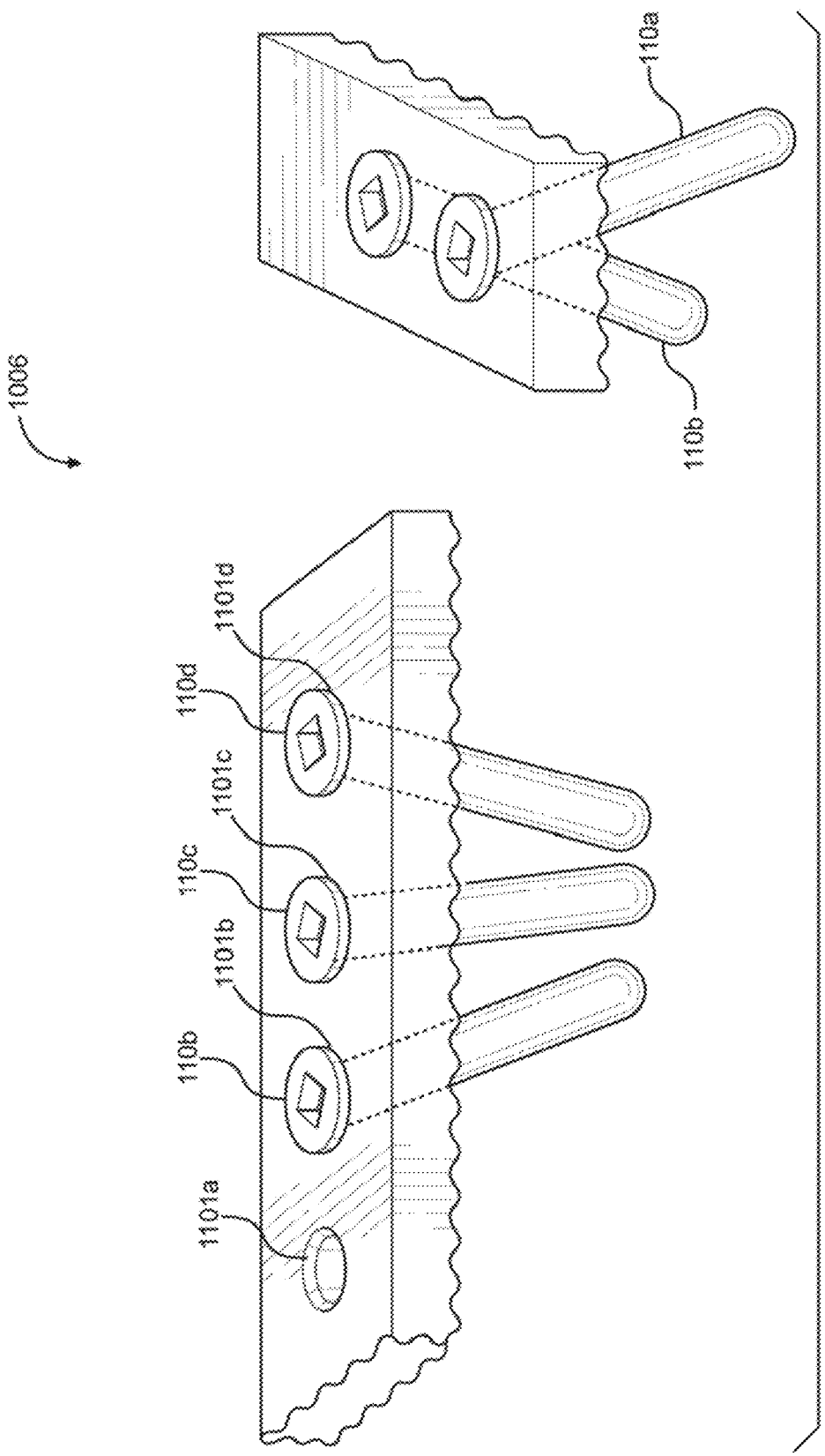

In an embodiment, FIG. 11C illustrates a 3-dimentional view of a portion of an embodiment fixation device guide 1006. The fixation device guide 1006 may include at least one channel 1100, the at least one channel 1100 extending from the top surface 1006a to the bottom surface 1006b of the fixation device guide 1006 and including a top opening 1105 on the top surface 1006a and a bottom opening 1106 on the bottom surface 1006b of the fixation device guide 1006. The at least one channel 1100 may be round, oblong, square or any shape configured to allow the fixation device 110 to traverse through the channel 1100 from the top opening 1105 to the bottom opening 1106. In embodiments, the fixation device guide 1006 may include multiple channels 1100a, 1100b, 1100c disposed in parallel orientation to each other. In an embodiment, as illustrated in FIGS. 11D-11E, the fixation device guide 1006 may include multiple channels 1100a, 1100b, 1100c disposed in non-parallel orientations relative to each other to allow fixation devices 110a, 110b, 110c, 110d, different angles of entry into the osseous tissue.

Figure 11F:
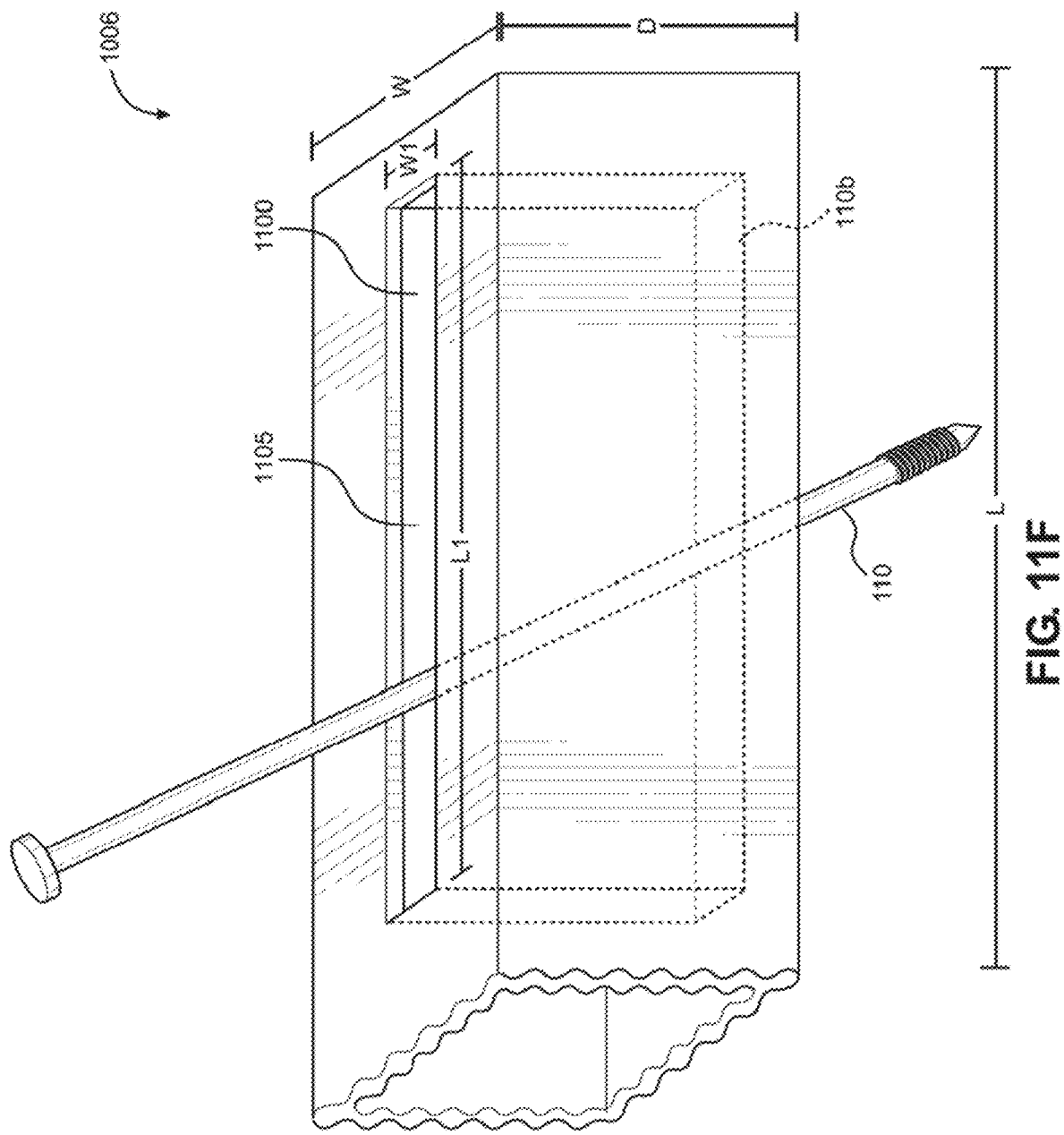
FIG. 11F is a 3-dimentional view of an embodiment fixation device guide.

In an embodiment, as illustrated in FIG. 11F, the fixation device guide 1006 comprises at least one channel 1100 starting at the top opening 1105 (rectangular in shape), the at least one channel 1100 extending through the thickness ("D") of the fixation device 1006 ending at the bottom opening 1106 (rectangular in shape). The top and bottom rectangular openings 1105, 1106 may include a length "L1" extending substantially the entire length "L" of the fixation device guide 1006. For example, length "L1" of the opening 1101 may range from about 95% to about 5% of the length "L". The top and bottom rectangular openings 1105, 1106 may include a width "W1" extending substantially the entire width "W" of the fixation device guide 1006. For example, width "W1" of the opening 1101 may range from about 95% to about 5% of the width In embodiments, FIG. 12 illustrates positioning of the surgical implant system 1000 comprising the surgical implant 100, the surgical implant guide 1001, the attachment mechanism 1005, the fixation device guide 1006, and at least one fixation device 110. The surgical implant 100 is inserted into a "V" shaped fracture 1203 created just above the anterior inferior iliac spine (AIIS) 1201, the surgical implant 100 detachably connected to the surgical implant guide 1001 employing an attachment mechanism 1005. The surgical implant 100 is further disposed in opposed, spaced relation relative to the fixation device guide 1006. Fixation device guide 1006 is disposed superior to the iliac crest 1202 and is configured to guide at least one fixation device 110 through the osseous tissue and further through an opening 107, 108 of the surgical implant 100. In an embodiment, the fixation device guide 1006 may include multiple multidirectional openings 1101a on the top surface 1006a and a rectangular opening 1101b on the bottom surface 1006b of the fixation device guide 1006. In an embodiment, a second fixation device 110 through the osseous tissue passed the fracture 1203 without traversing through openings 107, 108 of the surgical implant 100 and at least a second fixation device 110. The at least second fixation device 110 may be inserted into a space "S" (FIG. 6B) distal to the surgical implant's distal member 103. Upon installation of a trapezoidal surgical implant 100, the space "S" is created distal to the distal member 103 of the surgical implant 100. The second fixation device 110 may be inserted in or traverse the space "S" to improve bone healing and stabilization to the osseous tissue and the fracture 1203 by imparting compressing forces. The depth of the space "S" (i.e., distance between the distal member 103 of the surgical device to the distal end of the fracture 1203) depends on the length of the first and second side members 101, 102 of the surgical device 100. In embodiments, the depth of the space "S" may range from about 4 mm to about 3 cm, particularly, from about 1 cm to 2.5 cm.

Figure 13A:
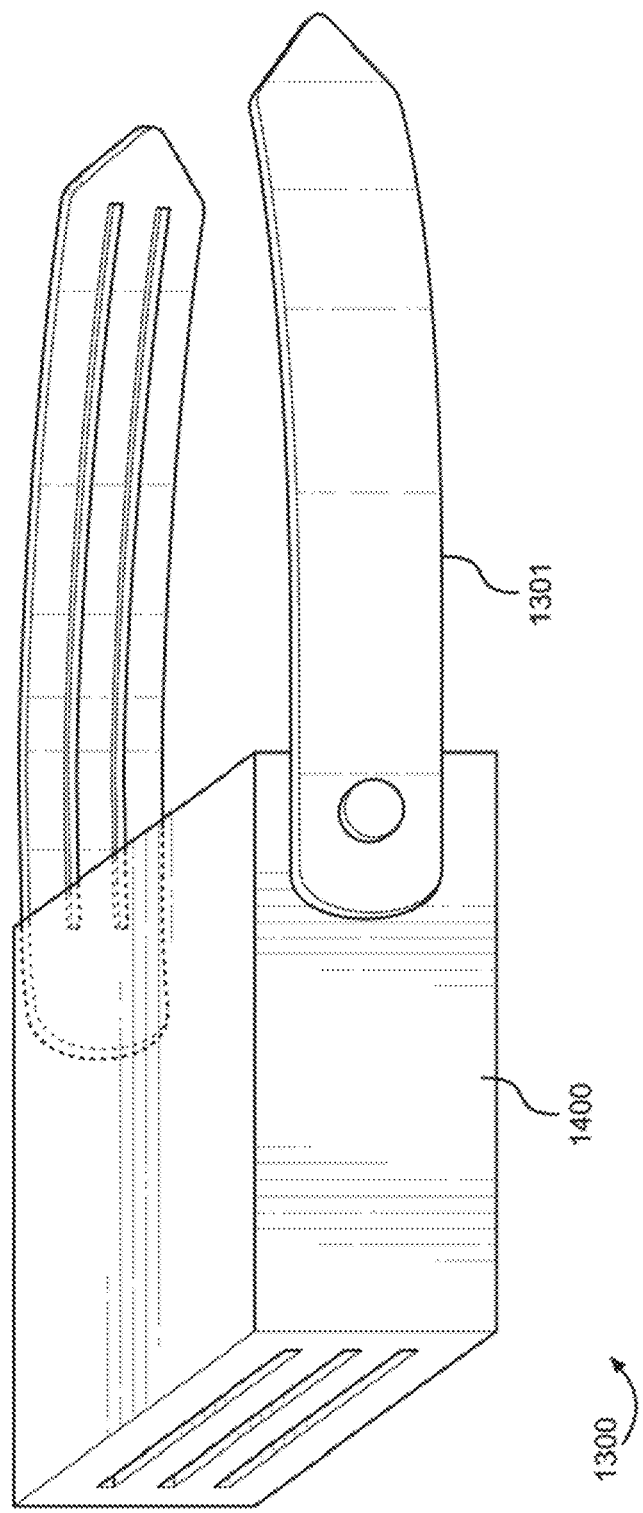
FIG. 13A is a 3-dimensional view of an embodiment osteotome guide system.

In an embodiment, FIG. 13A illustrates a 3-dimensional view of an osteotome guide system 1300 comprising at least one osteotomy protector 1301 and an osteotome guide 1400.

Figure 13B:
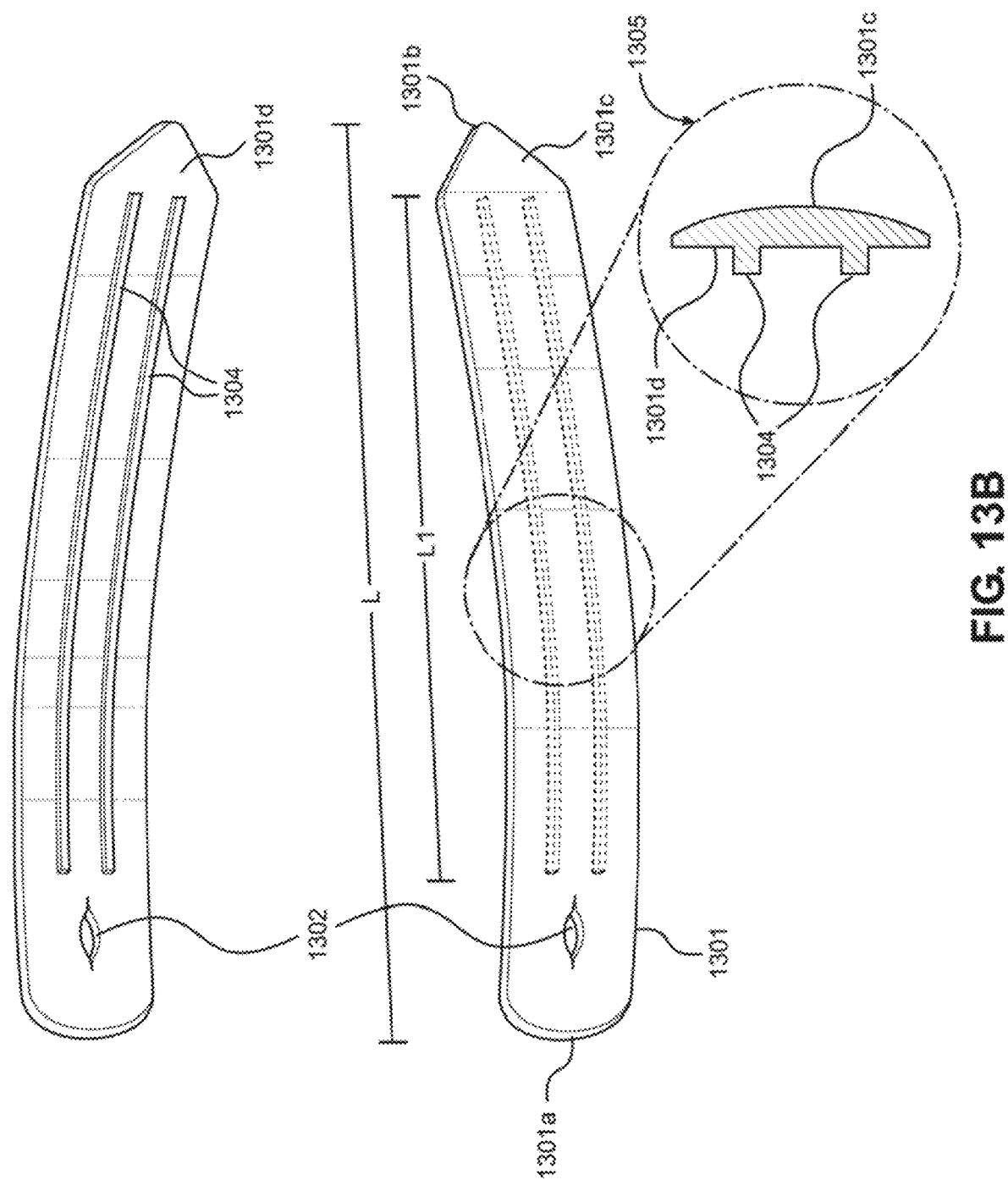
FIG. 13B is side views of an embodiment osteotomy protector.

In an embodiment, FIG. 13B illustrates front and back views of an osteotomy protector 1301. The osteotomy protector 1301 comprising a proximal end 1301a configured to connect to the osteotome guide 1400, a distal end 1301b configured to be inserted into and adjacent anatomical structures inside a patient's body, an outside surface 1031c, and an inside surface 1301d. The inside surface 1301d may be configured to include at at least one elongated ridge 1304 having a length "L1," the at least one elongated ridge 1304 extending substantially the entire length "L" of the osteotomy protector 1301. The osteotomy protector 1301 may be positioned inside a subject's body at the location of planned osteotomy procedure and configured to guide osteotomes which enter the subject's body along their cutting route, along its at least one elongated ridge 1304, and protect and shield anatomical structures, such as arteries and nerves, located adjacent to or near the cutting route of an osteotome from injury during the procedure. Illustrating a cross section 1305 of the embodiment osteotomy protector 1301, the osteotomy protector 1301 may include two ridges 1304 configured to capture and guide an osteotome which enters the patient's body. The osteotomy protector 1301 may further include a connection mechanism 1302 at the proximal end 1301a to attach and separate the osteotomy protector 1301 from the osteotome guide 1400. The connection mechanism 1302 may include a hole/button, snap button/hole, screw/hole or other known mechanism for connecting the osteotomy protector 1301 to the osteotome guide 1400.

The osteotomy protector 1301 is formed from biocompatible material(s) including, but not limited to metals and metal alloys, such as stainless steel, cobalt chrome, titanium, and titanium alloys, as well as polymers, such as polyether ether ketone ("PEEK"), or combinations of the aforementioned materials. The osteotomy protector 1301 may be made using an additive manufacturing process, for example, by printing or foaming material(s) having sufficient strength, and resiliency as needed or desired for a surgical procedure. For a detailed description of additive manufacturing processes suitable for forming the osteotomy protector 1301, reference can be made to U.S. Pat. Appl. Pub. No. 2016/0213485 to Schaufler et al., U.S. Pat. Appl. Pub. No. 2016/0213487 to Wilson et al., U.S. Pat. Appl. Pub. No. 2016/0213488 to Moore et al., and U.S. Pat. No. 9,987,051 to Nunley et al., the entire content of each of which is hereby incorporated by reference herein.

Figure 14B:
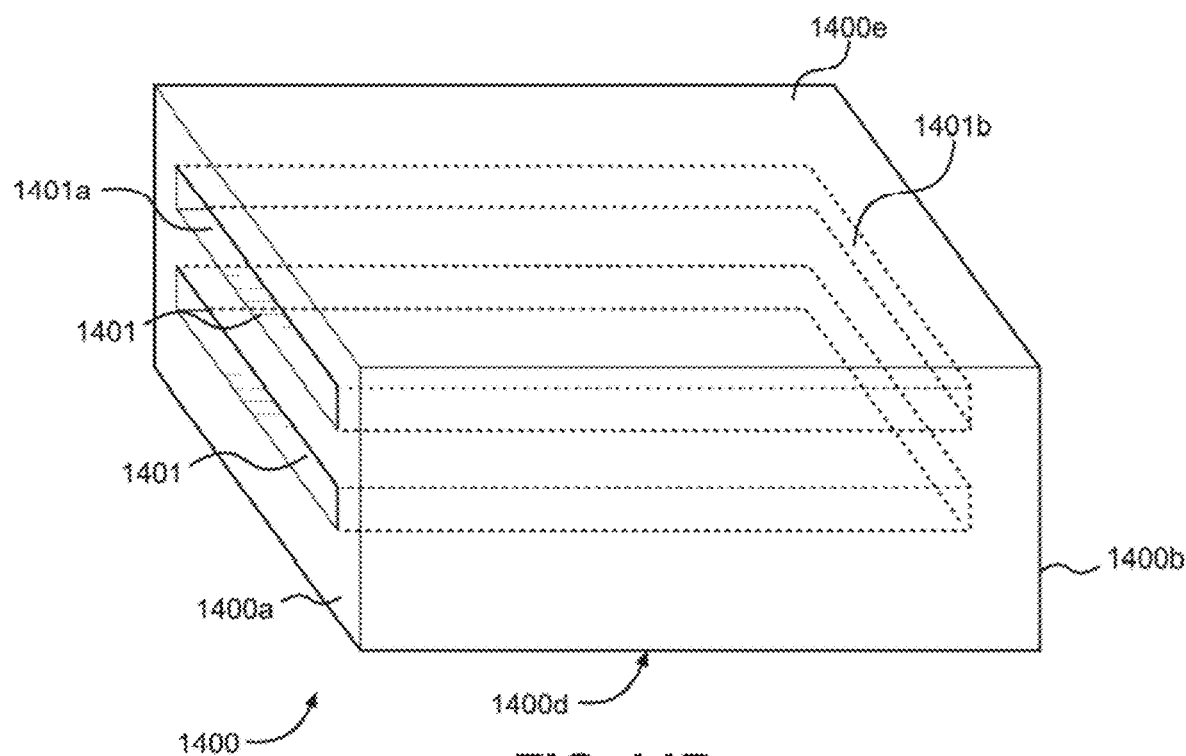
Figure 14C:
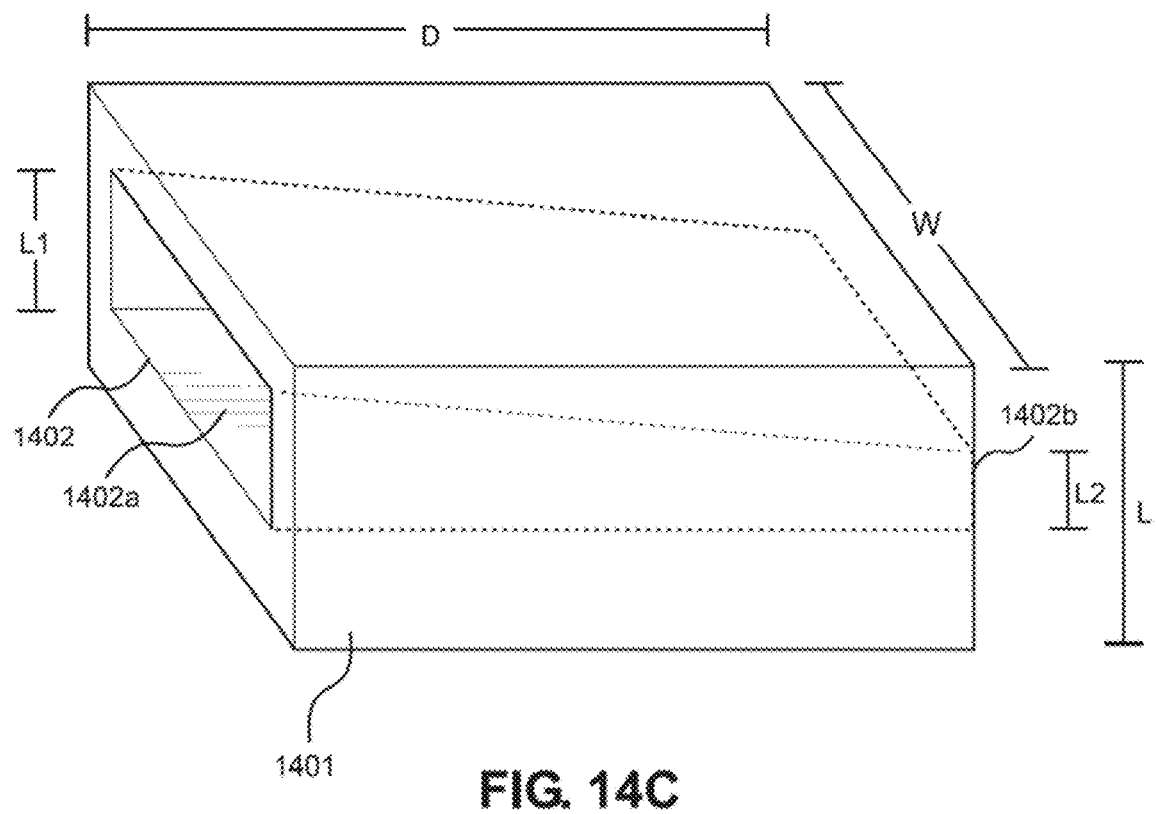

In an embodiment, FIGS. 14A-14C illustrate the osteotome guide 1400 configured to guide the trajectory, control distance of and stabilize osteotomes (not shown) during an osteotomy procedure. When creating cuts or fractures on anatomical structures, such as the skeletal system, an osteotome guide 1400 may be used to avoid advancing osteotomes 1600 too deep into the patient causing harm to neurovascular tissues. For example, in the pelvis, to perform an osteotomy through the ileum between the anterior inferior iliac spine (AIIS) and anterior superior iliac spine (ASIS), anteriorly, and the greater sciatic notch, posteriorly, several important anatomical structures must be protected, including the superior gluteal artery and other neurovascular structures. If osteotome is advanced too far, it could sever or damage important neurovascular structures.

In embodiments, the osteotome guide 1400 may comprise a housing 1401, at least one guiding channel 1402, at least one connection mechanism 1403 and at least one securing mechanism 1404. The housing 1401 may include at least a proximal surface 1401a and a distal surface 1401b and houses the at least one guiding channel 1402. The at least one guiding channel 1402 may include a first opening 1402a on the proximal surface 1401a of the housing 1401 and a second opening 1402b on the distal surface 1401b of the housing 1401. The depth "D1" of the at least one guiding channel 1402 is the same as the depth "D" of the housing 1401, the guiding channel 1402 is configured to receive and guide osteotomes entering through the first opening 1402a, traversing the channel 1402 in the housing 1401 and exiting the second opening 1402b to impale osseous tissue. In embodiments, the housing 1401 may include more than one separate guiding channels 1402 each extending the entire depth "D" of the housing 1401 parallel to the top or bottom surfaces 1041c, 1041d of the housing 1041, positioned at equal distances to one another. In other embodiments, multiple guiding channels 1402 may start at more than one first openings 1402a and converge inside the housing 1401 to exit through one second opening 1402b. FIGS. 14A and 14B each illustrate 3-dimentional views of embodiment housings 1401.

The osteotome guide 1400 may be positioned at a fracture site in a manner that the second opening 1402b is positioned adjacent to the cutting location. In this orientation, the osteotome immediately cuts the target bone as it exits the housing 1401 of the osteotome guide 1400 at the second opening 1402b. The osteotome guide 1400 may comprise a connection mechanism 1403 to removably connect the osteotomy protector 1301. The connection mechanism 1403 may be a hole/button, snap button/hole, screw/hole or other known mechanism to complement the connection mechanism 1302 of the osteotome protector 1301 and to connect the osteotomy protector 1301 to the osteotome guide housing 1401.

In an embodiment, the osteotome guide 1400 may be fixed at the cutting location and stabilized for the osteotomy procedure by at least one securing mechanism 1404. For example, the securing mechanism 1404 may comprise a body 1404*a* and an opening 1404*b*, the securing mechanism 1404 configured to receive pins or screws fixing the osteotome guide 1400 to a nearby or adjacent bone. The body 1404*a* may be fixedly attached at its base to the housing 1401 and configured to allow fixing or connecting the osteotome guide 1400 to an adjacent bone. In an embodiment, FIG. 15A illustrates fixing the osteotome guide 1400 to a nearby bony structure using a pin or a bone screw placed through the opening 1404*b* of the at least one securing mechanism 1404.

In an embodiment, FIG. 14C illustrates a 3-dimensional view of the osteotome guide 1400 comprising a housing 1401, the housing 1401 including at least one guiding channel 1402 with a first opening 1402*a* and a second opening 1402*b*. The first opening 1402*a* having a length "L1" and width "W1." The second opening having a length "L2" and width "W2." The lengths "L1," "L2" and widths "W1," "W2" of the first and second openings 1402*a*, 1402*b* are configured to accept and guide osteotomes. In an embodiment, the first opening 1402*a* is disposed in opposed relation relative to the second opening 1402*b*, the length "L1" of the first opening is longer than the length "L2" of the second opening 1402*b*, resulting in a slanted guiding channel 1402 configured to diverge multiple osteotomes onto one point.

Figure 15A:
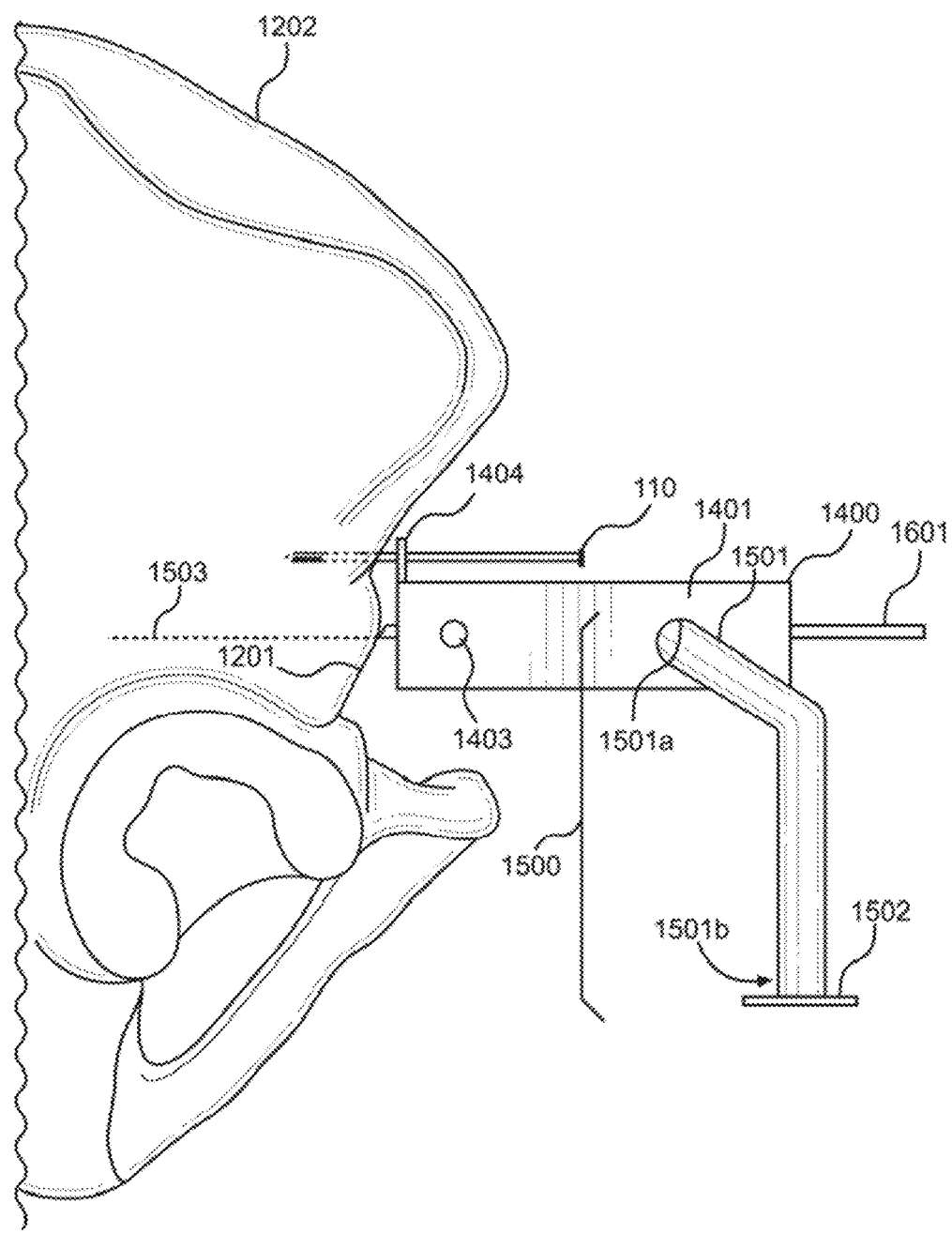
FIG. 15A is a side view of an embodiment osteotome guide system.
Figure 15B:
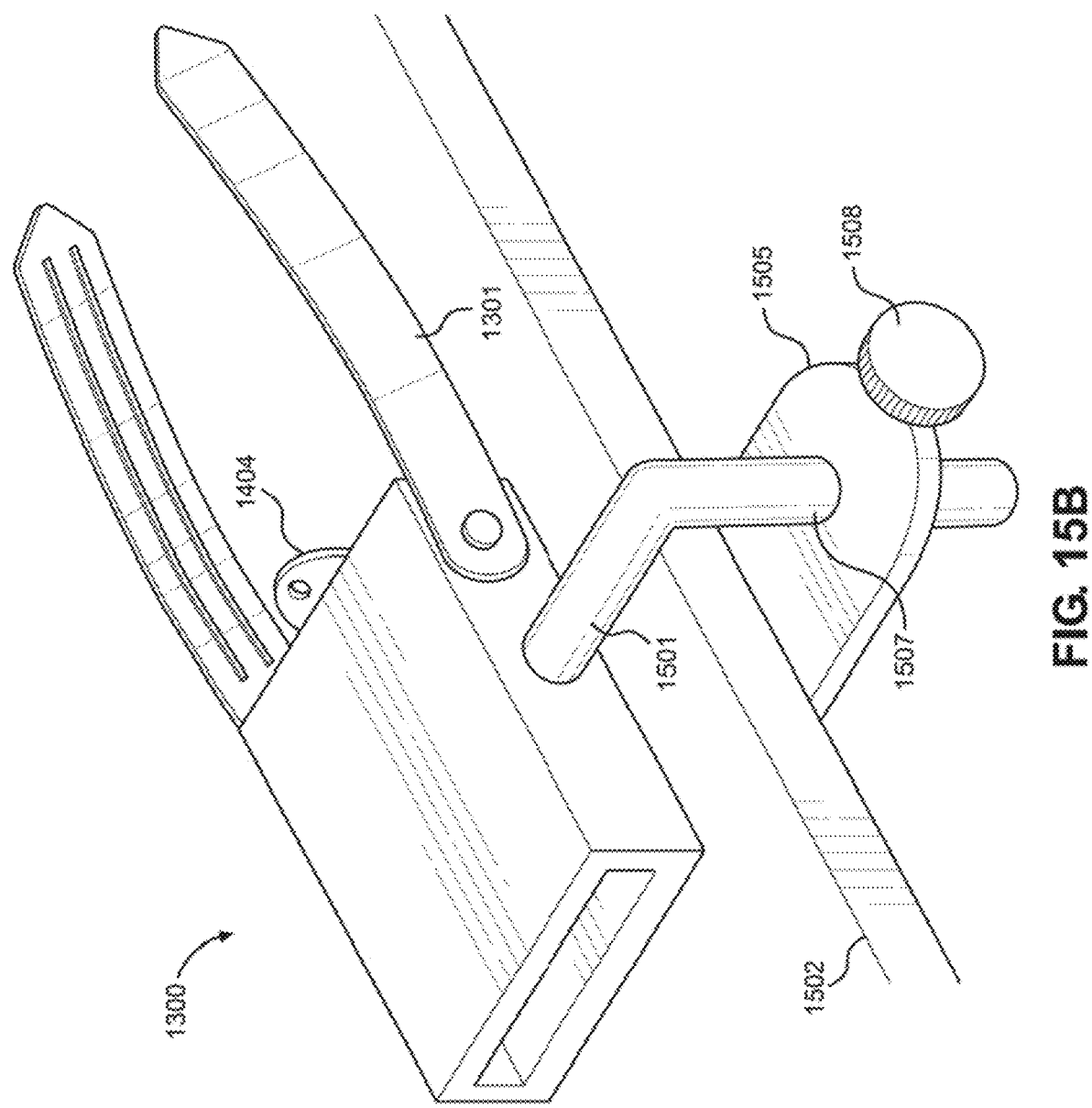
FIG. 15B is a 3-dimensional view of an embodiment osteotome guide system.

In an embodiment, FIGS. 15A and 15B illustrate a side view of an osteotome guide system 1300 comprising the osteotome guide 1400, at least one fixation device 110 and a supporting structure assembly 1500. The supporting structure assembly 1500 comprises a rod 1501 and a supporting structure 1505, the rod 1501 having a first end 1501*a* fixedly or movably connected to the osteotome guide housing 1401 and a second end 1501*b* configured to removably attach to or be secured to an external object 1502, such as a table. For example, the securing of the osteotome guide 1400 to an external object 1502 may be achieved by inserting the second end 1501 b of the rod 1501 into an opening 1507 located on the supporting structure 1505 and securing the rod 1501 to the supporting structure 1505 by tightening a screw 1508, such as shown in FIG. 15B. In embodiments, the supporting structure 1505 may be fixedly attached to the external object 1502. Fixedly attaching the rod 1501 to an external object may also be achieved using clamps or adhesives.

The osteotome guide 1400 is stabilized and connected to an adjacent or nearby bony structure, such as the pelvis bone, by at least one fixation device 110 placed through the opening 1404*b* of the stabilizing mechanism 1404. The supporting structure assembly 1500 provides additional or alternative mechanism which may be used to stabilize the osteotome guide 1400 by connecting the osteotome guide 1400 to an external object 1502, such as a table or chair. As such, the stabilizing mechanism 1404 fixes and stabilizes the osteotome guide 1400 to an anatomical structure of the subject while the supporting structure assembly 1500 fixes and stabilizes the osteotome guide 1400 to an external object 1502.

Figure 15C:
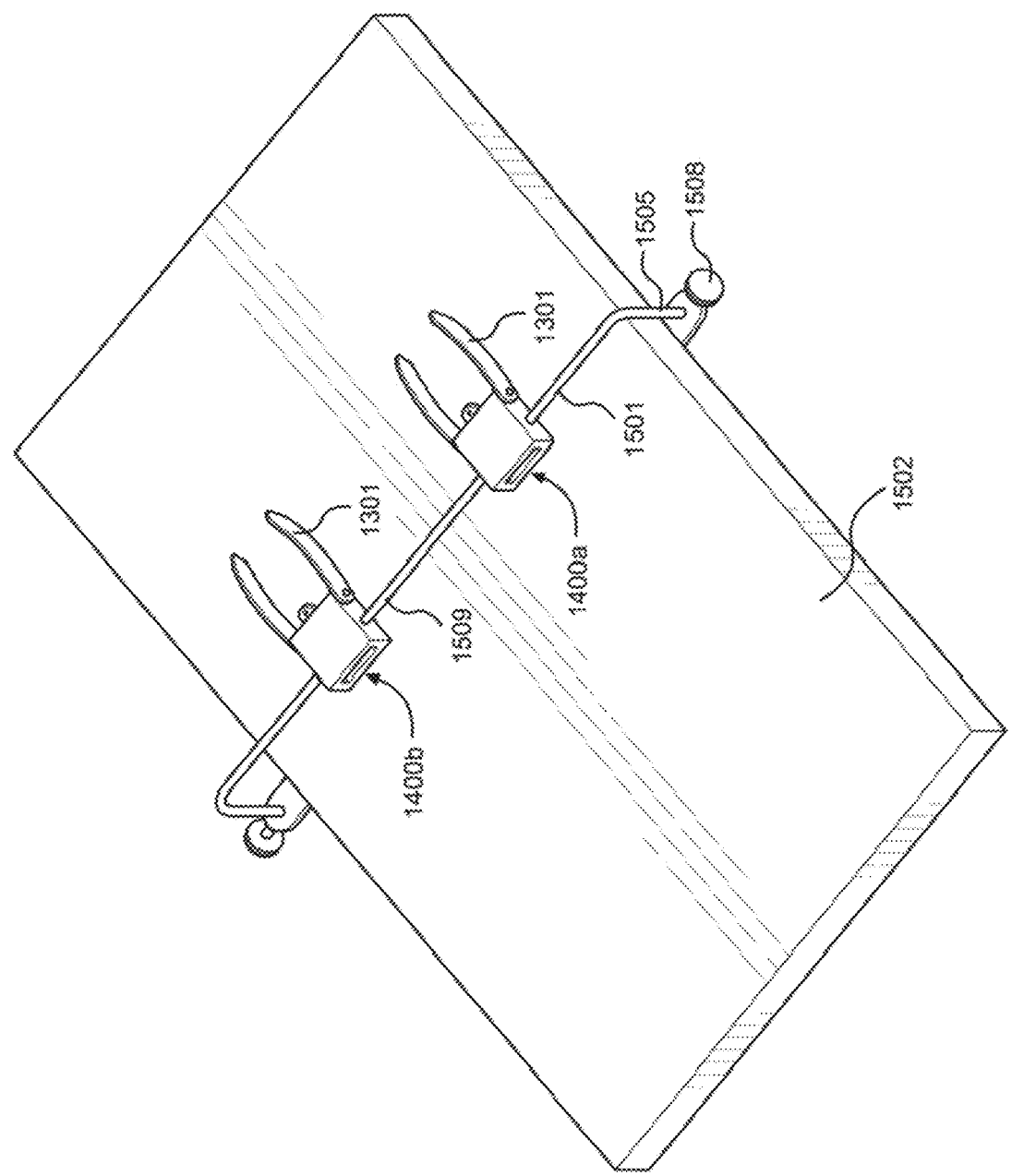
FIG. 15C is a 3-dimensional view of an embodiment osteotome guide system.

In an embodiment, FIG. 15C illustrates a 3-dimensional view of an embodiment multiple osteotome guide systems 1300, the osteotome guide system 1300 comprises multiple osteotome guides 1400, at least one connecting device 1509 and multiple a supporting structure assembly 1500. It is contemplated that at least two osteotomy systems 1300 may be used for bilateral fracturing of bony structures, such as the pelvic bone. When two or more osteotomy systems 1300 are used, the multiple osteotome guides 1400 may be first secured to an anatomical structure of the patient using the stabilizing mechanism 1404. Each osteotome guide 1400*a*, 1400*b* may be fixedly attached to an external object 1502 such as a table, using a supporting structure assembly 1500, the supporting structure assembly 1500 including the rod 1501, the supporting structure 1505 fixedly connected to the external structure 1502 and the screw 1508 configured to tighten the free end of the rod 1501 in the opening 1507. In embodiments, each osteotome guide 1400*a*, 1400*b* may also be connected to each other by a connecting rod 1509 to further stabilize the osteotome guides 1400*a*, 1400*b* against the subject's anatomical parts.

The osteotome guide system 1300 components may be formed from biocompatible material(s) including, but not limited to metals and metal alloys, such as stainless steel, cobalt chrome, titanium, and titanium alloys, as well as polymers, such as polyether ether ketone ("PEEK"), or combinations of the aforementioned materials. The osteotome guide 1400 may be made using an additive manufacturing process, for example, by printing or foaming material(s) having sufficient strength, and resiliency as needed or desired for a surgical procedure. For a detailed description of additive manufacturing processes suitable for forming the osteotome guide 1400, reference can be made to U.S. Pat. Appl. Pub. No. 2016/0213485 to Schaufler et al., U.S. Pat. Appl. Pub. No. 2016/0213487 to Wilson et al., U.S. Pat. Appl. Pub. No. 2016/0213488 to Moore et al., and U.S. Pat. No. 9,987,051 to Nunley et al., the entire content of each of which is hereby incorporated by reference herein.

Figure 16B:
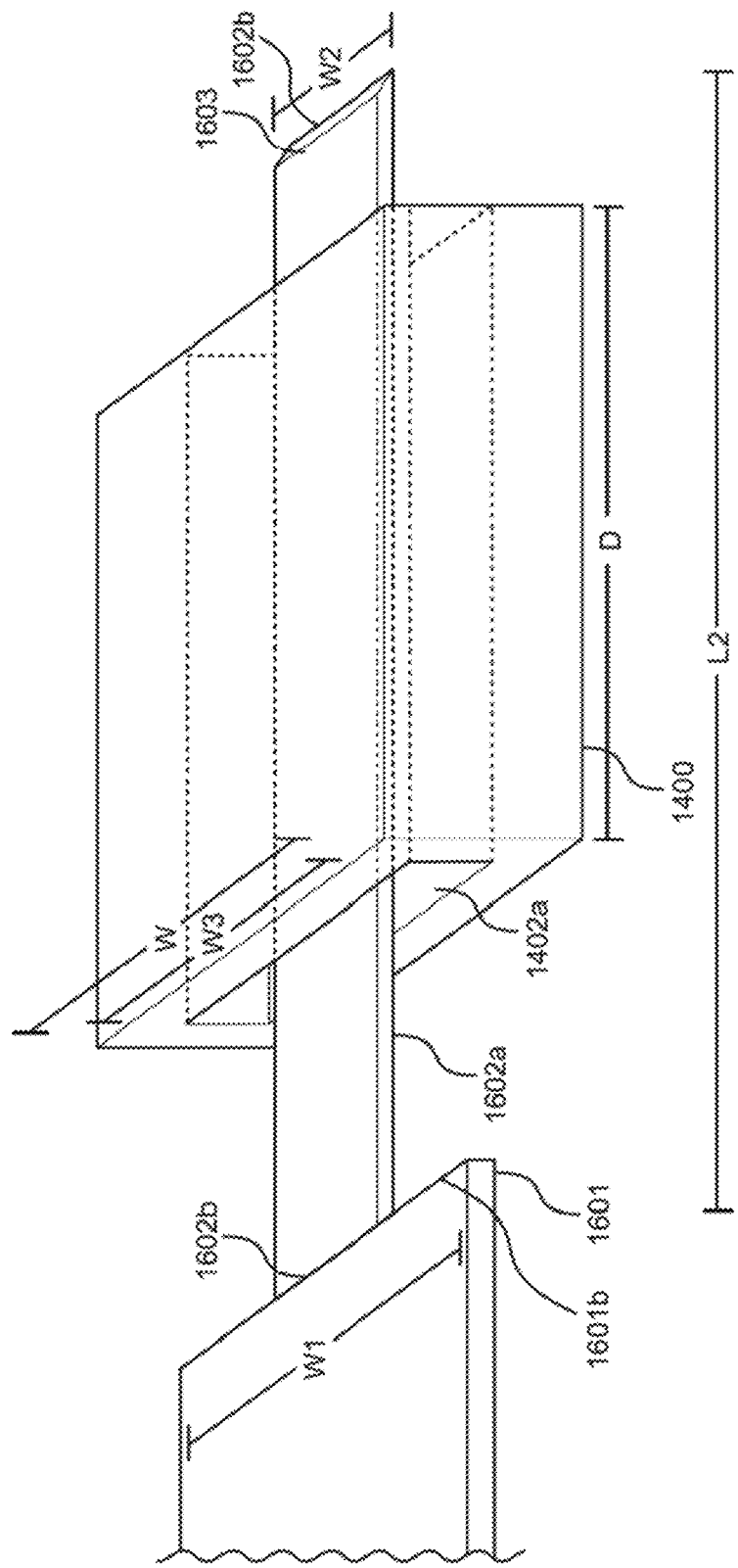
FIG. 16B is a 3-dimensional view of an osteotome of FIG. 16A engaged with the osteotome guide system of FIG. 13A.

In an embodiment, FIGS. 16A-16B illustrate a side view of various designs of cutting devices or osteotomes 1600. FIG. 16A illustrates osteotomes 1600 comprising a head 1601, and a body 1602. The head 1601 is fixedly connected to the body 1602. The head 1601 may include a width "W1" that is longer than the width "W2" of the of the body 1602. The body 1602 comprises a top end 1602*a* and a bottom end 1602*b*. The top end 1602*a* is fixedly connected to the head 1601. The bottom end 1602*b* includes a sharp edge 1603 configured to cut through osseous tissue. In an embodiment, the osteotome 1600*e* may include a jagged sharp edge 1603. In yet another embodiment, the osteotome 1600*d* may only include a body 1602. The dimensions of embodiment osteotomes 1600 may be variable and determined based on the cutting size and distance required and different sizes and shapes are contemplated for the embodiment osteotomes 1600.

In embodiment, FIG. 16B illustrates a 3-dimensional view of an osteotome 1600 engaged in an osteotome guide 1400. The head 1601 of the osteotome 1600 may include a width "W1" that is larger than the width "W" of the opening 1402*a* of the osteotome guide 1400. The body 1602 of the osteotome 1600 may include a width "W2" that is smaller than the width "W3" of the opening 1402*a* of the osteotome guide 1400. The body 1602 is configured to travel through the at least one channel 1402 of the osteotome guide 1400. The length "L2" of the body 1602 is longer than the depth "D" of the osteotome guide 1400. The length "L1" of the body 1602 is determined based on the distance the osteotome 1600 must cut an anatomical structure, such as the osseous tissue. Because the width "W1" of the head 1601 is longer than the width "W" of the osteotome guide 1400, the bottom end 1601b of the head 1601 will touch the proximal surface 1401a of the osteotome guide housing 1401, stopping the cutting process once the desired cutting distance is achieved by the osteotome 1400, thus, preventing damage to distant anatomical structures such as neurovascular tissue.

In an embodiment, a method of installing the surgical implant 100 may include forming an opening or fracture in the osseous tissue, such as in the pelvic bone, along an osteotomy line 1503; inserting a surgical implant 100 in the opening; and, inserting a fixation device 110 through the osseous tissue and the surgical implant 100, anchoring the surgical implant 100 to the osseous tissue.

Figure 17:
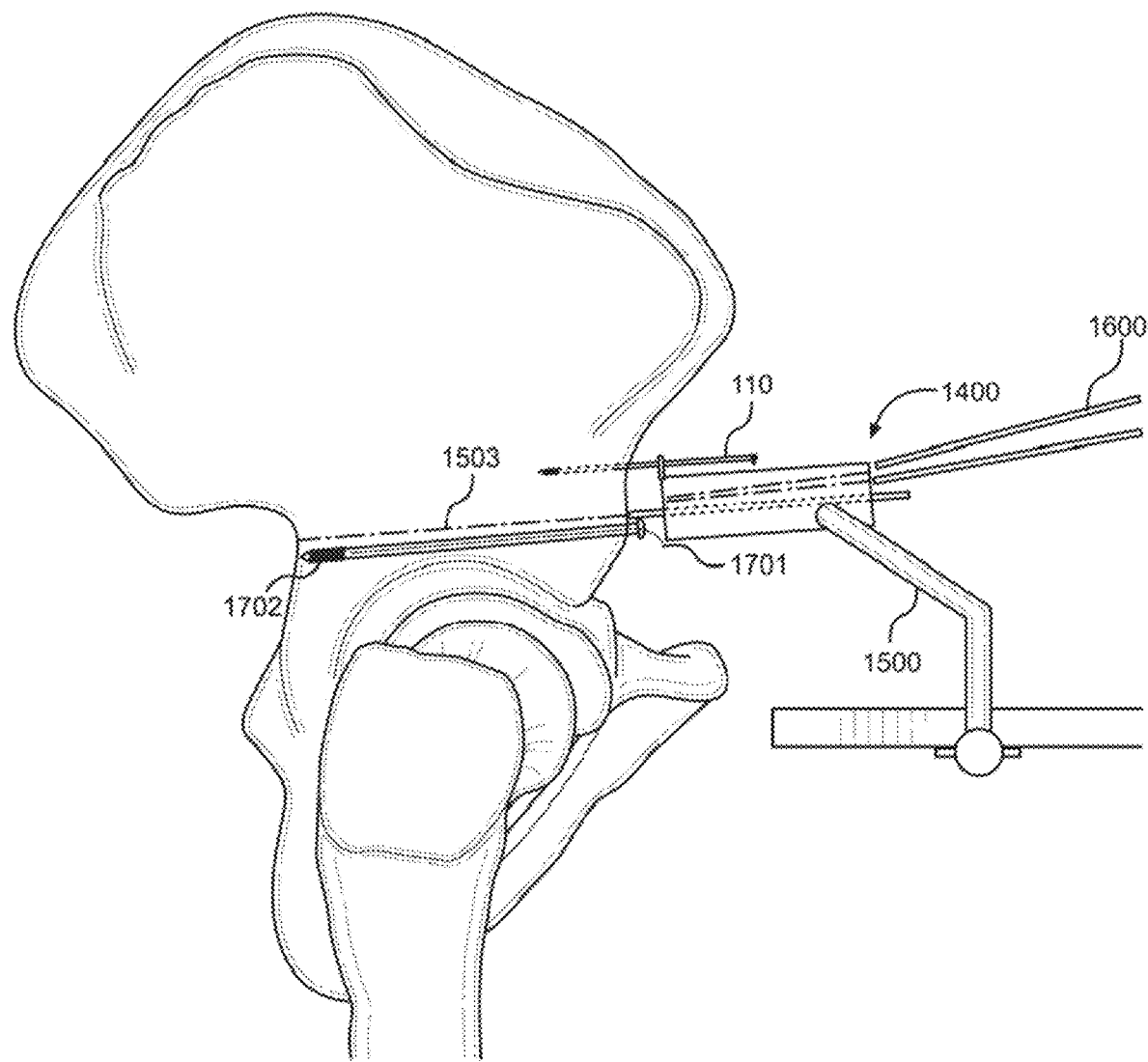
FIG. 17 is a side view of a pelvic bone of FIG. 12, and the osteotome guide system of FIG. 15A.

FIG. 17 illustrates a side view of pelvis bone and osteotome guide system 1300 positioned to create an opening along an osteotomy line 1503. In an embodiment, the forming of an opening in osseous tissue may comprise obtaining a fluoroscopy view of the pelvis, making a skin incision at the osteotomy line 1503 position; inserting a guide wire in the osseous tissue, positioning and anchoring an osteotome guide 1400 adjacent to the osteotomy line 1503 in the osseous tissue; inserting osteotome(s) 1600 through the osteotome guide 1400 to form the opening or fracture the osseous tissue at the osteotomy line 1503. In an embodiment, a fluoroscopy view of the pelvis may include fluoroscopy view parallel to the wall of the ilium in line with posterior column in a manner that there is no parallax visible, and the inner and outer cortices of the ilium are in line with the ischium. In an embodiment, a guide wire 1701 may be advanced from the anterior third of the ilium through the inner and outer tables of the ilium posterior to the acetabulum and into the ischium. The guide wire 1701 may be placed with or without employing navigational tools such as O-arm™ or a robotic arm. In an embodiment, a bone tap 1702 may be advanced over the guide wire to minimize the bending of the guide wire during the procedure. The osteotome guide 1400 may be placed adjacent and over the bone tap 1702, the bone tap 1702 informs and provides the correct plane of osteotomy.

In an embodiment method, the osteotomy procedure comprises using a cutting device, such as a surgical scalpel, forming an opening in or making an incision in the skin over the osteotomy line 1503 location. The making an incision in the skin may include a vertical or horizontal cut at the level of the osteotomy line 1503, such as at AIIS, dissecting down through the subcutaneous tissue, fat, and fascia down to the bone; dissecting the tissue on either side of the iliac bone and inserting the osteotomy protectors 1301 between the soft tissue and the exposed osseous tissue, for example, around greater sciatic notch to protect the superior gluteal nerve, artery and vein. The osteotome guide 1400 may be anchored and secured to the patient's osseous tissue, such as by pinning the osteotome guide 1400 using a securing mechanism 1404 (for example, with two pins or four pins caudal and cephalad to level of osteotomy), and/or to an external object by using a supporting structure assembly 1500. Based on preoperative planning (e.g., CT's and X-rays), the at least one osteotome 1600 of desired length and width may be used to cut the osseous tissue. In an embodiment, the bone tap 1702 may be placed in a manner to intersect the osteotomy line 1503 at the posterior section of the osteotomy line 1503. In such scenarios when bone tap 1702 intercepts the osteotomy line 1503, the osteotome 1600 may be advanced in the osseous tissue until the osteotome 1600 reaches and intercepts the bone tap 1702 at a posterior location of the osteotomy line 1503. The bone tap 1702 may be retracted just passed the osteotomy line 1503. The intercept of the bone tap 1702 and the osteotome 1600 may create an angulation measurement to allows the user to see the angle of correction through the osteotomy.

In an embodiment, the inserting a surgical implant 100 may further include inserting the surgical implant 100 removably attached to a surgical implant guide system 1000, the surgical implant guide system 1000 configured to align the surgical implant openings 107, 108 with the path of fixation devices 110 inserted through osseous tissue outside of the opening formed in the osseous tissue by the osteotome 1600. Aligning the openings on the fixation device guide 1006 with the openings 107, 108 of the surgical implant 100, anchoring the surgical implant to the osseous tissue comprises, inserting at least one fixation device 110 through the fixation device guide 1006 opening 1101, through the osseous tissue adjacent to the fixation device guide 1006; advancing the fixation device 110 through osseous tissue to reach the opening 107 of the surgical implant 100; traversing the fixation device 110 through the opening 107 and advancing the fixation device 110 through the cavity 109 of the surgical implant 100 to reach the opening 108 of the surgical implant 100; traversing through the opening 108 of the surgical implant 100; and, advancing the fixation device 110 through the osseous tissue adjacent to the opening 108. In an embodiment, inserting a fixation device 110 using a fixation device guide 1006 may further include inserting a guide wire through the opening 1100 of the fixation device guide 1006; advancing the guide wire through the osseous tissue to reach the opening 107; traversing the guide wire through the openings 107, cavity 109 and opening 108 of the surgical implant 100; and, advancing the guide wire through the osseous tissue adjacent to the opening 108. Subsequently, inserting a fixation device 110 over the guide wire to ensure that the fixation device 110 will traverse the osseous tissue and openings 107, 108 of the surgical implant 100.

In an embodiment, the method of installing the surgical implant 100 using a surgical implant guide system 100 may further include detaching the surgical implant 100 from the attachment mechanism 1005 of the surgical implant guide system 1000 and attaching a bone plate 500 to the surgical implant 100. In embodiments, trial plates may be utilized for initial fitting and size confirmation. A plate holder may be utilized to seat the bone plate 500 flush against the pelvic bone. Fixation devices 110 may be inserted to secure the bone plate to the osseous tissue. Holes may be drilled into the osseous tissue prior to inserting fixation devices 110 to minimize bone damage during the procedure. In an embodiment, prior to inserting the surgical implant 100, the at least one cavity 109 of the surgical implant 100 may be filled with bone growth material. A standard wound closure procedure may then be used to complete the procedure.

In embodiments, the surgical implant 100 may be inserted in the pelvic bone for correction of spinal deformity by employing a surgical implant guide system 1000. At least one fixation device 110 may be inserted from the iliac crest towards ischium, through the osseous tissue of ilium, traversing through the openings 107, 108 of the inserted surgical implant 100 and subsequently impaling through the osseous tissue located inferior to the surgical implant 100. Additional fixation devices 110 may be inserted through the ilium and through the space "S" in the fracture 1203 but without engaging or traversing openings 107, 108 of the surgical implant 100, imparting compression forces on the bone to promote healing.

The various embodiment methods may be performed using navigational and/or robotic systems. Navigational tool may allow a perpendicular osteotomy by registering a CT scan obtained prior to surgery to the position of the pelvis at time of surgery. Navigation tools may also allow for placement of fixation devices 110. Robotic arm may allow for making pre-planned CT cuts for osteotomy and fixation device 110 placement. For a detailed description of suitable navigational or robotic systems and methods reference can be made to U.S. Pat. No. 9,283,048 to Kostrzewski et al., U.S. Pat. No. 5,408,409 to Glassman et al., U.S. Pat. Appl. No. 2017/0056116 to Kostrzewski et al., U.S. Pat. App. No. 2015/0100066 to Kostrzewski et al., and U.S. Pat. No. 9,592,096 to Maillet et al the entire content of each of which is hereby incorporated by reference herein.

The surgical implant 100, surgical implant system or assembly 10, or the surgical implant guiding system 1000 may be provided in a kit. In an embodiment, the kit may be an assembled package including at least one surgical implant 100 and at least one fixation device 110. The kit may further include at least one bone plate 500. In another embodiments, the kit may include a plurality of surgical implants 100 of various sizes (e.g., surgical implants having different lengths and/or widths), a plurality of fixation devices 110 of various lengths (e.g., 45 mm, 60 mm, etc.) and types (e.g., low-profile head screws, rounded-head screws, pins, shims, wedges, blades, etc.), and/or a plurality of bone plates 500 of various configurations to allow a user to pick and choose one or more suitable components for a surgical procedure. In another embodiment, the kit may include stackable surgical implants 800. In another embodiment, the kit may include surgical implant guiding system 1000 in addition to the at least one surgical implant 100, at least one bone plate 500 and at least one fixation device 110. In an embodiment, the kit may include osteotome guide system 1300, including osteotome guide 1400, osteotomy projectors 1301 and osteotomes 1600 of various sizes, in addition to the at least one surgical implant 100, at least one bone plate 500 and at least one fixation device 110. The kit may include a first container or compartment including the at least one surgical implant 100, and, optionally, the surgical implant guiding system 1000. The kit may include a second container or compartment including the at least one fixation device 110. The kit may further include a third container or compartment including the at least one bone plate 500. The kit may further include a fourth container including an osteotome guide system 1300. The kit may include a fifth container including osteotomes 1600.

It is envisioned that the surgical implant 100 may be solid, open-faced, and/or expandable. The surgical implant 100 may be expanded by an active or passive mechanism and/or include a height expansion/reduction mechanism to allow for dynamic changes to the height and/or length of the surgical implant 100. The surgical implant 100 can be built in-situ by a user inside of osseous tissue to tailor the surgical implant 100 to conform to the anatomy of an individual patient.

While various embodiments of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims. Throughout this description, the term "proximal" refers to a portion of a system, a device, or a component thereof, that is closer to a user, and the term "distal" refers to a portion of the system, the device, or the component thereof, that is farther from the user. In the drawings and the foregoing description, terms such as "front," "back," "upper," "lower," "top," "bottom ," "side," and similar directional terms are used for convenience of description and are not intended to limit the disclosure.

The foregoing discussion of the disclosure has been presented for purposes of illustration and description and include non-limiting exemplary embodiments. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:
1. A surgical implant assembly comprising:
at least one surgical implant comprising:
a first side member, including at least one first opening, a first side member distal end and a first side member proximal end, wherein the first side member has a contoured shape matching the contoured shape of adjacent bone to which it will be placed;
a second side member, including at least one second opening, a second side member distal end and a second side member proximal end, the second side member disposed in opposed relation relative to the first side member, wherein the second side member has a contoured shape matching the contoured shape of adjacent bone to which it will be placed;
a distal member including a right end and a left end, interconnecting the first side member and the second side member, the right end connecting to the first side member distal end and the left end connecting to the second side member distal end;
a top member and a bottom member disposed in opposed, spaced relation relative to the top member, the top and bottom members are interconnected through their parameter by the first side member, the second side member, the distal member, and a proximal member; and
a fixation device insertable through the at least one first opening and the at least one second opening,
wherein the fixation device is insertable through a first osseous tissue, into the at least one first opening, the at least one second opening and a second osseous tissue.

2. A method of implanting a surgical implant into an osseous tissue comprising:
- forming an opening in the osseous tissue of a pelvis;
- inserting a surgical implant into the opening of the osseous tissue, the surgical implant comprising:
  - a first side member, including at least one first opening, a first side member distal end and a first side member proximal end, wherein the first side member has a contoured shape matching the contoured shape of adjacent bone to which it will be placed;
  - a second side member, including at least one second opening, a second side member distal end and a second side member proximal end, the second side member disposed in opposed relation relative to the first side member, wherein the second side member has a contoured shape matching the contoured shape of adjacent bone to which it will be placed; and
  - a distal member including a right end and a left end, interconnecting the first side member and the second side member, the right end connecting to the first side member distal end and the left end connecting to the second side member distal end; and,
- anchoring the surgical implant to the osseous tissue by inserting at least one fixation device through a first osseous tissue, the at least one first opening, and the at least one second opening and a second osseous tissue.

* * * * *